United States Patent [19]

Hansen et al.

[11] Patent Number: 6,127,341
[45] Date of Patent: Oct. 3, 2000

[54] COMPOUNDS WITH GROWTH HORMONE RELEASING PROPERTIES

[75] Inventors: Thomas Kruse Hansen, Herlev; Jesper Lau, Farum; Bernd Peschke, Malov; Michael Ankersen, Frederiksberg; Kjeld Madsen, Vaerlose; Nils Langeland Johansen, Copenhagen O, all of Denmark

[73] Assignee: Novo Nordisk A/S, Bagsvaerd, Denmark

[21] Appl. No.: 09/088,690

[22] Filed: Jun. 1, 1998

Related U.S. Application Data

[60] Provisional application No. 60/050,816, Jun. 26, 1997.

[30] Foreign Application Priority Data

Jun. 20, 1997 [DK] Denmark ................................. 0725/97

[51] Int. Cl.[7] ........................... A61K 38/00; C07C 233/00
[52] U.S. Cl. ........................ 514/18; 514/19; 530/329.1; 530/330; 530/331; 548/29; 549/300.1; 562/445; 562/448; 562/450; 564/153; 564/155; 564/164; 560/158
[58] Field of Search ............................ 560/158; 514/18, 514/19; 549/29; 548/300.1; 562/445, 448, 450; 564/155, 164, 153; 530/329.1, 330, 331

[56] References Cited

U.S. PATENT DOCUMENTS

| | | | |
|---|---|---|---|
| 5,663,146 | 9/1997 | Bowers et al. | 514/16 |
| 5,767,085 | 6/1998 | Johansen et al. | 514/17 |
| 5,776,901 | 7/1998 | Bowers et al. | 514/16 |
| 5,798,337 | 8/1998 | Johansen et al. | 514/19 |
| 5,889,110 | 3/1999 | Hutchinson | 525/54.1 |

FOREIGN PATENT DOCUMENTS

| | | |
|---|---|---|
| wo 95/17423 | 6/1995 | WIPO . |
| WO 96/15148 | 5/1996 | WIPO . |
| wo 96/22997 | 8/1996 | WIPO . |
| WO 97/00894 | 1/1997 | WIPO . |
| WO 97/23508 | 7/1997 | WIPO . |
| WO 98/03473 | 1/1998 | WIPO . |

*Primary Examiner*—Porfirio Nazario-Gonzalez
*Attorney, Agent, or Firm*—Steve T. Zelson; Carol E. Rozek

[57] ABSTRACT

Compounds of the general formula I

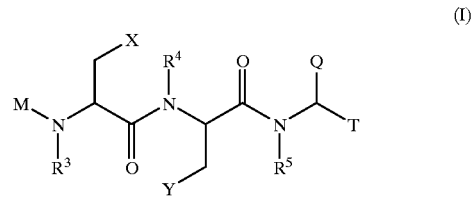

compositions containing them, and their use for treating medical disorders resulting from a deficiency in growth hormone are described.

21 Claims, No Drawings

COMPOUNDS WITH GROWTH HORMONE RELEASING PROPERTIES

CROSS-REFERENCE TO RELATED APPLICATIONS

This application claims priority under 35 U.S.C. 119 of U.S. provisional application Ser. No. 60/050,816 filed on Jun. 26, 1997 and Danish application no. 0725/97 filed Jun. 20, 1997, the contents of which are fully incorporated herein by reference.

FIELD OF INVENTION

The present invention relates to novel compounds, compositions containing them, and their use for treating medical disorders resulting from a deficiency in growth hormone.

BACKGROUND OF THE INVENTION

Growth hormone is a hormone which stimulates growth of all tissues capable of growing. In addition, growth hormone is known to have a number of effects on metabolic processes, e.g., stimulation of protein synthesis and free fatty acid mobilization and to cause a switch in energy metabolism from carbohydrate to fatty acid metabolism. Deficiency in growth hormone can result in a number of severe medical disorders, e.g., dwarfism.

Growth hormone is released from the pituitary. The release is under tight control of a number of hormones and neurotransmitters either directly or indirectly. Growth hormone release can be stimulated by growth hormone releasing hormone (GHRH) and inhibited by somatostatin. In both cases the hormones are released from the hypothalamus but their action is mediated primarily via specific receptors located in the pituitary. Other compounds which stimulate the release of growth hormone from the pituitary have also been described. For example arginine, L-3,4-dihydroxyphenylalanine (L-Dopa), glucagon, vasopressin, PACAP (pituitary adenylyl cyclase activating peptide), muscarinic receptor agonists and a synthethic hexapeptide, GHRP (growth hormone releasing peptide) release endogenous growth hormone either by a direct effect on the pituitary or by affecting the release of GHRH and/or somatostatin from the hypothalamus.

In disorders or conditions where increased levels of growth hormone is desired, the protein nature of growth hormone makes anything but parenteral administration non-viable. Furthermore, other directly acting natural secretagogues, e.g., GHRH and PACAP, are longer polypeptides for which reason oral administration of them is not viable.

The use of certain compounds for increasing the levels of growth hormone in mammals has previously been proposed, e.g. in EP 18 072, EP 83 864, WO 89/07110, WO 89/01711, WO 89/10933, WO 88/9780, WO 83/02272, WO 91/18016, WO 92/01711, WO 93/04081, WO 95/17422, WO 95/17423 and WO 95/14666.

The composition of growth hormone releasing compounds is important for their growth hormone releasing potency as well as their bioavailability. It is therefore an object of the present invention to provide novel compounds with growth hormone releasing properties. Moreover it is an object to provide growth hormone releasing compounds with no or substantially no side-effects. It is also an object to provide compounds which have good oral bioavailability.

SUMMARY OF THE INVENTION

In accordance with the present invention there is provided compounds which act directly on the pituitary cells under normal experimental conditions in vitro to release growth hormone therefrom.

These growth hormone releasing compounds can be utilised in vitro as unique research tools for understanding, inter alia, how growth hormone secretion is regulated at the pituitary level.

Moreover, the growth hormone releasing compounds of the present invention can also be administered in vivo to increase growth hormone release.

Accordingly, the present invention relates to a compound of general formula I

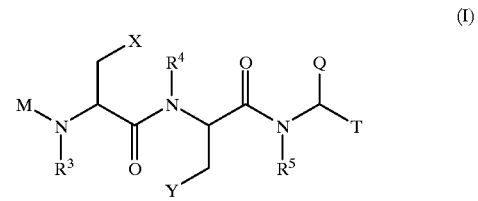

(I)

wherein $R^3$, $R^4$, $R^5$, X, Y, M, T and Q are as defined below, or a pharmaceutically acceptable salt thereof, having growth hormone releasing properties.

DESCRIPTION OF THE INVENTION

In a broad aspect the present invention relates to a compound of general formula I

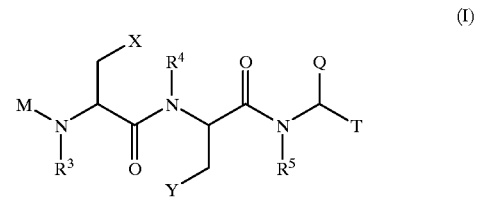

(I)

wherein
$R^3$, $R^4$ and $R^5$ independently of each other are hydrogen, or $C_{1-6}$ alkyl optionally substitued with $C_{1-6}$ alkyl,
X is aryl optionally substituted with halogen, $C_{1-6}$ alkyl or phenyl,
Y is aryl or hetaryl optionally substituted with halogen, $C_{1-6}$ alkyl, $C_{1-6}$ alkoxy or phenyl,
M is $M^1$, $M^2$, $M^3$, $M^4$ or $M^5$
wherein $M^1$ is —C(=O)—CH=CH—$(CH_2)_m$—C$(R^{16}R^{17})$—N$(R^1R^2)$,
$M^2$ is —C(=O)—CH$((CH_2)_m$-hetaryl)—NH—C(=O)—C$(R^{16}R^{17})$—N$(R^1R^2)$, wherein m is 1, 2 or 3, and
$R^{16}$ and $R^{17}$ independently of each other are $C_{1-6}$ alkyl, optionally substituted with halogen, amino, hydroxyl, $C_{1-6}$ alkyl, $C_{1-6}$ alkoxy or phenyl;
$M^3$ is —C(=O)—$D^1$—$CH_2$—N$(R^1R^2)$,
$M^4$ is —C(=O)—$D^1$—C$(R^6R^7)$—N$(R^1R^2)$, and
$M^5$ is —C(=O)—$(CH_2)_s$—O—$(CH_2)_p$—C$(R^6R^7)_q$—A, wherein $R^6$ and $R^7$ independently of each other are hydrogen, $C_{1-6}$ alkyl, $D^1$ is arylene, such as phenylene or naphthylene, preferably phenylene, p and s independently of each other are 1, 2 or 3, q is 0 or 1, and A is —N$(R^1R^2)$ or a saturated heterocyclic ring containing 5 or 6 ring members, one ring member being a heteroatom such as N, S and/or O, preferably N,
wherein $R^1$ and $R^2$ independently of each other are hydrogen, —C(=O)—$C_{1-6}$ alkyl, $C_{1-6}$ alkyl optionally substituted with halogen, amino, hydroxyl, $C_{1-6}$ alkyl, $C_{1-6}$ alkoxy or phenyl; or benzyl, optionally substituted with halogen, amino, hydroxyl, $C_{1-6}$ alkyl, $C_{1-6}$ alkoxy or phenyl, T is hydrogen, $T^1$, $T^2$ or $T^3$, wherein $T^1$ is —$(CH_2)_n$—$NH_2$, wherein n is 1, 2, 3, 4, 5, 6, 7, 8, 9 or 10, $T^2$ is —$(CH_2)_n$—$N(R^8R^9)$, wherein n is 1, 2, 3, 4, 5, 6, 7, 8, 9 or 10, and $R^8$ and $R^9$ independently of each other are $C_{1-6}$ alkyl optionally substituted with halogen, amino, hydroxyl, $C_{1-6}$ alkyl, $C_{1-6}$ alkoxy or phenyl, or $R^8$ and $R^9$ may be joined to form a saturated heterocyclic ring containing 5 or 6 ring members, one of the ring members being N and the other being carbon atoms; and $T^3$ is —$(CH_2)_n$—NHZ, wherein n is 1, 2, 3, 4, 5, 6, 7, 8, 9 or 10, and Z is —$C(=O)$—$R^{10}$, —$C(=O)$—O—$R^{10}$, —$SO_2R^{10}$, —$C(=NH)$—$NR^{11}R^{12}$ or —$C(=O)$—$NR^{11}R^{12}$, wherein $R^{10}$ is hydrogen, $C_{1-6}$ alkyl optionally substituted with halogen, amino, hydroxyl, $C_{1-6}$ alkyl, $C_{1-6}$ alkoxy or phenyl; benzyl, optionally substituted with halogen, amino, hydroxyl, $C_{1-6}$ alkyl, $C_{1-6}$ alkoxy or phenyl; or 3a,7a,12a-trihydroxy-5b-cholanyl, and $R^{11}$ and $R^{12}$ independently of each other are hydrogen, $C_{1-6}$ alkyl optionally substituted with halogen, amino, hydroxyl, $C_{1-6}$ alkyl, $C_{1-6}$ alkoxy or phenyl; or benzyl, optionally substituted with halogen, amino, hydroxyl, $C_{1-6}$ alkyl, $C_{1-6}$ alkoxy or phenyl, Q is hydrogen, $Q^1$, $Q^2$ or $Q^3$, wherein $Q^1$ is —$C(=O)$—$NHR^{13}$, $Q^2$ is —$C(=O)$—$NH_2$, and $Q^3$ is —$C(=O)$—$NR^{14}R^{15}$, wherein $R^{13}$, $R^{14}$ and $R^{15}$ independently of each other are $C_{1-6}$ alkyl optionally substituted with halogen, amino, hydroxyl, $C_{1-6}$ alkyl, $C_{1-6}$ alkoxy or phenyl;

or a pharmaceutically acceptable salt thereof;

with the proviso(s) that if M is $M^2$ then T cannot be hydrogen, $T^1$ or $T^2$, if T is hydrogen then Q cannot be hydrogen, if M is $M^1$ or $M^3$ then $R^4$ cannot be hydrogen, if M is $M^3$ and X is 2-naphthyl and Y is phenyl and T is $T^1$ then Q cannot be $Q^2$, if T is $T^2$ and n is 2 then $R^5$ cannot be hydrogen, if Q is $Q_3$ and Y is phenyl and X is 2-naphthyl and $R^3$, $R^4$ and $R^5$ are methyl, then M cannot be $M^1$, or if T is $T^2$ and n is 3 and Y is phenyl and X is 2-naphthyl and $R^3$, $R^4$ and $R^5$ are methyl, then M cannot be $M^1$.

In a more narrow aspect the present invention relates to a compound of general formula I (I)

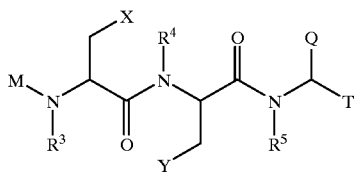

wherein $R^3$, $R^4$ and $R^5$ independently of each other are hydrogen, or $C_{1-6}$ alkyl optionally substitued with $C_{1-6}$ alkyl, X is aryl optionally substituted with halogen, $C_{1-6}$ alkyl or phenyl, Y is aryl or hetaryl optionally substituted with halogen, $C_{1-6}$ alkyl, $C_{1-6}$ alkoxy or phenyl, M is $M^1$, $M^2$, $M^3$, $M^4$ or $M^5$, wherein $M^1$ is —$C(=O)$—$CH=CH$—$(CH_2)_m$—C$(R^{16}R^{17})$—$N(R^1R^2)$, $M^2$ is —$C(=O)$—$CH((CH_2)_m$-hetaryl)—NH—$C(=O)$—C$(R^{16}R^7)$—$N(R^1R^2)$, wherein m is 1, 2 or 3, and $R^{16}$ and $R^{17}$ independently of each other are $C_{1-6}$ alkyl, optionally substituted with halogen, amino, hydroxyl, $C_{1-6}$ alkyl, $C_{1-6}$ alkoxy or phenyl;

$M^3$ is —$C(=O)$—$D^1$—$CH_2$—$N(R^1R^2)$, $M^4$ is —$C(=O)$—$D^1$—$C(R^6R^7)$—$N(R^1R^2)$, and $M^5$ is —$C(=O)$—$(CH_2)_s$—O—$(CH_2)_p$13 C$(R^6R^7)_q$—A, wherein $R^6$ and $R^7$ independently of each other are hydrogen, $C_{1-6}$ alkyl, $D^1$ is arylene, such as phenylene or naphthylene, preferably phenylene, p and s independently of each other are 1, 2 or 3, q is 0 or 1, and A is —$N(R^1R^2)$ or a saturated heterocyclic ring containing 5 or 6 ring members, one ring member being a heteroatom such as N, S and/or O, preferably N, wherein $R^1$ and $R^2$ independently of each other are hydrogen, —$C(=O)$—$C_{1-6}$ alkyl, $C_{1-6}$ alkyl optionally substituted with halogen, amino, hydroxyl, $C_{1-6}$ alkyl, $C_{1-6}$ alkoxy or phenyl; or benzyl, optionally substituted with halogen, amino, hydroxyl, $C_{1-6}$ alkyl, $C_{1-6}$ alkoxy or phenyl, T is hydrogen, $T^1$, $T^2$ or $T^3$, wherein $T^1$ is —$(CH_2)_n$—$NH_2$, wherein n is 1, 2, 3, 4, 5, 6, 7, 8, 9 or 10, $T^2$ is —$(CH_2)_n$—$N(R^8R^9)$, wherein n is 1, 2, 3, 4, 5, 6, 7, 8, 9 or 10, and $R^8$ and $R^9$ independently of each other are $C_{1-6}$ alkyl optionally substituted with halogen, amino, hydroxyl, $C_{1-6}$ alkyl, $C_{1-6}$ alkoxy or phenyl, or $R^8$ and $R^9$ may be joined to form a saturated heterocyclic ring containing 5 or 6 ring members, one of the ring members being N and the other being carbon atoms; and $T^3$ is —$(CH_2)_n$—NHZ, wherein n is 1, 2, 3, 4, 5, 6, 7, 8, 9 or 10, and Z is —$C(=O)$—$R^{10}$, —$C(=O)$—O—$R^{10}$, —$SO_2R^{10}$ or —$C(=O)$—$NR^{11}R^{12}$, wherein $R^{10}$ is hydrogen, $C_{1-6}$ alkyl optionally substituted with halogen, amino, hydroxyl, $C_{1-6}$ alkyl, $C_{1-6}$ alkoxy or phenyl; benzyl, optionally substituted with halogen, amino, hydroxyl, $C_{1-6}$ alkyl, $C_{1-6}$ alkoxy or phenyl; or 3a,7a,12a-trihydroxy-5b-cholanyl, and $R^{11}$ and $R^{12}$ independently of each other are hydrogen, $C_{1-6}$ alkyl optionally substituted with halogen, amino, hydroxyl, $C_{1-6}$ alkyl, $C_{1-6}$ alkoxy or phenyl; or benzyl, optionally substituted with halogen, amino, hydroxyl, $C_{1-6}$ alkyl, $C_{1-6}$ alkoxy or phenyl, Q is hydrogen, $Q^1$, $Q^2$ or $Q^3$, wherein $Q^1$ is —$C(=O)$—$NHR^{13}$, $Q^2$ is —$C(=O)$—$NH_2$, and $Q^3$ is —$C(=O)$—$NR^{14}R^{15}$, wherein $R^{13}$, $R^{14}$ and $R^{15}$ independently of each other are $C_{1-6}$ alkyl optionally substituted with halogen, amino, hydroxyl, $C_{1-6}$ alkyl, $C_{1-6}$ alkoxy or phenyl;

or a pharmaceutically acceptable salt thereof;

with the proviso(s) that if M is $M^2$ then T cannot be hydrogen, $T^1$ or $T^2$, if T is hydrogen then Q cannot be hydrogen, if M is $M^1$ or $M^3$ then $R^4$ cannot be hydrogen, if M is $M^3$ and X is 2-naphthyl and Y is phenyl and T is $T^1$ then Q cannot be $Q^2$, if T is $T^2$ and n is 2 then $R^5$ cannot be hydrogen, if Q is Q3 and Y is phenyl and X is 2-naphthyl and $R^3$, $R^4$ and $R^5$ are methyl, then M cannot be $M^1$, or if T is $T^2$ and n is 3 and Y is phenyl and X is 2-naphthyl and $R^3$, $R^4$ and $R^5$ are methyl, then M cannot be $M^1$.

The compounds of formula I comprise any optical isomers thereof, in the form of separated, pure or partially purified optical isomers or racemic mixtures thereof. For instance, whenever one or more chiral carbonatoms are present such chiral center(s) may be in the R- or S-configuration, or a mixture of R and S.

In one embodiment of the compound of the above formula I there is the following further proviso(s) that if M is $M^3$ and X is phenyl and Y is phenyl and T is $T^1$ then Q cannot be $Q^2$, if T is H and X is napthyl and Y is phenyl and $R_5$ is H then M cannot be $M^1$, or if n is 2 and Q is H and T is $T_2$ and X is napthyl and Y is phenyl then M cannot be $M_r$.

In one further embodiment of the compound of the above formula I $R^1$ and $R^2$ are independently of each other hydrogen, $C_{1-6}$alkyl, or —C(=O)—$C_{1-6}$alkyl, preferably hydrogen, methyl or —C(=O)—$CH_3$. In a particular embodiment $R^1$ and $R^2$ are both hydrogen or one is hydrogen and the other is methyl or —C(=O)—$C_{1-6}$ alkyl e.g. —C(=O)—$CH_3$. Especially preferred $R^1$ is hydrogen and $R^2$ is hydrogen, methyl or —C(=O)—$CH_3$.

In another embodiment of the compound of the above formula I M is hydrogen, —C(=O)—CH=CH—($CH_2$)—C($R^{16}R^{17}$)—N($R^1R^2$), —C(=O)—CH($CH_2$-hetaryl)—NH—C(=O)—C($R^{16}R^{17}$)—N($R^1R^2$), wherein $R^{16}$ and $R^{17}$ independently of each other are $C_{1-6}$ alkyl, optionally substituted with halogen, amino, hydroxyl, $C_{1-6}$ alkyl, $C_{1-6}$ alkoxy or phenyl; —C(=O)—$D^1$—C($R^6R^7$)—N($R^1R^2$), —C(=O)—$CH_2$—O—$CH_2$—C($R^6R^7$)—N($R^1R^2$) or —C(=O)—$CH_2$—O—$CH_2$—A, wherein $R^6$ and $R^7$ independently of each other are hydrogen or $C_{1-6}$ alkyl, A is a saturated heterocyclic ring containing 5 or 6 ring members, one ring member being a nitrogen atom, and $D^1$, $R^1$ and $R^2$ are as defined above. When M is —C(=O)—CH=CH—($CH_2$)—C($R^{16}R^{17}$)—N($R^1R^2$), it is in either cis or trans configuration, trans being preferred. When M is —C($R^{16}R^{17}$)—C(=O)—NH—CH($CH_2$-hetaryl)—C(=O)—N($R^1R^2$), hetaryl is preferably imidazolyl, which may be attached to the methylene group in any of the five positions, the 5-position being preferred. Moreover hetaryl is connected through a methylen group to a chiral carbonatom, the hetaryl-$CH_2$-moiety being in either R- or S-configuration, preferably S-configuration. In one embodiment of $M^1$ or $M^2$, $R^{16}$ and $R^{17}$ are independently of each other $C_{1-6}$ alkyl, preferably methyl, and in a particular embodiment $R^{16}$ and $R^{17}$ are both methyl. When M is —C(=O)—$D^1$—C($R^6R^7$)—N($R^1R^2$), $D^1$ is preferably phenylene, which may be attached to the carbonyl group through any of its five ring positions, the 3-position being preferred. In one embodiment of $M^4$, $R^6$ and $R^7$ are independently of each other hydrogen or $C_1$ alkyl, preferably hydrogen or methyl. When $R^6$ and $R^7$ are both hydrogen, then $M^4$ is $M^3$. In a particular embodiment $R^6$ and $R^7$ are both hydrogen or one is hydrogen and the other is $C.1_4$ alkyl, preferably methyl. When M is —C(=O)—$CH_2$—O—$CH_2$—C($R^6R^7$)—N($R^1R^2$), $R^6$ and $R^7$ are independently of each other hydrogen or $C_{1-6}$ alkyl, preferably hydrogen or ethyl. When M is —C(=O)—$CH_2$—O—$CH_2$—A, A is a saturated heterocyclic ring containing 5 ring members, one ring member being a nitrogen atom (N), and most preferred A is pyrrolidinyl, such as pyrrolidin-2-yl in the S-configuration. Especially preferred M is hydrogen, —C(=O)—CH=CH—$CH_2$—C($CH_3$)$_2$—$NH_2$ in trans configuration, —C(=O)—CH($CH_2$—(1H-imidazol-5-yl))—NH—C(=O)—C($CH_3$)$_2$—$NH_2$, —C(=O)—CH($CH_2$—(1H-imidazol-5-yl))—NH—C(=O)—C($CH_3$)$_2$—NH(C(=O)—$CH_3$), —C(=O)—(m-phenylene)—$CH_2$—$NH_2$, —C(=O)—(m-phenylene)—$CH_2$—NH—$CH_3$, —C(=O)—(m-phenylene)—$CH_2$—NH(C(=O)—$CH_3$), —C(=O)—(m-phenylene)—CH($CH_3$)—$NH_2$, —C(=O)—$CH_2$—O—$CH_2$—CH($CH_2CH_3$)—$NH_2$ or —C(=O)—$CH_2$—O—$CH_2$—((2S)-pyrrolidin-2-yl).

In a further embodiment of the compound of the above formula I $R^3$, $R^4$ and $R^5$ independently of each other are hydrogen or $C_{1-6}$ alkyl, preferably hydrogen or methyl. In a particular embodiment $R^3$ is methyl, $R^4$ is methyl and $R^5$ is methyl, or $R^3$ is methyl, $R^4$ is methyl and $R^5$ is hydrogen, or $R^3$ is hydrogen, $R^4$ is methyl and $R^5$ is hydrogen, or $R^3$ is hydrogen, $R^4$ is hydrogen and $R^5$ is hydrogen.

In a still further embodiment of the compound of the above formula I X is aryl optionally substituted with $C_{1-6}$ alkyl or phenyl. Preferably X is naphthyl, such as 1-naphthyl or 2-naphthyl, or phenyl substituted with $C_{1-6}$ alkyl or phenyl, preferably naphthyl or phenyl substituted with phenyl, which $C_{1-6}$ alkyl or phenyl may be attached to phenyl through any one of the five ring positions, the 4-position being preferred. Especially preferred X is 2-naphthyl or biphenyl-4-yl. Moreover, aryl, such as phenyl or naphthyl, is connected through a methylene group to a chiral carbonatom, the aryl-$CH_2$-moiety being in either R- or S-configuration, preferably R-configuration.

In a further embodiment of the compound of the above formula I Y is hetaryl or phenyl optionally substituted with halogen, such as chloro or fluoro. Preferably Y is phenyl optionally substituted with halogen, such as fluoro; or thienyl. When Y is thienyl it may be attached to the methylene group through any one of its four ring positions, the 2-position being preferred. Especially preferred Y is phenyl, 2-thienyl or 4-flouro-phenyl. Moreover, hetaryl or phenyl is connected through a methylene group to a chiral carbonatom, the (hetaryl or phenyl)-$CH_2$-moiety being in either R- or S-configuration, preferably R-configuration.

In a still further embodiment of the compound of the above formula I Q is hydrogen, —C(=O)—$NHR^{13}$, —C(=O)—$NH_2$ or —C(=O)—$NR^{14}R^{15}$, wherein $R^{13}$, $R^{14}$ and $R^{15}$ independently of each other are $C_{1-6}$ alkyl. When Q is —C(=O)—$NHR^{13}$, $R^{13}$ is preferably $C_{1-4}$ alkyl, such as methyl. When Q is —C(=O)—$NR^{14}R^{15}$, $R^{14}$ and $R^{15}$ are independently of each other preferably $C_{1-6}$ alkyl, and in particular methyl. Especially preferred Q is hydrogen, —C(=O)—NH—$CH_3$, —C(=O)—$NH_2$ or —C(=O)—N($CH_3$)$_2$.

In a further embodiment of the compound of the above formula I T is hydrogen, —($CH_2$)$_n$—$NH_2$, —($CH_2$)$_n$—N($R^8R^9$), wherein $R^8$ and $R^9$ independently of each other are $C_{1-6}$ alkyl or $R^8$ and $R^9$ are joined to form a saturated heterocyclic ring containing 5 ring members, one of the ring members being nitrogen and the other four being carbon atoms; or —($CH_2$)$_n$—NHZ, wherein n is 1, 2, 3, 4, 5 or 6, and Z is —C(=O)—$R^{10}$, —C(=O)—O—$R^{10}$, $SO_2R^{10}$, —C(=NH)—$NR^{11}R^{12}$ or —C(=O)—$NR^{11}R^{12}$, wherein $R^{10}$ is hydrogen, $C_{1-6}$ alkyl, benzyl or 3a,7a,12a-trihydroxy-5b-cholanyl, and $R^{11}$ and $R^{12}$ independently of each other are hydrogen, $C_{1-6}$ alkyl or benzyl. When T is —($CH_2$)$_n$—$NH_2$, n is preferably 1, 2, 3, 4 or 5. When T is —($CH_2$)$_n$—N($R^8R^9$), $R^8$ and $R^9$ are independently of each other $C_{1-4}$ alkyl, preferably methyl, and n is 1, 2, 3, 4, 5 or 6. In particular when T is $T^2$, n is 1, 2 or 3. When T is —($CH_2$)$_n$—NHZ, wherein n is 1, 2, 3, 4, 5 or 6, Z is —C(=O)—$R^{10}$, —C(=O)—O—$R^{10}$, $SO_2R^{10}$, wherein $R^{10}$ is $C_{1-6}$ alkyl, preferably $C_{1-6}$ alkyl such as methyl or t-butyl, 3a,7a,12a-trihydroxy-5b-cholanyl or benzyl; or —C(=O)—$NR^{11}R^{12}$, wherein $R^{11}$ and $R^{12}$ independently of each other are hydrogen or $C_{1-4}$ alkyl, preferably hydrogen or ethyl; or —C(=NH)—$NR^{11}R^{12}$, wherein $R^{11}$ and $R^{12}$ independently of each other are hydrogen or $C_{1-4}$ alkyl, preferably hydrogen. When T is —($CH_2$)$_n$—NHZ, n is preferably 1, 2, 3, 4 or 5, most preferred 3 or 4. Especially preferred T is hydrogen, —$CH_2$—$NH_2$, —($CH_2$)$_2$—$NH_2$, —($CH_2$)$_3$—$NH_2$, —($CH_2$)$_4$—$NH_2$, —($CH_2$)$_5$—$NH_2$, —$CH_2$—N($CH_3$)$_2$, —($CH_2$)$_2$—N($CH_3$)$_2$, —($CH_2$)$_3$—N($CH_3$)$_2$,—

(CH₂)₃—NH—C(=O)—NH₂, —(CH₂)₄—NH—C(=O)—CH₃, —(CH₂)₄—NHSO₂CH₃, —(CH₂)₄—NH—C(=NH)—NH₂, —(CH₂)₄—NH—C(=O)—NH—CH₂—CH₃, —(CH₂)₄—NH—C(=O)—O—t-butyl or —(CH₂)₄—NH—C(=O)—O—CH₂-phenyl. Moreover, T is connected to a carbon atom, which dependent on the remaining substituents may be in either R- or S-configuration, in which case the S-configuration is preferred.

Preferred compounds of the invention are:

3-Aminomethyl-N-((1R)-1-(((1R)-2-(2-thienyl)-1-((1S)-1-carbamoyl-5-aminopentylcarbamoyl)ethyl)-N-methylcarbamoyl)-2-(2-napthyl)ethyl)benzamide, 3-((1R/S)-1-Aminoethyl)-N-((1R)-1-{N-[(1R)-1-(N-(carbamoylmethyl)-N-methylcarbamoyl)-2-phenylethyl]-N-methylcarbamoyl}-2-(2-naphthyl)ethyl)-N-methylbenzamide, 2-Amino-N-(((1S)-1-(((1R)-1-(((1R)-1-(((1S)-1-carbamoyl-5-(methylsulfonylamino)pentyl)carbamoyl)-2-phenylethyl)carbamoyl)-2-(2-naphthyl)ethyl)carbamoyl)-2-(4-imidazolyl)ethyl)carbamoyl)-2-methylpropanamide, [(5S)-5-((2R)-2-{N-[(2R)-2-(3-(Aminomethyl)benzoylamino)-3-(2-naphthyl)propionyl}-N-methylamino}-3-(2-thienyl)propionylamino)-5-carbamoylpentyl]carbamic acid benzyl ester, N-((1R)-1-{N-[(1R)-1-(((1S)-5-Amino-1-carbamoylpentyl)carbamoyl)-2-(4-fluorophenyl)ethyl]-N-methylcarbamoyl}-2-(biphenyl-4-yl)ethyl)-3-aminomethylbenzamide, (2E)-5-Amino-5-methylhex-2-enoic acid N-((1R)-1-{N-[(1R)-1-(5-aminopentylcarbamoyl)-2-phenylethyl]-N-methylcarbamoyl}-2-(2-naphthyl)ethyl)-N-methylamide, 3-((1R/S)-1-Aminoethyl)-N-[(1R)-2-(biphenyl-4-yl)-1-(N-{(1R)-1-[N-(3-dimethylaminopropyl)-N-methylcarbamoyl]-2-phenylethyl}-N-methylcarbamoyl)ethyl]-N-methylbenzamide, (2E)-5-Amino-5-methylhex-2-enoic acid N-[(1R)-2-(biphenyl-4-yl)-1-(N-{(1R)-1-[N-(3-dimethylaminopropyl)-N-methylcarbamoyl]-2-phenylethyl}-N-methylcarbamoyl)ethyl]-N-methylamide, (2E)-5-Amino-5-methylhex-2-enoic acid N-((1R)-1-{N-[(1R)-1-((1S)-5-amino-1-carbamoylpentylcarbamoyl)-2-phenylethyl]-N-methylcarbamoyl}-2-(2-naphthyl)ethyl)-N-methylamide, N-((1R)-1-{N-[(1R)-1-((1S)-5-Amino-1-carbamoylpentylcarbamoyl)-2-phenylethyl]-N-methylcarbamoyl}-2-(2-naphthyl)ethyl)-3-((1R/S)-1-aminoethyl)-N-methylbenzamide, (2E)-5-Amino-5-methylhex-2-enoic acid ((1R)-1-{N-[(1R)-1-(((1S)-5-amino-1-(dimethylcarbamoyl)pentyl)carbamoyl)-2-phenylethyl]-N-methylcarbamoyl}-2-(2-naphthyl)ethyl)amide, N-((1R)-1-{N-[(1R)-1-(((1S)-5-Amino-1-(dimethylcarbamoyl)pentyl)carbamoyl)-2-phenylethyl]-N-methylcarbamoyl}-2-(biphenyl-4-yl)ethyl)-3-aminomethyl-N-methylbenzamide, (2E)-5-Amino-5-methyl-hex-2-enoic acid N-((1R)-1-{N-[(1R)-1-((1S)-5-amino-1-(dimethylcarbamoyl)pentylcarbamoyl)-2-phenylethyl]-N-methylcarbamoyl}-2-(biphenyl-4-yl)ethyl)-N-methylamide, N-((1R)-1-{[(1R)-1-(((1S)-5-Amino-1-carbamoylpentyl)carbamoyl)-2-(4-fluorophenyl)ethyl]-N-methylcarbamoyl}-2-(2-naphthyl)ethyl)-3-aminomethylbenzamide, (2E)-5-Amino-5-methylhex-2-enoic acid ((1R)-1-{N-[(1R)-1-(((5S)-5-amino-1-carbamoylpentyl)carbamoyl)-2-(4-fluorophenyl)ethyl]-N-methylcarbamoyl}-2-(2-naphthyl)ethyl)amide, N-((1R)-1-{N-[(1R)-1-(((1S)-5-Amino-1-carbamoylpentyl)carbamoyl)-2-(4-fluorophenyl)ethyl]-N-methylcarbamoyl}-2-(2-naphtyl)ethyl)-3-aminomethyl-N-methylbenzamide, (2S)-6-Amino-2-[(2R)-3-(4-fluorophenyl)-2-(N-methyl-N-{(2R)-3-(2-naphthyl)-2-[2-(((2S)-pyrrolidin-2-yl)methoxy)acetylamino]-propionylamino)propionylamino]hexanoic acid amide, (2S)-6-Amino-2-[(2R)-2-(N-{(2R)-2-[2-((2R/S)-2-aminobutoxy)acetylamino]-3-(2-naphthyl)propionyl}-N-methylamino)-3-(4-fluorophenyl)propionylamino]hexanoic acid amide, (2E)-5-Amino-5-methylhex-2-enoic acid N-((1R)-1-{N-[(1R)-1-(((1S)-5-amino-1-carbamoylpentyl)carbamoyl)-2-phenylethyl]-N-methylcarbamoyl}-2-(2-naphthyl)ethyl)amide, (2E)-5-Amino-5-methylhex-2-enoic acid N-((1R)-1-{N-[(1R)-1-(((1S)-5-amino-1-carbamoylpentyl)carbamoyl)-2-phenylethyl]-N-methylcarbamoyl}-2-(biphenyl-4-yl)ethyl}amide, N-((1R)-1-{N-[(1R)-1-(((1S)-5-Amino-1-carbamoylpentyl)carbamoyl)-2-phenylethyl]-N-methylcarbamoyl}-2-(biphenyl-4-yl)ethyl)-3-aminomethylbenzamide, (2E)-5-Amino-5-methylhex-2-enoic acid N-((1R)-1-{N-[(1R)-1-(((1S)-5-amino-1-carbamoylpentyl)carbamoyl)-2-(2-thienyl)ethyl]-N-methylcarbamoyl}-2-(2-naphthyl)ethyl}amide, 3-Aminomethyl-N-((1R)-1-(((1R)-2-(2-thienyl)-1-((1S)-1-carbamoyl-5-aminopentylcarbamoyl)ethyl)-N-methylcarbamoyl)-2-(2-napthyl)ethyl)benzamide, (2E)-5-Amino-5-methylhex-2-enoic acid N-((1R)-1-{N-[(1R)-1-(((1S)-5-amino-1-carbamoylpentyl)carbamoyl)-2-(2-thienyl)ethyl]-N-methylcarbamoyl}-2-(biphenyl-4-yl)ethyl}amide, N-((1R)-1-{N-[(1R)-1-(((1S)-5-Amino-1-carbamoylpentyl)carbamoyl)-2-(2-thienyl)ethyl]-N-methylcarbamoyl}-2-(biphenyl-4-yl)ethyl)-3-aminomethylbenzamide, (2E)-5-Amino-5-methylhex-2-enoic acid N-((1R)-1-{N-[(1R)-1-(((1S)-5-acetylamino-1-carbamoylpentyl)carbamoyl)-2-phenylethyl]-N-methylcarbamoyl}-2-(2-naphthyl)ethyl)amide (2E)-5-Amino-5-methylhex-2-enoic acid N-((1R)-1-{N-[(1R)-1-(((1S)-5-acetylamino-1-carbamoylpentyl)carbamoyl)-2-(2-thienyl)ethyl]-N-methylcarbamoyl}2-(biphenyl-4-yl)ethyl)amide, (2E)-5-Amino-5-methylhex-2-enoic acid N-((1R)-1-{N-[(1R)-1-(((1S)-5-acetylamino-1-carbamoylpentyl)carbamoyl)-2-phenylethyl]-N-methylcarbamoyl}-2-(biphenyl-4-yl)ethyl)amide, (2E)-5-Amino-5-methylhex-2-enoic acid N-((1R)-1-{N-[(1R)-1-((1S)-5-acetylamino-1-carbamoylpentylcarbamoyl)-2-(2-thienyl)ethyl]-N-methylcarbamoyl}-2-(2-naphthyl)ethyl}amide, (2)-5-Amino-5-methylhex-2-enoic acid N-((1R)-1-{N-[(1R)-1-(6-aminohexylcarbamoyl)-2-phenylethyl]-N-methylcarbamoyl}-2-(biphenyl-4-yl)ethyl)-N-methylamide, (2E)-5-Amino-5-methylhex-2-enoic acid N-((1R)-1-{N-[(1R)-1-(4-aminobutylcarbamoyl)-2-phenylethyl]-N-methylcarbamoyl}-2-(biphenyl-4-yl)ethyl)-N-methylamide, (2E)-5-Amino-5-methylhex-2-enoic acid N-((1R)-1-{N-[(1R)-1-(3-aminopropylcarbamoyl)-2-phenylethyl]-N-methylcarbamoyl}-2-(biphenyl-4-yl)ethyl)-N-methylamide, (2E)-5-Amino-5-methylhex-2-enoic acid N-((1R)-1-{N-[(1R)-1-(2-aminoethylcarbamoyl)-2-phenylethyl]-N-methylcarbamoyl}-2-(biphenyl-4-yl)ethyl)-N-methylamide, 3-(1-Aminoethyl)-N-((1R)-1-(N-((1R)-1-(N-(3-imethylaminopropyl)-N-methylcarbamoyl)-2-phenylethyl)-N-methylcarbamoyl)-2-(2-naphthyl)ethyl)-N-methylbenzamide, 3-(1-Aminoethyl)-N-((1R)-1-(N-((1R)-1-(N-((dimethylcarbamoyl)methyl)-N-methylcarbamoyl)-2-phenylethyl)-N-methylcarbamoyl)-2-(2-naphthyl)ethyl)-N-methylbenzamide, (2S)-6-Acetylamino-2-((2R)-2-{(2R)-2-[(2S)-2-(2-amino-2-methylpropionylamino)-3-(imidazol-4-yl)propionylamino]-3-(2-naphthyl)propionylamino}-3-phenylpropionylamino)hexanoic acid amide, (2S)-5-Ureido-2-((2R)-2-{(2R)-2-[(2S)-2-(2-amino-2-methylpropionylamino)-3-(3H-imidazol-4-yl)propionylamino]-3-(2-naphthyl)propionylamino}-3-phenylpropionylamino)pentanoic acid amide, (2S)-6-tert Butyloxycarbonylamino-2-((2R)-2-{(2R)-2-[(2S)-2-(2-amino-2-methylpropionylamino)-3-(imidazol-4-yl)propionylamino]-3-(2-naphthyl)propionylamino}-3-phenylpropionylamino)hexanoic acid amide, (2S)-6-Acetylamino-2-((2R)-2-{N-((2R)-2-[(2S)-2-(2-amino-2-methylpropionylamino)-3-(imidazol-4-yl)propionylamino]-3-(2-naphthyl)propionyl)-N-methylamino}-3-phenylpropionylamino)hexanoic acid amide, (2S)-6-(3a,7a, 1 2a-trihydroxy-5b-cholanoylamino)-2-((2R)-2-{(2R)-2-[(2S)-2-(2-amino-2-methylpropionylamino)-3-(3H-imidazol-4-yl)propionylamino]-3-(2-naphthyl)propionylamino}-3-phenylpropionylamino)hexanoic acid amide, (2E)-5-Amino-5-methylhex-2-enoic acid ((1R)-1-{N-[(1R)-1-(5-aminopentylcarbamoyl)-2-phenylethyl]-N-methylcarbamoyl}-2-(2-naphthyl)ethyl)amide, (2E)-5-Amino-5-methylhex-2-enoic acid N-((1R)-1-{N-[(1R)-1-(5-aminopentylcarbamoyl)-2-phenylethyl]-N-methylcarbamoyl}-2-(2-naphthyl)ethyl)-N-methylamide, N-((1R)-1-{N-[(1R)-1-(4-Aminobutylcarbamoyl)-2-phenylethyl]-N-methylcarbamoyl}-2-(biphenyl-4-yl)ethyl)-3-aminomethyl-N-methylbenzamide, 3-Aminomethyl-N-({1 R}-1-{N-[(1R)-1-(5-aminopentylcarbamoyl)-2-phenylethyl]-N-methylcarbamoyl}-2-(2-naphthyl)ethyl)benzamide, 3-Aminomethyl-N-((1R)-1-{N-[(1R)-1-(5-aminopentylcarbamoyl)-2-phenylethyl]-N-methylcarbamoyl}-2-(2-naphthyl)ethyl)-N-methylbenzamide, (2E)-5-Amino-5-methylhex-2-enoic acid N-((1R)-1-{N-[(1R)-1-((4-dimethylaminobutyl)carbamoyl)-2-phenylethyl]-N-methylcarbamoyl}-2-(2-naphthyl)ethyl)-N-methylamide, (2E)-5-Amino-5-methylhex-2-enoic acid N-((1R)-1-{N-[(1R)-1-(5-guanidinopentylcarbamoyl)-2-phenylethyl]-N-methylcarbamoyl}-2-(2-naphthyl)ethyl)-N-methylamide, (2E)-5-Amino-5-methylhex-2-enoic acid N-[(1R)-1-(N-{(1R)-1-[5-(3-ethylureido)pentylcarbamoyl]-2-phenylethyl}-N-methylcarbamoyl)-2-(2-naphthyl)ethyl]-N-methylamide, 3-Aminomethyl-N-[(1R)-1-(N-{(1R)-1-[N-(2-(dimethylamino)ethyl)-N-methylcarbamoyl]-2-phenylethyl}-N-methylcarbamoyl)-2-(2-naphthyl)ethyl]-N-methylbenzamide, N-[(1R)-1-(N-{(1R)-1-[N-(2-(Dimethylamino)ethyl)-N-methylcarbamoyl]-2-phenylethyl}-N-methylcarbamoyl)-2-(2-naphthyl)ethyl]-N-methyl-3-(methylaminomethyl)benzamide, 3-((1R/S)-1-Aminoethyl)-N-[(1R)-1-(N-{(1R)-1-[N-(2-(dimethylamino)ethyl)-N-methylcarbamoyl]-2-phenylethyl}-N-methylcarbamoyl)-2-(2-naphthyl)ethyl]-N-methylbenzamide, (2E)-5-Amino-5-methylhex-2-enoic acid N-((1R)-2-(biphenyl-4-yl)-1-{N-[(1R)-1-(4-(dimethylamino)butylcarbamoyl)-2-phenylethyl]-N-methylcarbamoyl}ethyl)-N-methylamide, (2E)-5-Amino-5-methylhex-2-enoic acid N-[(1R)-1-(N-{(1R)-1-[N-(2-dimethylaminoethyl)-N-methylcarbamoyl]-2-phenylethyl}-N-methylcarbamoyl)-2-(2-naphthyl)ethyl]-N-methylamide, (2E)-5-Amino-5-methylhex-2-enoic acid N-((1R)-1-{N-[(1R)-1-((4-dimethylaminobutyl)carbamoyl)-2-(2-thienyl)ethyl]-N-methylcarbamoyl}-2-(2-naphthyl)ethyl)-N-methylamide, (2E)-5-Amino-5-methylhex-2-enoic acid N-((1R)-2-(4-biphenyl-4-yl)-1-{N-[(1R)-1-((4-dimethylaminobutyl)carbamoyl)-2-(2-thienyl)ethyl]-N-methylcarbamoyl}ethyl)-N-methylamide, (2E)-5-Amino-5-methylhex-2-enoic acid N-((1R)-1-{N-[(1R)-1-((1S)-5-(acetylamino)-1-(dimethylcarbamoyl)pentylcarbamoyl)-2-phenylethyl]-N-methylcarbamoyl}-2-(2-naphthyl)ethyl)-N-methylamide, and (2E)-5-Amino-5-methylhex-2-enoic acid N-((1R)-1-{N-[(1R)-1-((1S)-5-acetylamino-1-(methylcarbamoyl)pentylcarbamoyl)-2-phenylethyl]-N-methylcarbamoyl}-2-(2-naphthyl)ethyl)-N-methylamide.

The compounds of formula I exhibit an improved resistance to proteolytic degradation by enzymes compared to that of the peptides suggested in the prior literature, due to the lack of natural peptide bonds. The increased resistance to proteolytic degradation of the compounds of the invention in comparison with known growth hormone releasing peptides is expected to improve their bioavailability compared to that of the peptides suggested in the prior literature.

In the above structural formulas and throughout the present specification, the following terms have the indicated meanings:

The $C_{1-6}$-alkyl, $C_{1-6}$-alkylene, $C_{1-4}$-alkyl or $C_{1-4}$-alkylene groups specified above are intended to include those alkyl or alkylene groups of the designated length in either a linear or branched or cyclic configuration. Examples of linear alkyl are methyl, ethyl, propyl, butyl, pentyl, and hexyl and their corresponding divalent moieties, such as ethylene. Examples of branched alkyl are isopropyl, sec-butyl, tert-butyl, isopentyl, and isohexyl and their corresponding divalent moieties, such as isopropylene. Examples of cyclic alkyl are $C_{3-6}$-cycloalkyl such as cyclopropyl, cyclobutyl, cyclopentyl and cyclohexyl and their corresponding divalent moieties, such as cyclopropylene.

The $C_{1-6}$-alkoxy groups specified above are intended to include those alkoxy groups of the designated length in either a linear or branched or cyclic configuration. Examples of linear alkoxy are methoxy, ethoxy, propoxy, butoxy, pentoxy, and hexoxy. Examples of branched alkoxy are isopropoxy, sec-butoxy, tert-butoxy, isopentoxy, and isohexoxy. Examples of cyclic alkoxy are cyclopropyloxy, cyclobutyloxy, cyclopentyloxy and cyclohexyloxy.

In the present context, the term "aryl" is intended to include monovalent carbocyclic aromatic ring moieties, being either monocyclic, bicyclic or polycyclic, e.g. selected from the group consisting of phenyl and naphthyl, optionally substituted with one or more $C_{1-6}$-alkyl, $C_{1-6}$-alkoxy, halogen, amino or aryl.

In the present context, the term "arylene" is intended to include divalent carbocyclic aromatic ring moieties, being either monocyclic, bicyclic or polycyclic, e.g. selected from the group consisting of phenylene and naphthylene, optionally substituted with one or more $C_{1-6}$-alkyl, $C_{1-6}$-alkoxy, halogen, amino or aryl.

In the present context, the term "hetaryl" is intended to include monovalent heterocyclic aromatic ring moieties, being either monocyclic, bicyclic or polycyclic, e.g. selected from the group consisting of pyridyl, 1-H-tetrazol-5-yl, thiazolyl, imidazolyl, indolyl, pyrimidinyl, thiadiazolyl, pyrazolyl, oxazolyl, isoxazolyl, oxadiazolyl, thienyl, quinolinyl, pyrazinyl, or isothiazolyl, optionally substituted by one or more $C_{1-6}$-alkyl, $C_{1-6}$-alkoxy, halogen, amino or aryl.

In the present context, the term "hetarylene" is intended to include divalent heterocyclic aromatic ring moieties, being either monocyclic, bicyclic or polycyclic, e.g. selected from the group consisting of pyridinediyl, 1-H-tetrazolediyl, thiazoldiyl, imidazolediyl, indolediyl, pyrimidinediyl, thiadiazolediyl, pyrazolediyl, oxazolediyl, isoxazolediyl, oxadiazolediyl, thiophenediyl, quinolinediyl, pyrazinediyl, or isothiazolediyl, optionally substituted by one or more $C_{1-6}$-alkyl, $C_{1-6}$-alkoxy, halogen, amino or aryl.

The term "halogen" is intended to include chlorine (Cl), fluorine (F), bromine (Br) and iodine (I).

The compounds of the present invention may have one or more asymmetric centres and it is intended that stereoisomers, as separated, pure or partially purified stereoisomers or racemic mixtures thereof are included in the scope of the invention.

The compounds of the present invention may optionally be on a pharmaceutically acceptable salt form such as the pharmaceutically acceptable acid addition salts of compounds of formula I which include those prepared by reacting the compound of formula I with an inorganic or organic acid such as hydrochloric, hydrobromic, sulfuric, acetic, phosphoric, lactic, maleic, mandelic phthalic, citric, glutaric, gluconic, methanesulfonic, salicylic, succinic, tartaric, toluenesulfonic, trifluoroacetic, sulfamic or fumaric acid. The compounds of formula I may be administered in pharmaceutically acceptable acid addition salt form or, where appropriate, as a alkali metal or alkaline earth metal or lower alkylammonium salt. Such salt forms are believed to exhibit approximately the same order of activity as the free base forms.

In another aspect, the present invention relates to a pharmaceutical composition comprising, as an active ingredient, a compound of the general formula I or a pharmaceutically acceptable salt thereof together with a pharmaceutically acceptable carrier or diluent.

Pharmaceutical compositions containing a compound of the present invention may be prepared by conventional techniques, e.g. as described in *Remington's Pharmaceutical Sciences,* 1985 or in Remington: The Science and Practice of Pharmacy, 19th Edition (1995). The compositions may appear in conventional forms, for example capsules, tablets, aerosols, solutions, suspensions or topical applications.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water.

Similarly, the carrier or diluent may include any sustained release material known in the art, such as glyceryl monostearate or glyceryl distearate, alone or mixed with a wax.

If a solid carrier is used for oral administration, the preparation may be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

A typical tablet which may be prepared by conventional tabletting techniques may contain:

Core:

| | |
|---|---|
| Active compound (as free compound or salt thereof) | 100 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | |
| Coating: | |
| HPMC approx. | 9 mg |
| *Mywacett 9-40 T approx. | 0.9 mg |

*Acylated monoglyceride used as plasticizer for film coating.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

Generally, the compounds of the present invention are dispensed in unit dosage form comprising 50–200 mg of active ingredient together with a pharmaceutically acceptable carrier per unit dosage.

It has been demonstrated that compounds of the general formula I possess the ability to release endogenous growth hormone in vivo. The compounds may therefore be used in the treatment of conditions which require increased plasma growth hormone levels such as in growth hormone deficient humans or in elderly patients or livestock.

Thus, in a particular aspect, the present invention relates to a pharmaceutical composition for stimulating the release of growth hormone from the pituitary, the composition comprising, as an active ingredient, a compound of the general formula I or a pharmaceutically acceptable salt thereof together with a pharmaceutically acceptable carrier or diluent.

In a further aspect, the present invention relates to a method of stimulating the release of growth hormone from the pituitary, the method comprising administering to a subject in need thereof an effective amount of a compound of the general formula I or a pharmaceutically acceptable salt thereof.

In a still further aspect, the present invention relates to the use of a compound of the general formula I or a pharmaceutically acceptable salt thereof for the preparation of a medicament for stimulating the release of growth hormone from the pituitary.

To those skilled in the art, it is well known that the current and potential uses of growth hormone in humans are varied and multitudinous. Thus, compounds of formula I can be administered for purposes stimulating release of growth hormone from the pituitary and would then have similar effects or uses as growth hormone itself. The uses of growth hormone may be summarized as follows: stimulation of growth hormone release in the elderly, prevention of catabolic side effects of glucocorticoids, prevention and treatment of osteoporosis, treatment of chronic fatigue syndrom (CFS), treatment of acute fatigue syndrom and muscle loss following election surgery, stimulation of the immune system, acceleration of wound healing, accelerating bone fracture repair, accelerating complicated fractures, e.g. disctraction osteogenesis, treatment of wasting secondary to fractures, treatment of growth retardation, treating growth retardation resulting from renal failure or insufficiency, treatment of cardiomyopathy, treatment of chronic liver disease, treatment of thrombocytopenia, treatment of Crohn's disease, treatment of short bowel syndrome, treatment of chronic obstructive pulmonary disease (COPD), treatment of complications associated with transplantation, treatment of physiological short stature including growth hormone deficient children and short stature associated with chronic illness, treatment of obesity and growth retardation associated with obesity, treatment of anorexia, treating growth retardation associated with the Prader-Willi syndrome and Turner's syndrome; accelerating the recovery and reducing hospitalization of bum patients; treatment of intrauterine growth retardation, skeletal dysplasia, hypercortisolism and Cushing's syndrome; induction of pulsatile growth hormone release; replacement of growth hormone in stressed patients, treatment of osteochondrodysplasias, Noonan's syndrome, schizophrenia, depressions, Alzheimer's disease, delayed wound healing and psychosocial deprivation, treatment of pulmonary dysfunction and ventilator dependency, attenuation of protein catabolic responses after major surgery, reducing cachexia and protein loss due to chronic illness such as cancer or AIDS; treatment of hyperinsulinemia including nesidioblastosis, adjuvant treatment for ovulation induction; to stimulate thymic development and prevent the age-related decline of thymic function, treatment of immunosuppressed patients, improvement in muscle strength, mobility, maintenance of skin thickness, metabolic homeostasis, renal homeostasis in the frail elderly, stimulation of osteoblasts, bone remodelling and cartilage growth, stimulation of the immune system in companion animals and treatment of disorder of aging in companion animals, growth promoter in livestock and stimulation of wool growth in sheep, and treatment of metabolic syndrom (syndromex). Moreover the compounds of formula I may be used in the treatment of insulin resistance, including NIDDM, in mammals, e.g. humans. It is furthermore believed that the present compounds of formula I may improve sleep quality and correct the relative hyposomatotropism of senescence due to high increase in REM sleep and a decrease in REM latency.

For the above indications the dosage will vary depending on the compound of formula I employed, on the mode of administration and on the therapy desired. An effective amount of the compounds according to this invention will depend, in part, on the particular condition to be treated, age, weight, and general health of the patient, and other factors evident to those skilled in the art. However, generally dosage levels between 0.0001 and 100 mg/kg body weight daily are administered to patients and animals to obtain effective release of endogenous growth hormone. Morever the compounds of formula I have no or substantially no side-effects, when administered in the above dosage levels, such side-effects being e.g. release of cortisol, LH and/or prolactin. Usually, dosage forms suitable for oral, nasal, pulmonal or transdermal administration comprise from about 0.0001 mg to about 100 mg, preferably from about 0.001 mg to about 50 mg of the compounds of formula I admixed with a pharmaceutically acceptable carrier or diluent.

Optionally, the pharmaceutical composition of the invention may comprise a compound of formula I combined with one or more compounds exhibiting a different activity, e.g., an antibiotic or other pharmacologically active material.

The route of administration may be any route which effectively transports the active compound to the appropriate or desired site of action, such as oral, nasal, pulmonary, transdermal or parenteral, the oral route being preferred.

Apart from the pharmaceutical use of the compounds of formula 1, they may be useful in vitro tools for investigating the regulation of growth hormone release.

Compounds of formula I may also be useful in vivo tools for evaluating the growth hormone releasing capability of the pituitary. For example, serum samples taken before and after administration of these compounds to humans can be assayed for growth hormone. Comparison of the growth hormone in each serum sample would directly determine the ability of the patients pituitary to release growth hormone.

Compounds of formula I may be administered to commercially important animals to increase their rate and extent of growth, and to increase milk production.

A further use of growth hormone secretagogue compounds of formula I is in combination with other secretagogues such as GHRP (2 or 6), GHRH and its analogues, growth hormone and its analogues or somatomedins including IGF-1 and IGF-2.

Pharmacological Methods

Compounds of formula I may be evaluated in vitro for their efficacy and potency to release growth hormone in rat pituitary primary cultures, and such evaluation may be performed as described below.

The isolation of rat pituitary cells is a modification of 0. Sartor et al., *Endocrinology* 116, 1985, pp. 952–957. Male albino Sprague-Dawley rats (250+/−25 grams) were purchased from Møllegaard, Lille Skensved, Denmark. The rats were housed in group cages (four animals/cage) and placed in rooms with 12 hour light cycle. The room temperature varied from 19–24° C. and the humidity from 30–60%.

The rats were decapitated and the pituitaries dissected. The neurointermediate lobes were removed and the remaining tissue was immediately placed in icecold isolation buffer (Gey's medium (Gibco 041-04030) supplemented with 0.25% D-glucose, 2% non-essential amino acids (Gibco 043-01140) and 1% bovine serum albumine (BSA) (Sigma A-4503)). The tissue was cut into small pieces and transferred to isolation buffer supplemented with 3.8 mg/ml of trypsin (Worthington #3707 TRL-3) and 330 mg/ml of DNase (Sigma D4527). This mixture was incubated at 70 rotations/min for 35 min at 37° C. in a 95/5% atmosphere of $O_2/CO_2$. The tissue was then washed three times in the above buffer. Using a standard pasteur pipette, the tissue was then aspirated into single cells. After dispersion, cells were filtered through a nylon filter (160 mm) to remove undigested tissue. The cell suspension was washed 3 times with isolation buffer supplemented with trypsin inhibitor (0.75 mg/ml, Worthington #2829) and finally resuspended in culture medium; DMEM (Gibco 041-01965) supplemented with 25 mM HEPES (Sigma H-3375), 4 mM glutamine (Gibco 043-05030H), 0.075% sodium bicarbonate (Sigma S-8875), 0.1% non-essential amino acid, 2.5% fetal calf serum (FCS, Gibco 011-06290), 3% horse serum (Gibco 034-06050), 10% fresh rat serum, 1 nM $T_3$ (Sigma T-2752) and 40 mg/l dexamethasone (Sigma D4902) pH 7.3, to a density of $2 \times 10^5$ cells/ml. The cells were seeded into microtiter plates (Nunc, Denmark), 200 ml/well, and cultured for 3 days at 37° C. and 8% $CO_2$.

Compound testing

After culturing, the cells were washed twice with stimulation buffer (Hanks Balanced Salt Solution (Gibco 041-

04020) supplemented with 1% BSA (Sigma A4503), 0.25% D-glucose (Sigma G-5250) and 25 mM HEPES (Sigma H-3375) pH 7.3) and preincubated for 1 hour at 37° C. The buffer was exchanged with 90 ml stimulation buffer (37° C.). Ten ml test compound solution was added and the plates were incubated for 15 min at 37° C. and 5% $CO_2$. The medium was decanted and analyzed for GH content in an rGH SPA test system.

All compounds were tested in doses ranging from 10 pM to 100 mM. A dose-response relation was constructed using the Hill equation (Fig P, Biosoft). The efficacy (maximal GH released, $E_{max}$) was expressed in % of the $E_{max}$ of GHRP-6. The potency ($EC_{50}$) was determined as the concentration inducing half maximal stimulation of the GH release.

Compounds of formula I may be evaluated for their metabolic stability using the procedure described below:

Compounds is dissolved at a concentration of 1 mg/ml in water. 25 ml of this solution is added to 175 ml of the respective enzyme-solution (resulting in an enzyme:substrate ratio (w/w) of approximately 1:5). The solution is left at 37° C. overnight. 10 ml of the various degradation solutions is analyzed against a corresponding zero-sample using flow injection electrospray mass spectrometry (ESMS) with selected ion monitoring of the molecular ion. If the signal has decreased more than 20% compared to the zero-sample, the remainder of the solution is analyzed by HPLC and mass spectrometry in order to identify the extent and site(s) of degradation precisely.

Several standard peptides (ACTH 4-10, Angiotensin 1-14 and Glucagon) have been included in the stability tests in order to verify the ability of the various solutions to degrade peptides.

Standard peptides (angiotensin 1-14, ACTH 4-10 and glucagon) were purchased from Sigma, Mo., USA) Enzymes (trypsin, chymotrypsin, elastase aminopeptidase M and carboxypeptidase Y and B) were all purchased from Boehringer Mannheim GmbH (Mannheim, Germany)

Pancreatic enzyme mix: trypsin, chymotrypsin and elastase in 100 mM ammoniumbicarbonate pH 8.0 (all concentrations 0.025 mg/ml).

Carboxypeptidase mix: carboxypeptidase Y and B in 50 mM ammoniumacetate pH 4.5 (all concentrations 0.025 mg/ml).

Aminopeptidase M solution: aminopeptidase M (0.025 mg/ml) in 100 mM ammoniumbicarbonate pH 8.0

Mass spectrometric analysis was performed using two different mass spectrometers. A Sciex API III triple quadrupole LC-MS instrument (Sciex instruments, Thornhill, Ontario) equipped with an electrospray ion-source and a Bio-Ion 20 time-of-flight Plasma Desorption instrument (Bio-Ion Nordic AB, Uppsala, Sweden).

Quantification of the compounds (before and after degradation) was done on the API III instrument using single ion monitoring of the molecular ion in question with flow injection of the analyte. The liquid flow (MeOH:water 1:1) of 100 ml/min was controlled by an ABI 140B HPLC unit (Perkin-Elmer Applied Biosystems Divisions, Foster City, Calif.). The instrument parameters were set to standard operation conditions, and SIM monitoring was performed using the most intense molecular ion (in most cases this corresponded to the doubly charged molecular ion). Identification of degradation products furthermore involved the use of plasma desorption mass spectrometry (PDMS) with sample application on nitrocellulose coated targets and standard instrumental settings. The accuracy of the hereby determined masses is generally better than 0.1%.

Separation and isolation of degradation products was done using a HY-TACH C-18 reverse phase 4.6×105 mm HPLC column (Hewlett-Packard Company, Palo Alto, Calif.) with a standard acetonitril: TFA separation gradient. The HPLC system used was HP1090M (Hewlett-Packard Company, Palo Alto, Calif.).

| Peptide derivative | MW/SIM ion (amu) | Carboxypeptidase mix | Pan. enzyme mix |
| --- | --- | --- | --- |
| Standards | | | |
| ACTH 4-10 | 1124.5/562.8 | + | − |
| Glucagon | 3483/871.8 | − | − |
| Insulin (B23-29) | 859.1/430.6 | | |
| Angiotensin 1-14 | 1760.1/881.0 | − | − |
| GHRP-2 | 817.4/409.6 | − | − |
| GHRP-6 | 872.6/437.4 | − | − |

+: Stable (less than 20% decrease in SIM signal after 24 h in degradation solution)
−: Unstable (more than 20% decrease in SIM signal after 24 h in degradation solution)

Any novel feature or combination of features described herein is considered essential to this invention.

EXAMPLES

The process for preparing compounds of formula I and preparations containing them is further illustrated in the following examples, which however, are not to be construed as limiting.

The structures of the compounds are confirmed by either elemental analysis (MA) nuclear magnetic resonance (NMR) or mass spectrometry (MS). NMR shifts (d) are given in parts per million (ppm) and only selected peaks are given. mp is melting point and is given in ° C. Column chromatography was carried out using the technique described by W. C. Still et al, J. Org. Chem. 1978, 43, 2923–2925 on Merck silica gel 60 (Art 9385). Compounds used as starting materials are either known compounds or compounds which can readily be prepared by methods known per se.

HPLC-Analysis:
Method A.

The RP-HPLC analysis was performed using UV detection at 214 nm and a Hibar LiChrosorb RP-18 (5 uM) 250-4 (Merck) column, which was eluted at 1 ml/minute. Two solvent systems were used:

Solvent system I: 0.1% Trifluoroacetic acid in acetonitrile.
Solvent system II: 0.1% Trifluoroacetic acid in water.

The column was equilibrated with a mixture composed of 20% of solvent system I and 95% of solvent system II. After injection of the sample a gradient of 20% to 80% of solvent system I in solvent system II was run over 30 minutes. The gradient was then extended to 100% of solvent system I over 5 minutes followed by isocratic elution with 100% of this system for 5 minutes.

Method A1.

The RP-analysis was performed using UV detections at 214, 254, 276, and 301 nm on a 218TP54 4.6 mm×250 mm 5 m C-18 silica column (The Seperations Group, Hesperia), which was eluted at 1 mL/min at 42° C. The column was equilibrated with 5% acetonitrile in a buffer consisting of 0.1 M ammonium sulfate, which was adjusted to pH 2.5 with 4M sulfuric acid. after injection the sample was eluted by a gradient of 5% to 60% acetonitrile in the same buffer during 50 min.

Method B1.

The RP-analysis was performed using UV detections at 214, 254, 276, and 301 nm on a 218TP54 4.6 mm×250 mm 5m C-18 silica column (The Seperations Group, Hesperia), which was eluted at 1 mL/min at 42° C. The column was equilibrated with 5% (acetonitrile+0.1% TFA) in an aqueous solution of TFA in water (0.1%). After injection the sample was eluted by a gradient of 5% to 60% (acetonitrile+0.1% TFA) in the same aqueous buffer during 50 min.

Abbrevations:
TLC: thin layer chromatography
DMSO: dimethylsulfoxide
min: minutes
h: hours
Troc: 2,2,2-trichloroethoxycarbonyl
Boc: tert butyloxycarbonyl
Z: benzyloxycarbonyl
OSu: N-oxysuccinimide
Lys: lysine
DMF: dimethylformamide
THF: tetrahydrofuran
EDAC: N-ethyl-N'-dimethylaminopropylcarbodiimide hydrochloride
HOBt: 1-hydroxybenzotriazole hydrate
HOAt: 1-hydroxy-7-azabenzotriazole
DIEA: diisopropylethylamine
TFA: trifluoroacetic acid Buildingblocks:

Throughout the following examples some common buildingblocks were used for which abbreviations, references and representative experimental details are given below.

N-methylated aminoacids used in the following examples were prepared as in Can. J. Chem. 1977, 55, 906.

Starting material of type buildingblock 1:

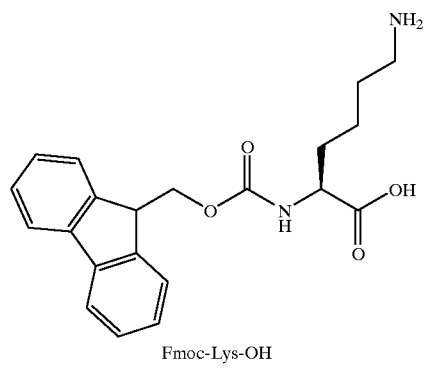

Fmoc-Lys-OH

Starting material of type buildingblock 2:

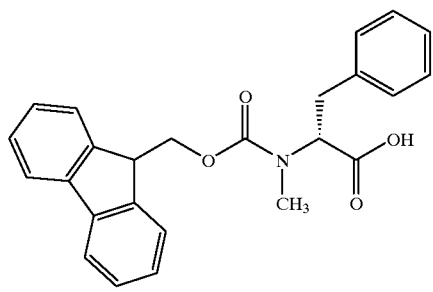

Fmoc-NMe-D-Phe-OH

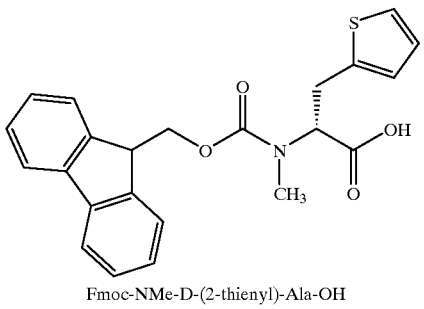

Fmoc-NMe-D-(2-thienyl)-Ala-OH

Starting material of type buildingblock 3:

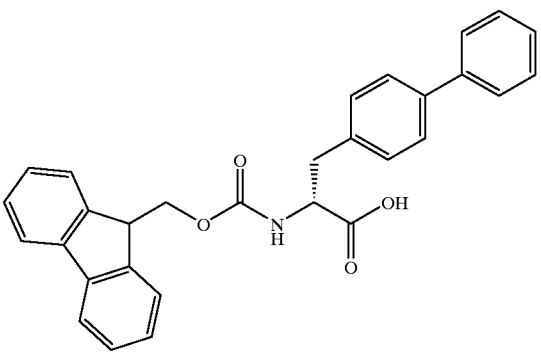

Fmoc-D-(4-biphenyl)-Ala-OH

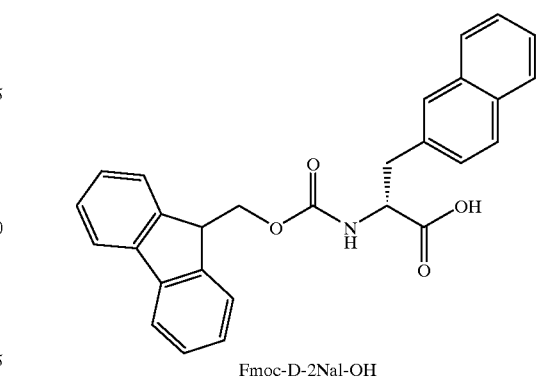

Fmoc-D-2Nal-OH

Starting material of type buildingblock 4:

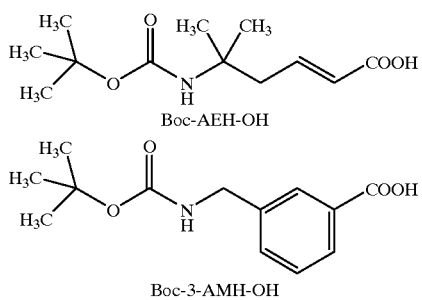

Boc-AEH-OH

Boc-3-AMH-OH

Synthesis of intermediates (buildingblocks):

Buildingblock Boc-AEH-OH:

(2E)-5-(tert-Butoxycarbonylamino)-5-methylhex-2-enoic acid:

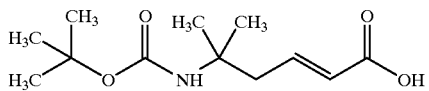

3-Hydroxy-1,1-dimethylpropylcarbamic acid tert-butyl ester:

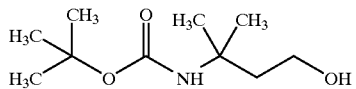

Step A: At 0° C., ethyl chloroformate (1.10 mL, 11.5 mmol) was given dropwise to a solution of 3-tert-butoxycarbonylamino-3-methylbutanoic acid (2.50 g, 11.5 mmol) and triethylamine (1.92 mL, 13.8 mmol) in tetrahydrofuran (10 mL). The solution was stirred for 40 min at 0° C. The formed precipitate was filtered off and washed with tetrahydrofuran (20 mL). The liquid was immediately cooled to 0° C. A 2M solution of lithium boronhydride in tetrahydrofuran (14.4 mL, 28.8 mmol) was added dropwise. The solution was stirred at 0° C. for 2 h, and then warmed to room temperature. over a period of 4 h. It was cooled to 0° C. Methanol (5 mL) was added carefully. 1 N Hydrochloric acid (100 mL) was added. The solution was extracted with ethyl acetate (2×100 mL, 3×50 mL). The combined organic layers were washed with saturated sodium hydrogen carbonate solution (100 mL) and dried over magnesium sulfate. The solvent was removed in vacuo. The crude product was chromatographed on silica (110 g) with ethyl acetate/heptane 1:2 to give 1.84 g of 3-hydroxy-1,1-dimethylpropylcarbamic acid tert-butyl ester.

$^1$H-NMR ((CDCl$_3$): d 1.33 (s, 6H); 1.44 (s, 9H); 1.88 (t, 2H); 1.94 (br, 1H); 3.75 (q, 2H); 4.98 (br, 1H).

3-(tert-Butoxycarbonylamino)-3-methylbutanal:

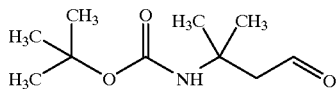

Step B: DMSO (1.22 mL, 17.2 mmol) was added to a solution of oxalyl chloride (1.1 mL, 12.9 mmol) at −78° C. in dichloromethane (15 mL). The mixture was stirred for 15 min at −78° C. A solution of 3-hydroxy-1,1-dimethylpropylcarbamic acid tert-butyl ester (1.75 g, 8.6 mmol) in dichloromethane (10 mL) was added dropwise over a period of 15 min. The solution was stirred at −78° C. for another 15 min. Triethylamine (6.0 mL, 43 mmol) was added. The solution was stirred at −78° C. for 5 min and then warmed to room temperature. The solution was diluted with dichloromethane (100 mL) and extracted with 1 N hydrochloric acid (100 mL). The aqueous phase was extracted with dichloromethane (50 mL). The combined organic layers were washed with saturated sodium hydrogen carbonate solution (100 mL) and dried over magnesium sulfate. The solvent was removed in vacuo. The crude product was purified by column chromatography on silica (140 g) with ethyl acetate/heptane (1:3) to give 1.10 g of 3-(tert-butoxycarbonylamino)-3-methylbutanal.

$^1$H-NMR (CDCl$_3$): d 1.39 (s, 6H); 1.45 (s, 9H); 2.85 (d, 2H); 4.73 (br. 1H); 9.80 (t, 1H).

Ethyl (2E)-5-(tert-Butoxycarbonylamino)-5-methylhex-2-enoate:

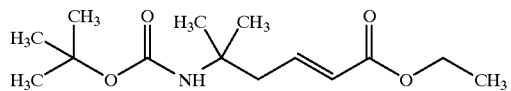

Step C: Triethylphoshonoacetate (1.96 mL, 9.8 mmol) was dissolved in tetrahydrofuran (30 mL). Potassium tert-butoxide (1.10 g, 9.8 mmol) was added. The solution was stirred for 40 min at room temperature. A solution of 3-(tert-butoxycarbonylamino)-3-methylbutanal (1.10 g, 5.5 mmol) in tetrahydrofuran (6 mL) was added. The solution was stirred at room temperature for 75 min. It was diluted with ethyl acetate (100 mL) and 1 N hydrochloric acid (100 mL). The phases were separated. The aqueous phase was extracted with ethyl acetate (2×50 mL). The combined organic phases were washed with saturated sodium hydrogen carbonate solution (60 mL) and dried over magnesium sulfate. The solvent was removed in vacuo. The crude product was purified by column chromatography on silica (90 g) with ethyl acetate/hepatane (1:4) to give 1.27 g of ethyl (2E)-5-(tert-butoxycarbonylamino)-5-methylhex-2-enoate.

$^1$H-NMR (CDCl$_3$): d 1.30 (s, 6H); 1.30 (t, 3H); 1.46 (s, 9H); 2.62 (d, 2H); 4.27 (q, 2H); 4.42 (br, 1H); 5.88 (d, 1H); 6.94 (td, 1H).

Step D: Ethyl (2E)-5-(tert-butoxycarbonylamino)-5-methylhex-2-enoate (1.233 g, 4.54 mmol) was dissolved in dioxane (20 mL). Lithium hydroxide (0.120 g, 5.00 mmol) was added as a solid. Water (10 mL) was added, until a clear solution was reached. The solution was stirred 16 h at room temperature. The solution was diluted with water (70 mL) and was extracted with tert-butyl methyl ether (2×100 mL). The aqueous phase was acidified with 1 N sodium hydrogensulfate solution (pH=1) and was extracted with tert-butylmethylether (3×70 mL). The organic phases were combined and dried over magnesium sulfate. The solvent was removed in vacuo to give 1.05 g of (2E)-5-(tert-butoxycarbonylamino)-5-methylhex-2-enoic acid. The crude product was used for further syntheses.

$^1$H-NMR (DMSO d$_6$): d 1.15 (s, 6H); 1.35 (s, 9H); 2.53 (d, 2H); 5.75 (d, 1H); 6.57 (br, 1H); 6.75 (td, 1H); 12.15 (s, 1H).

Synthesis of buildingblock 5:

(2S)-2-(((Carboxy)methoxy)methyl)pyrrolidin-1-carboxylic acid tert-butylester:

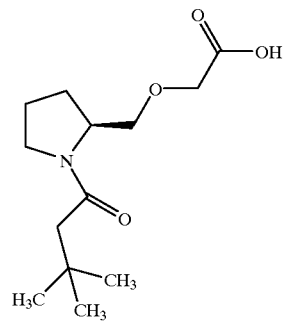

To a solution of N-t-butyloxycarbonyl-(S)-prolinol (5.0 g, 25 mmol) in 1,2-dichloroethane (500 ml) rhodium(II)acetate (180 mg) was added and the mixture was heated to 80° C. Ethyldiazoacetate (3.9 ml, 37 mmol) in 1,2-dichloroethane (180 ml) was added over a period of 90 min and the mixture was heated at 80° C. for 3 hours. Then another portion of ethyl diazoacetate (1.3 ml, 12 mmol) in 1,2-dichloroethane (40 ml) was added and the mixture was refluxed for 6 hours. The mixture was cooled to room temperature and washed with saturated sodium bicarbonate (2×100 ml) and brine (100 ml), dried (magnesium sulfate) and concentrated in vacuo. The crude product was chromatographed on silica (300 g) with petrol ether/ethyl acetate 4:1 as eluent to give 4.7 g of (2S)-2-(((ethoxycarbonyl)methoxy)methyl) pyrrolidin-1-carboxylic acid tert-butylester. The obtained product was dissolved in 1 M lithium hydroxide in water/methanol 1:3 (50 ml) and stirred at room temperature overnight. The mixture was concentrated in vacuo, water (20 mL) was added and washed with ether (20 mL). The aqueous phase was acidified to pH 4 with 1 M aqueous hydrogen chloride, extracted with ethyl acetate (2×100 ml) and the combined organic layers were dried (magnesium sulfate) and concentrated in vacuo to give 3.6 g of (2S)-2-(((carboxy)methoxy)methyl)-pyrrolidin-1-carboxylic acid tert-butyl ester.

1H-NMR (CDCl$_3$): d 1.45 (2, 9H) 1.90 (m, 4H) 3.55 (t, 2H) 3.60 (m, 3H) 4.10 (s, 2H) 10.6 (s, 1H).

Synthesis of buildingblock 6

(2-(tert-Butoxycarbonylamino)butoxy)acetic acid:

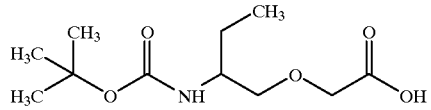

To a solution of (1-(hydroxymethyl)propyl)carbamic acid tert-butylester (7.2 g, 39 mmol) in 1,2-dichloroethane (500 ml) rhodium(II)acetate (180 mg) was added and the mixture was heated to 80° C. Ethyldiazoacetate (6.0 ml, 57 mmol) in 1,2-dichloroethane (180 ml) was added over a period of 60 min and the mixture was heated at 80° C. for 6 hours. Then another portion of ethyldiazoacetate (2.0 ml, 19 mmol) in 1,2-dichloroethane (40 ml) was added and the mixture was refluxed for 7 hours. The mixture was cooled to room temperature and washed with sodium bicarbonate (2×100 ml) and brine (100 ml), dried over magnesium sulfate and concentrated in vacuo. The crude product was chromatographed on silica (300 g) with pentane/ethyl acetate 7:3 as eluent to give 4.3 g of (2-(tert-butoxycarbonylamino) butoxy)acetic acid ethylester. The product was dissolved in of 1 M lithium hydroxide in water/methanol 1:3 (40 ml) and stirred at room temperature for 4 hours. The mixture was concentrated in vacuo and water (100 mL) was added and the solution was washed with ether (20 mL). The aqueous phase was acidified to pH 4 with 1 M aqueous hydrogen chloride and extracted with ethyl acetate (200 ml), dried over magnesium sulfate and concentrated in vacuo to give 2.46 g of (2-(tert butoxycarbonylamino)butoxy)acetic acid.

$^1$H-NMR (CDCl$_3$): d 0.95 (t, 3H) 1.45 (s, 9H) 1.60 (m, 3H) 3.55 (m, 2H) 4.10 (s, 2H)

Synthesis of buildingblock 7

3-(1-(N-tertbutoxycarbonylamino)ethyl)benzoic acid:

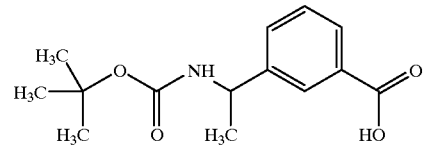

Ammonium acetate (10.6 g, 138 mmol) was evaporated from dry ethanol (100 mL), and redissolved in dry methanol (100 mL) over molecular sieves (3A, 3 g). 3-Acetylbenzonitrile (2.0 g, 13.8 mmol) was added. After 30 minutes at room temperature sodium cyanoborohydride (0.87 g, 138 mmol) was added and the reaction mixture was stirred for 18 hours. The reaction mixture was concentrated in vacuo and redissolved in water (100 mL). Concentrated hydrochloric acid was added until pH 2, and the aqueous solution was extracted with ethyl acetate (2×100 mL). The aqueous phase was adjusted to pH 11 with solid potassium hydroxide, and extracted with dichloromethane (2×100 mL). The combined organic phases were dried (magnesium sulfate) and concentrated in vacuo. A concentrated solution of hydrogen chloride in ethyl acetate added (100 mL) was, and the solution was concentrated in vacuo. The residue was dissolved in ethanol (25 mL) and sulphuric acid (9N, 25 mL) was added. After 16 hours at room temperature and 2 hours at reflux temperature the ethanol was removed by evaporation in vacuo and the residual aqueous mixture was adjusted to pH>8 using solid potassium hydroxide. Ditertbutyldicarbonate (2.0 g) dissolved in tetrahydrofuran (100 mL) was added at 0° C. After 18 hours at room temperature the reaction mixture was concentrated in vacuo and redissolved in water (100 mL). Solid citric acid was added until pH 5. The reaction mixture was extracted with dichloromethane (2×100 mL), and the combined organic phases was dried (magnesium sulfate) and concentrated in vacuo. The residue was purified by column chromatography on silica gel (3×40 cm) using ethanol and dichloromethane (1:9) as eluent to give 1.1 g of 3-(1-(N-tertbutoxycarbonyl)aminoethyl) benzoic acid.

General procedure for the conversion of N-Boc-protected buildingblocks to N-Troc-protected analogs: (Also valid for N-FMOC buildingsblocks using TrocOSu instead of FMOC-OSu)

To a solution of hydrogen chloride in ethyl acetate (3M, 25 ml) was added the Boc-protected buildingblock (0.01 mol) and the mixture was stirred for 30 min. Diethyl ether (100 ml) was added and the precipitate was filtered and dissolved in a mixture of aqueous sodium hydrogencarbonate (5%) and dioxane (1:1, 100 ml). Succinimidyl 2,2,2-trichloroethyl carbonate (0.01 mole) was added and the mixture was stirred overnight. The solvent was removed in vacuo and the residue was dissolved in water (100 ml) and washed once with diethyl ether (50 ml) and acidified to pH 3 with a solution of aqueous hydrogen sulphate. The aqueous phase was extracted with methylene chloride (3×100 ml) and the combined organic phases were dried (magnesium sulphate) and the solvent was removed in vacuo to afford the Troc protected buildingblock.

Other buildingblocks:

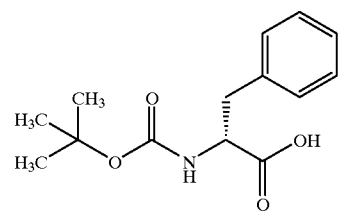

Boc-D-Phe-OH

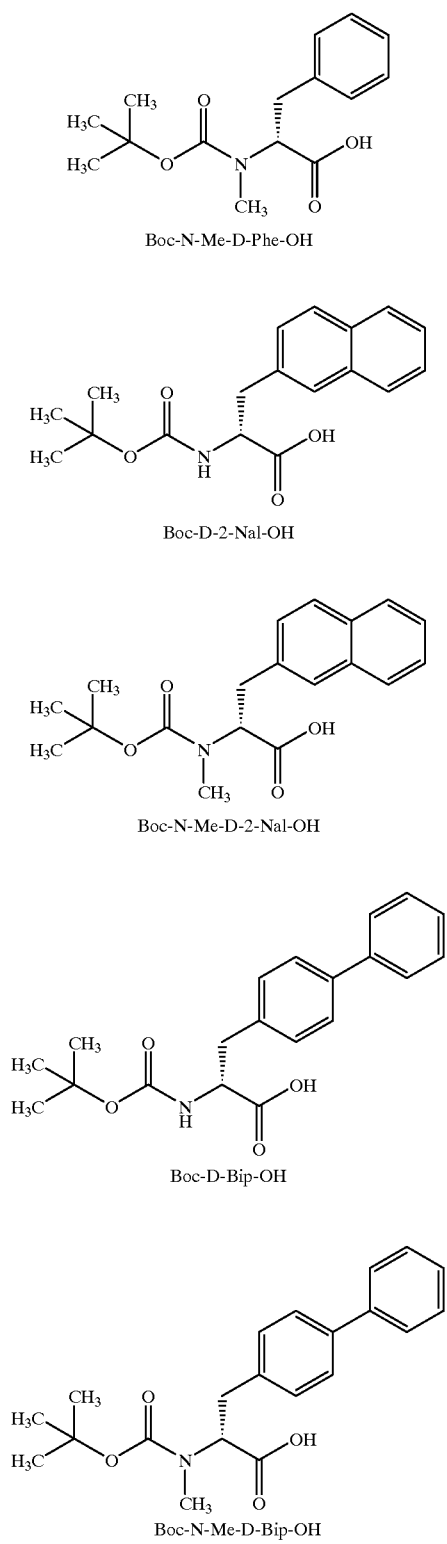
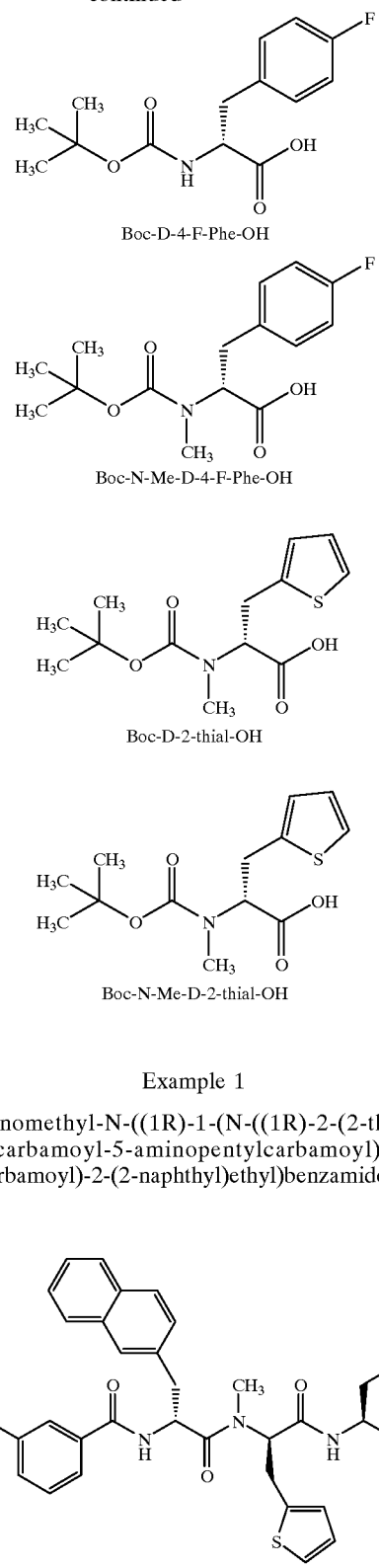
Example 1
3-Aminomethyl-N-((1R)-1-(N-((1R)-2-(2-thienyl)-1-((1S)-1-carbamoyl-5-aminopentylcarbamoyl)ethyl)-N-methylcarbamoyl)-2-(2-naphthyl)ethyl)benzamide.

[(1S)-1-Carbamoyl-5-(2,2,2-trichloroethoxycarbonylamino)pentyl]carbamic acid tert butyl ester

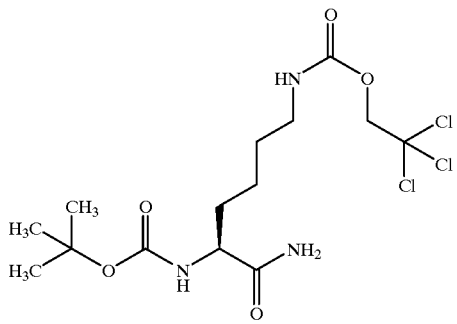

BocLys(Z)OSu (50 g; 0.10 mol) and ammonium hydrogencarbonate (25 g; 0.32 mole) were dissolved in DMF (300 ml) and stirred overnight. Water (1000 ml) was added and the precipitate was isolated by filtration and washed with water (3×200 ml). The precipitate was dissolved in methanol (500 ml) and palladium on carbon (15 g; wet, 10%) was added. The mixture was hydrogenated for 4 h at ambient pressure, filtered and the solvent was removed in vacuo. Th e residue was dissolved in THF (500 ml) and aqueous sodium hydroxide (4M, 50 ml) and succinimidyl 2,2,2-trichloroethyl carbonate was added (30.4 g .;0. 10 mole) and the mixture was stirred for 3 h. The mixture was evaporated and methylene chloride (400 ml) was added. The organic phase was washed with water (300 ml), an aqueous solution of sodium hydrogensulphate (300 ml), an aqueous solution of sodium hydrogencarbonate (300 ml) and water (300 ml). The organic phase was dried (magnesium sulphate) and the solvent was removed in vacuo to afford 39.5 g of [(1S)-1-carbamoyl-5-(2,2,2-trichloroethoxycarbonylamino)pentyl] carbamic acid tert butyl ester.

$^1$H-NMR: (CDCl$_3$) d 1.43 (s, 9H); 1.53–1.89 (m, 6H); 3.23 (q, 2H); 4.15 (m, 3H); 4.72 (.s, 2H).

((5S)-5-Amino-5-carbamoylpentyl)carbamic acid 2,2,2-trichloroethyl ester hydrochloride

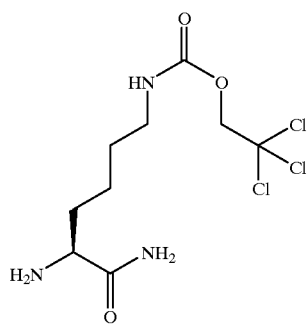

[(1S)-1-carbamoyl-5-(2,2,2-trichloroethoxycarbonylamino)pentyl]carbamic acid tert butyl ester (39.5 g; 94 mmole) was dissolved in a solution of hydrogen chloride in ethyl acetate (1.5 M, 300 ml) and stirred for 30 min. Diethyl ether (300 ml) was added and the precipitate was filtered and dried to afford 30.5 g of ((5S)-5-amino-5-carbamoylpentyl)carbamic acid 2,2,2-trichloroethyl ester hydrochloride.

$^1$H-NMR: (DMSO) d 1.31 (m, 2H); 1.45 (m, 2H); 1.75 (m, 2H); 3.02 (dd, 2H); 3.67 (t, H); 4.77 (s, 2H); 7.51 (s, 1H); 7.70 (t, 1H); 7.96 (.s, 1H); 2,2,2-trichloroethyl ester

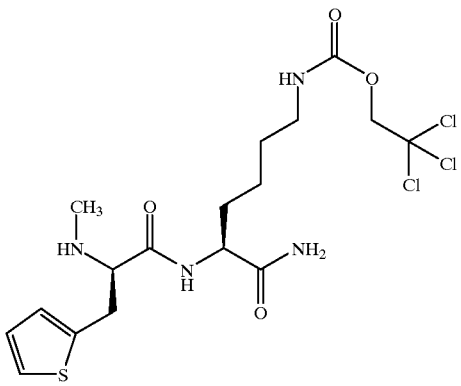

2-(tert-Butoxycarbonylmethylamino)-3-(2-thienyl) propionic acid (10.07 g; 35 mmole), HOBt (5.72 g; 42 mmole) and EDAC (7.09 g; 37 mmole) were added to methylene chloride (200 ml) and stirred for 15 min. ((5S)-5-amino-5-carbamoylpentyl)carbamic acid 2,2,2-trichloroethyl ester hydrochloride (12.61 g; 35 mmole) was added and the mixture was stirred overnight. Methylene chloride (200 ml) was added and the organic phase was washed with water (200 ml), an aqueous solution of sodium hydrogensulphate (200 ml), an aqueous solution of sodium hydrogencarbonate (200 ml) and water (200 ml). The organic phase was dried (magnesium sulphate) and the solvent was removed in vacuo. The residue was dissolved in a solution of hydrogen chloride in ethyl acetate (3 M; 100 ml) and stirred for 30 min. Diethyl ether and water (500 ml) was added, the phases were separated and the acidic aqueous phase was treated with a solution of sodium carbonate to pH 10. The aqueous phase was extracted with methylene chloride (4×700 ml) and the phases were separated. The organic phase was dried (magnesium sulphate) and the solvent was removed in vacuo to afford 11.0 g of [(5S)-5-carbamoyl-5-((2R)-2-methylamino-3-(2-thienyl)-propionylamino)-pentyl]-carbamic acid 2,2,2-trichloroethyl ester.

$^1$H-NMR: (DMSO) d 1.11–1.68 (m, 6H); 2.20 (s, 3H); 2.86–3.08 (m, 4H); 3.18 (t, 1H); 4.18 (dd, 1H); 4.78 (s, 1H); 6.88 (d, 1H); 6.92 (t, 1H); 7.30 (d, 1H)

((5R)-5-{(2R)-2-[((2R)-2-Amino-3-(2-naphthyl) propionyl)methylamino]-3-(2-thienyl)propionylamino}-5-carbamoylpentyl)carbamic acid 2,2,2-trichloroethyl ester

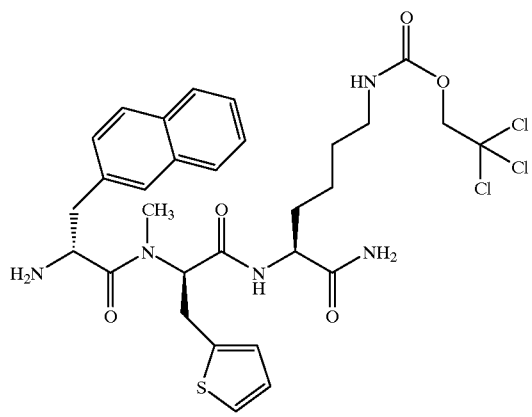

(2R)-2-(tert-Butoxycarbonylmethylamino)-3-(2-napthyl) propionic acid (5.00 g; 15.8 mmole), HOAt (2.35 g; 17 mmole) and EDAC (3.03 g; 15.8 mmole) were added to methylene chloride (200 ml) and stirred for 15 min. [(5S)-5-carbamoyl-5-((2R)-2-methylamino-3-(2-thienyl)propionylamino)pentyl]carbamic acid 2,2,2-trichloroethyl ester (7.01 g; 14.5 mmole) was added and the mixture was stirred overnight. Methylene chloride (200 ml) was added and the organic phase was washed with water (200 ml), an aqueous solution of sodium hydrogensulphate (200 ml), an aqueous solution of sodium hydrogencarbonate (200 ml) and water (200 ml). The organic phase was dried (magnesium sulphate) and the solvent was removed in vacuo. The residue was dissolved in a mixture of trifluoroacetic acid (30 ml) and methylene chloride (70 ml) and stirred for 15 min. Water (150 ml) and sodium hydrogencarbonate were added to neutral pH, the phases were separated and the aqueous phase was extracted with methylene chloride (2×100 ml) and the phases were separated. The combined organic phase were dried (magnesium sulphate) and the solvent was removed in vacuo and the residue was chromatographed on silica using a mixture of aqueous ammonia in water (25%), ethanol and methylene chloride (0.7:9.3:90) as eluent to afford 6.3 g of ((5S)-5-{(2R)-2-[((2R)-2-amino-3-(2-naphthyl)propionyl)methylamino]-3-(2-thienyl)propionylamino}-5-carbamoylpentyl)carbamic acid 2,2,2-trichloroethyl ester.

¹H-NMR: (CDCl₃; selected peaks for major rotamer): d 1.36–1.61 (m, 6H); 2.88 (s, 3H); 4.00 (dd; 1H); 4.65 (s, 2H).

MS(ES): m/z : 684 (M+H)⁺

3-[(2,2,2-Trichloroethoxycarbonylamino)methyl]benzoic acid (8.52 g; 26.1 mmole) and EDAC (2.49 g; 13.0 mmole) were dissolved in methylene chloride (150 ml) and stirred for 15 min. ((5S)-5-{(2R)-2-[((2R)-2-Amino-3-(2-naphthyl)propionyl)methylamino]-3-(2-thienyl)propionylamino}-5-carbamoylpentyl)carbamic acid 2,2,2-trichloroethyl ester (8.92 g; 13.0 mmole) was added and the mixture was stirred for 30 min. DIEA (3.6 ml) was added and the mixture was stirred overnight. The mixture was washed with an aqueous solution of sodium hydrogencarbonate (10%, 2×100 ml) and with an aqueous solution of sodium hydrogensulphate (10%, 1×100 ml). The organic phase was dried (magnesium sulphate) and the solvent removed in vacuo. The residue was chromatograped on silica using ethyl acetate as eluent and the protected intermediate was dissolved in a mixture of THF (100 ml) and an aqueous solution of potassium dihydrogenphosphate (1M, 40 ml). Zinc powder (50 g) was added and the mixture was stirred overnight. The mixture was filtered and the solvent was removed in vacuo. The residue was chromatograped on reverse phase silica (Waters, RP-18,125 Å) using gradient elution with acetonitrile and water (10% to 30%) with 0.1% TFA added to afford 7.01 g of the title compound.

¹H-NMR: (DMSO;): d 2.88; 3.08; (two s, 3H); 4.05 (s, 3H); 4.15; 4.20 (two dd, 1H); 5.02; 5.12; 5.15; 5.25 (four dd; 2H).

HPLC: (method A1): R_t=26.90 min.

MS(ES): m/z 643.4 (M+H)⁺.

Example 2

3-((1R/S)-1-Aminoethyl)-N-((1R)-1-{N-[(1R)-1-(N-(carbamoylmethyl)-N-methylcarbamoyl)-2-phenylethyl]-N-methylcarbamoyl}-2-(2-naphthyl)ethyl)-N-methylbenzamide

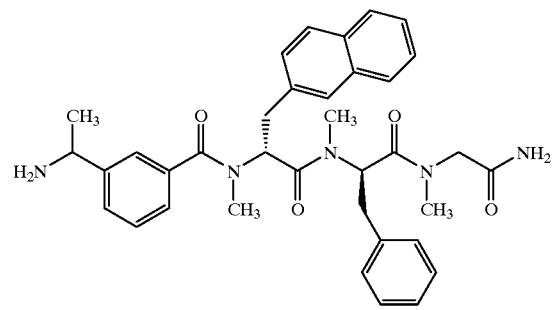

The title compound was prepared as in example 1 using sarcosine amide instead of ((5S)-5-Amino-5-carbamoylpentyl)carbamic acid 2,2,2-trichloroethyl ester hydrochloride. Boc-N-Me-D-Phe-OH, Boc-N-Me-D-2-Nal-OH and buildingblock 7 were used.

¹H-NMR: ((CDCl₃; selected peaks for major rotamer): d 1.25 (d, 3H); 2.51 (s, 3H); 2.65 (s, 3H); 3.03 (s, 3H);

HPLC: (method A1): R_t=27.30 min.

MS(ES): m/z 608.4 (M+H)⁺.

Example 3

2-Amino-N-(((1S)-1-(((1R)-1-(((1R)-1-(((1S)-1-carbamoyl-5-(methylsulfonylamino)pentyl)carbamoyl)-2-phenylethyl)carbamoyl)-2-(2-naphthyl)ethyl)carbamoyl)-2-(4-imidazolyl)ethyl)carbamoyl)-2-methylpropanamide

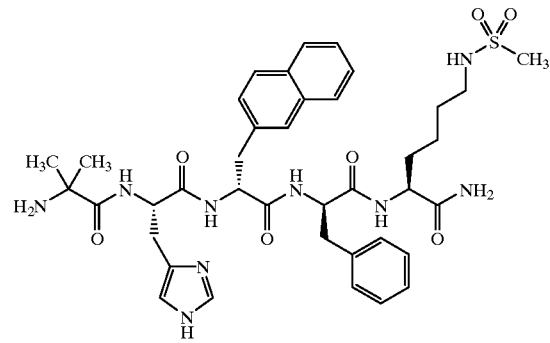

2-Amino-N-(((1S)-1-(((1R)-1-(((1R)-1-(((1S)-5-amino-1-carbamoylpentyl)carbamoyl)-2-phenylethyl)carbamoyl)-2-(2-naphthyl)ethyl)carbamoyl)-2-(4-imidazolyl)ethyl)carbamoyl)-2-methylpropanamide (217 mg, 0.30 mmol prepared as in WO9517423) was dissolved in 1,4-dioxane (2 ml) and water(2 ml). Potassium carbonate (207 mg, 1.50 mmol) was added. A solution of methanesulfonyl chloride (0.023 ml, 0.29 mmol) in 1,4-dioxane (0.5 ml) was added. The reaction mixture was stirred for 24 h at room temperature. The solvent was removed in vacuo. The residue was purified by three HPLC-chromatographic runs on a 25 mm×250 mm 10 m C18 silica column at 40° C. with a gradient of 20 to 40% acetonitrile in a 0.1 M ammonium sulfate buffer, which was adjusted to pH 2.5 with 4M sulfuric acid. The peptide containing fractions were collected, diluted with 3 volumes of water and applied to a Sep-Pak® C18 cartridge (Waters part. #: 51910) which was equilibrated with 0.1% trifluoroacetic acid. The peptide was eluted from the Sep-Pak® cartridge with 70% acetonitrile in a 0.1% trifluoroacetic acid solution in water. The product was lyophilized to afford 61 mg of the title compound as a trifluoroacetate salt

| HPLC: | 23.68 min (method A1). |
|---|---|
|  | 25.55 min (B1). |
| MS: | 790.4 ([M + H]$^+$). |

Example 4

[(5S)-5-((2R)-2-{N-[(2R)-2-(3-(Aminomethyl)benzoylamino)-3-(2-naphthyl)propionyl]-N-methylamino}-3-(2-thienyl)propionylamino)-5-carbamoylpentyl]carbamic acid benzyl ester

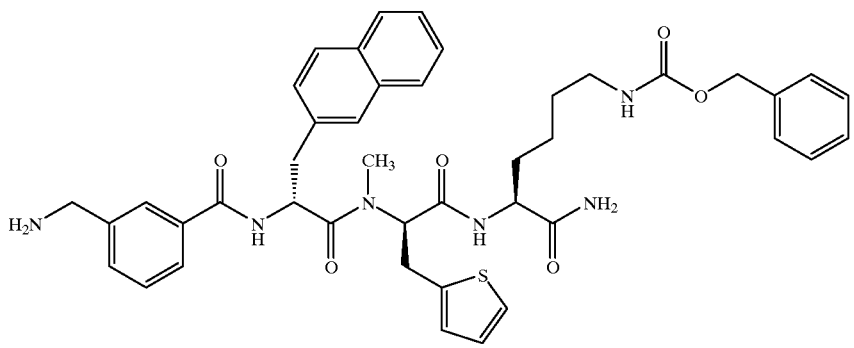

The title compound was prepared as in example 1, except that the Z-protecting group was not transferred into the Troc-protecting group in the first step.
HPLC (method A1): r$_t$39.38 min.

Example 5

N-((1R)-1-{N-[(1R)-1-(((1S)-5-Amino-1-carbamoylpentyl)carbamoyl)-2-(4-fluorophenyl)ethyl]-N-methylcarbamoyl}-2-(biphenyl-4-yl)ethyl)-3-(aminomethyl)benzamide

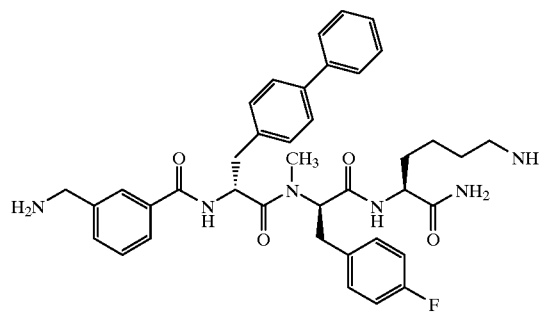

The title compound was prepared as in example 1. Boc-N-Me-D-(4-F-Phe)-OH and Boc-D-Bip-OH were employed.
HPLC: (method A1): R$_t$=30.78 min.
MS(ES): m/z 681 (M+H)$^+$.

Example 6

(2E)-5-Amino-5-methylhex-2-enoic acid N-((1R)-1-{N-[(1R)-1-(5-aminopentylcarbamoyl)-2-phenylethyl]-N-methylcarbamoyl}-2-(2-naphthyl)ethyl)-N-methylamide

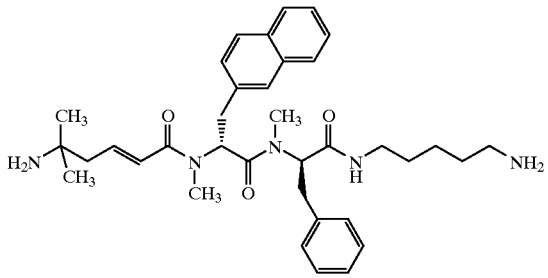

The title compound was prepared as in example 1 substituting ((5S)-5-Amino-5-carbamoyl-pentyl)-carbamic acid 2,2,2-trichloro-ethyl ester hydrochloride with N-Troc-1,5-diaminopentane (prepared as in Atwell, G. J.; Denny, A. D.; Synthesis, 1032 (1984)) and Boc-AEH-OH.
$^1$H-NMR: ((CDCl$_3$; selected peaks for major rotamer): d 0.92 (s, 6H); 2.91 (s, 3H); 2.95 (s, 3H); 4.22 (dd, 1H); 6.22 (d, 1H)
HPLC: (method A1): R$_t$=27.30 min.
MS(ES): m/z 600.2 (M+H)$^+$.

Example 7

3-((1R/S)-1-Aminoethyl)-N-[(1R)-2-(biphenyl-4-yl)-1-(N-{(1R)-1-[N-(3-dimethylaminopropyl)-N-methylcarbamoyl]-2-phenylethyl}-N-methylcarbamoyl)ethyl]-N-methylbenzamide

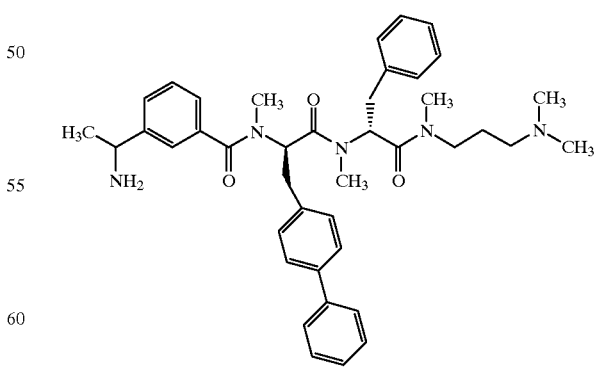

The title compound was prepared as in example 1, omitting acidic washes and using N-methyl-N'-dimethyldiaminopropane, buildingblock 7, Boc-N-Me-D-Phe-OH and Boc-N-Me-D-Bip-OH as the starting materials.

¹H-NMR: ((CDCl₃, selected peaks): d 1.36 (d, 3H); 2.26 (s, 3H); 2.32 (s, 6H); 2.52 (s, 3H); 3.03 (s, 3H)

HPLC: (method A1): R$_t$=28.88 min.

MS(ES): m/z 662.2 (M+H)⁺.

Example 8

(2E)-5-Amino-5-methylhex-2-enoic acid N-[(1R)-2-(biphenyl-4-yl)-1-(N-{(1R)-1-[N-(3-dimethylaminopropyl)-N-methylcarbamoyl]-2-phenylethyl}-N-methylcarbamoyl)ethyl]-N-methylamide

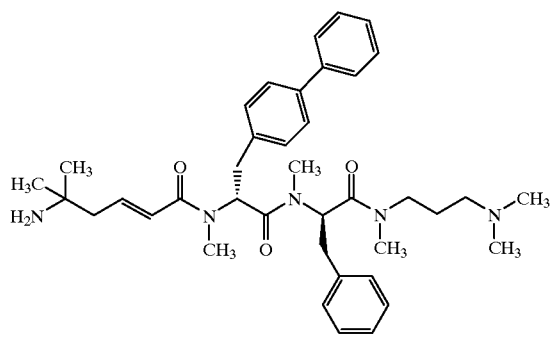

The title compound was prepared as in example 1, omitting acidic washes and using N-methyl-N'-dimethyldiaminopropane, Boc-N-Me-D-Phe-OH and Boc-N-Me-D-Bip-OH and Boc-AEH-OH as the starting materials ¹H-NMR: ((CDCl₃, selected peaks): d 1.17 (.s, 6H); 2.10 (s, 6H); 2.19 (s, 3H); 2.29 (s, 3H) 2.48 (s, 3H); 5.82 (m, 1H); 6.18 (d, 1H).

HPLC: (method A1): R$_t$=28.93 min.

MS(ES): m/z 640.2 (M+H)⁺.

Example 9

(2E)-5-Amino-5-methylhex-2-enoic acid N-((1R)-1-{N-[(1R)-1-((1S)-5-amino-1-carbamoylpentylcarbamoyl)-2-phenylethyl]-N-methylcarbamoyl}-2-(2-naphthyl)ethyl)-N-methylamide

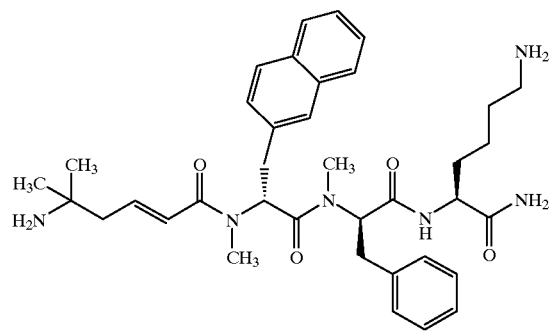

The title compound was prepared as in example 1. Boc-AEH-OH and Boc-N-Me-D-2-Nal-OH were used as starting materials.

HPLC: (method A1): R$_t$=23.48 min.

MS(ES): m/z 643.2 (M+H)⁺.

Example 10

N-((1R)-1-{N-[(1R)-1-((1S)-5-Amino-1-carbamoylpentylcarbamoyl)-2-phenylethyl]-N-methylcarbamoyl}-2-(2-naphthyl)ethyl)-3-((1R/S)-1-aminoethyl)-N-methylbenzamide

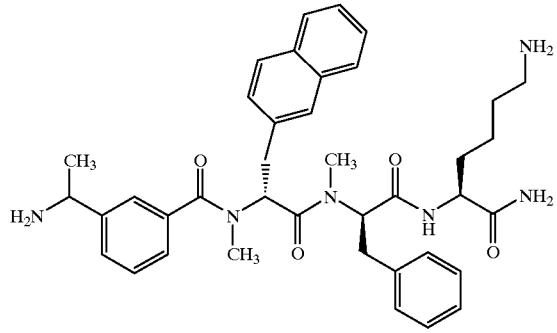

The title compound was prepared as in example 1. Boc-N-Me-D-Phe-OH, Boc-N-Me-D-2-Nal-OH and building-block 7 were used as starting materials.

¹H-NMR: ((CDCl₃; selected peaks for major rotamer): d 1.54 (d, 3H); 2.77 (s, 3H); 3.01 (s, 3H); 4.42 (q, 1H); 5.42–5.72 (m, 2H)

HPLC: (method A1): R$_t$=26.61 min.

MS(ES): m/z 665.2 (M+H)⁺.

Example 11

(2E)-5-Amino-5-methylhex-2-enoic acid ((1R)-1-{N-[(1R)-1-(((1S)-5-amino-1-(dimethylcarbamoyl)pentyl)carbamoyl)-2-phenylethyl]-N-methylcarbamoyl}-2-(2-naphthyl)ethyl)amide

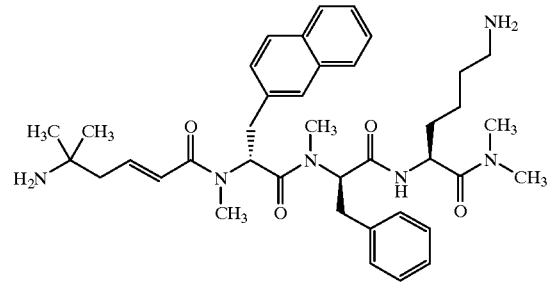

The title compound was prepared as in example 1. Dimethylamine was used instead of ammonium hydrogencarbonate. Boc-N-Me-D-Phe-OH, Boc-N-Me-D-2-Nal-OH and Boc-AEH-OH were used as starting materials.

¹H-NMR: ((CDCl₃; selected peaks): d 1.32 (s, 6H); 1.81 (dd, 2H); 2.81; (s, 3H); 2.92 (s, 3H); 3.04 (s, 3H); 3.11 (s, 3H); 4.96 (dd, 1H); 5.45 (dd, 1H); 5.60 (dd, 1H); 6.11 (d, 1H).

HPLC: (method A1): R$_t$=26.82 min.

MS(ES): m/z 671.2 (M+H)⁺.

Example 12

N-((1R)-1-{N-[(1R)-1-(((1S)-5-Amino-1-(dimethylcarbamoyl)pentyl)carbamoyl)-2-phenylethyl]-N-methylcarbamoyl}-2-(biphenyl-4-yl)ethyl)-3-aminomethyl-N-methylbenzamide

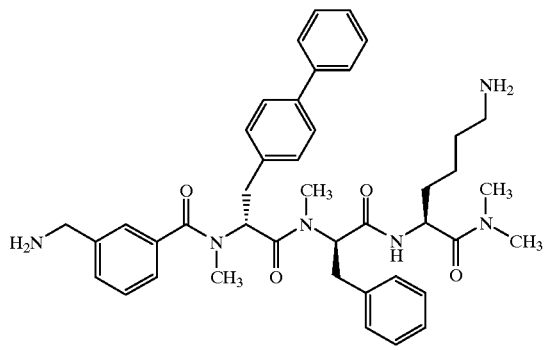

The title compound was prepared as in example 1. Dimethylamine was used instead of ammonium hydrogencarbonate. Boc-N-Me-D-Phe-OH, Boc-N-Me-D-Bip-OH and Boc-AMB-OH were used as starting materials.

$^1$H-NMR: ((CDCl$_3$; selected peaks): d 2.85 (s, 3H); 2.94 (s, 3H); 2.96 (s, 3H); 3.05 (s, 3H); 3.96 (dd, 2H); 4.89 (dd, 1H); 5.48 (dd, 1H).

HPLC: (method A1): R$_t$=30.30 min.

MS(ES): m/z 705.4 (M+H)$^+$.

Example 13

(2E)-5-Amino-5-methyl-hex-2-enoic acid N-((1R)-1-{N-[(1R)-1-((1S)-5-amino-1-(dimethylcarbamoyl) pentylcarbamoyl)-2-phenylethyl]-N-methylcarbamoyl)-2-(biphenyl-4-yl)ethyl)-N-methylamide

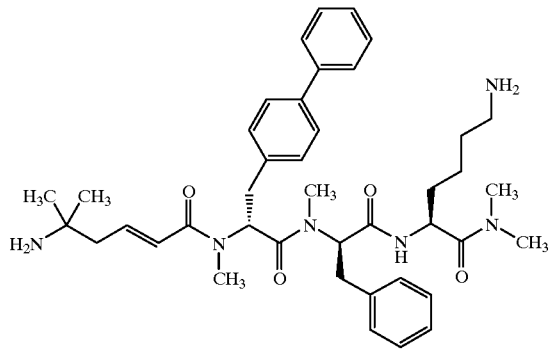

The title compound was prepared as in example 1. Dimethylamine was used instead of ammonium hydrogencarbonate. Boc-N-Me-D-Phe-OH, Boc-N-Me-D-Bip-OH and Boc-AEH-OH were used as starting materials.

$^1$H-NMR: ((CDCl$_3$; selected peaks for major rotamer): d 1.12 (s, 6H); 2.45 (s, 3H); 2.90 (s, 3H); 3.03 (s, 3H); 3.05 (s, 3H); 4.82 (dd, 1H); 5.38 (m, 1H); 6.18 (d, 1H).

HPLC: (method A1): R$_t$=30.22 min.

MS(ES): m/z 697.6 (M+H)$^+$.

Example 14

N-((1R)-1-{[(1R)-1-(((1S)-5-Amino-1-carbamoylpentyl) carbamoyl)-2-(4-fluorophenyl)ethyl]-N-methylcarbamoyl}-2-(2-naphthyl)ethyl)-3-aminomethylbenzamide

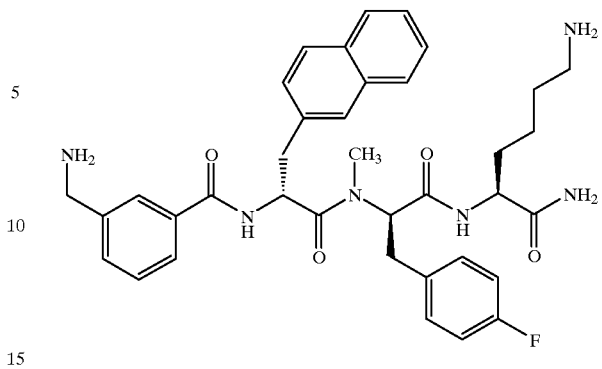

The title compound was prepared as in example 1. Boc-N-Me-D-4-F-Phe-OH, Boc-D-2-Nal-OH and Boc-AMB-OH were used as starting materials.

$^1$H-NMR: (MeOH; selected peaks for major rotamer): d 1.10–1.90 (m, 6H); 3.00 (s, 3H); 4.12 (s, 2H); 4.55 (dd, 1H); 5.26 (dd, 1H)

HPLC: (method A1): R$_t$=28.23 min.

MS(ES): m/z 655.2 (M+H)$^+$.

Example 15

(2E)-5-Amino-5-methylhex-2-enoic acid ((1R)-1-{N-[(1R)-1-(((1S)-5-amino-1-carbamoylpentyl)carbamoyl)-2-(4-fluorophenyl)ethyl]-N-methylcarbamoyl}-2-(2-naphthyl)ethyl)amide

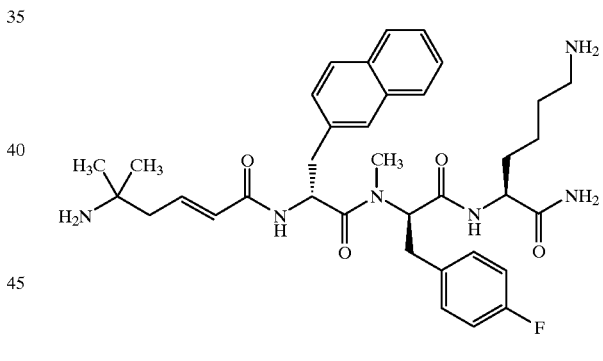

The title compound was prepared as in example 1. Boc-N-Me-D-4-F-Phe-OH, Boc-D-2-Nal-OH and Boc-AEH-OH were used as starting materials $^1$H-NMR: (MeOH, selected peaks for major rotamer): d 1.32 (s, 6H); d, 2H); 2.95 (.s, 3H); 4.31 (dd, 1H); 4.50 (dd, 1H); 5.12 (t, 1H); 6.12 (d, 1H); 6.60 m, 1H)

HPLC: (method A1): R$_t$=28.05 min.

MS(ES): m/z 647.4 (M+H)$^+$.

Example 16

N-((1R)-1-{N-[(1R)-1-(((1S)-5-Amino-1-carbamoylpentyl)carbamoyl)-2-(4-fluorophenyl)ethyl]-N-methylcarbamoyl)-2-(2-naphtyl)ethyl)-3-aminomethyl-N-methylbenzamide

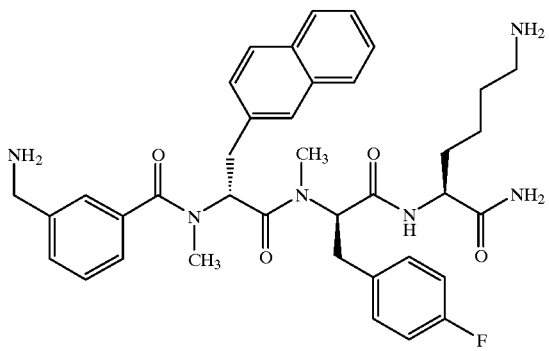

The title compound was prepared as in example 1. Boc-N-Me-D-4-F-Phe-OH, Boc-N-Me-D-2-Nal-OH and Boc-AMB-OH were used as starting materials $^1$H-NMR: ((CDCl$_3$;): d 2.61 (s, 3H); 2.87 (s, 3H); 4.30 (m, 1H); 4.70 (m, 1H);

HPLC: (method A1): R$_t$=27.03 min.
MS(ES): m/z 669.4 (M+H)$^+$.

Example 17

(2S)-6Amino-2-[(2R)-3-(4-fluorophenyl)-2(N-methyl-N-{(2R)-3-(2-naphthyl)-2-[2-(((2S)-pyrrolidin-2-yl)methoxy)acetylamino]propionyl}amino)propionylamino]hexanoic acid amide

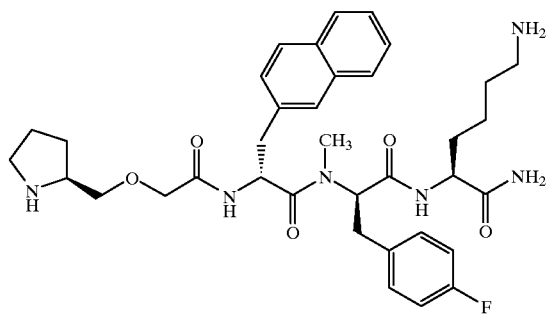

The title compound was prepared as in example 1. Boc-N-Me-D-4-F-Phe-OH, Boc-D-2-Nal-OH and buildingblock 6 were used as starting materials $^1$H-NMR: (MeOH, selected peaks): d 1.22–1.90 (m, 10H); 3.02 (s, 3H); 3.49 (dd, 1H); 3.95 (ab-syst., 2H); 4.32 (dd, 1H); 4.94 (dd, 1H); 5.03, (dd, 1H); 5.15 (dd, 1H).

HPLC: (method A1): R$_t$=26.52 min.

MS(ES): m/z 663.4 (M+H)$^+$.

Example 18

(2S)-6-Amino-2-[(2R)-2-(N-{(2R)-2-[2-((2R/S)-2-aminobutoxy)acetylamino]-3-(2-naphthyl)propionyl}-N-methylamino)-3-(4-fluorophenyl)propionylamino]hexanoic acid amide The title compound was prepared as in example 1. Boc-N-Me-D-4-F-Phe-OH, Boc-D-2-Nal-OH and buildingblock 5 were used as starting materials $^1$H-NMR: (MeOH, selected peaks;): d 0.95 (t, 3H); 1.25–1.86 (m, 8H); 2.98 (s, 3H); 3.95 (m, 2H); 4.32 (dd, 1H); 4.90 (t, 1H); 5.17 (t, 1H):

HPLC: (method A1): R$_t$=26.90 min and 27.05 min (diastereomeric mixture)

MS(ES): m/z 651.2 (M+H)$^+$.

The following examples (example 19 to example 25) where prepared on solid support using the general procedure described below:

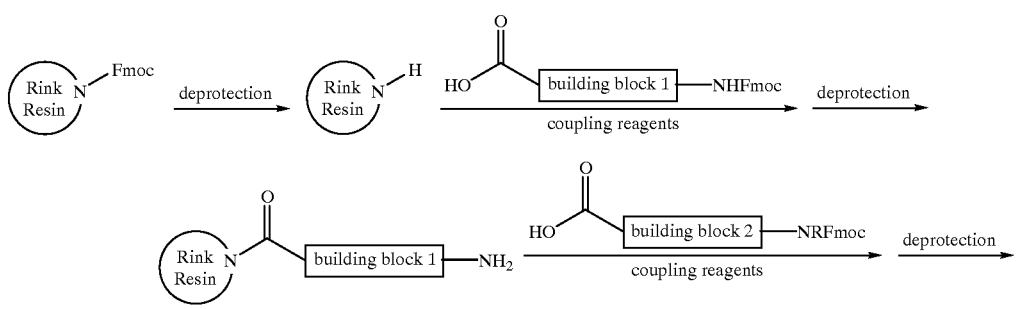

-continued

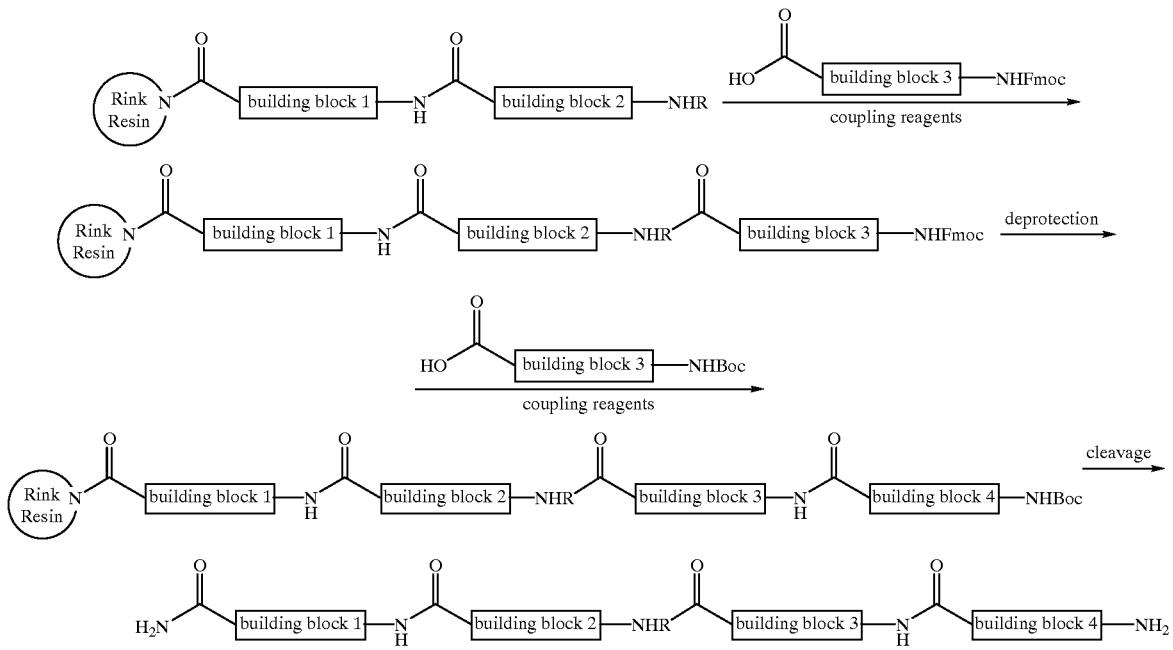

Fmoc deprotection procedure:

The resin is swelled and shaken in 20% piperidine in DMF (5 ml) for 3 min. The resin is drained and the deprotection process is repeated, with 15 min reaction time.

Standard washing procedure:

The drained resin is washed using the following standard washing procedure: The resin is repeatedly swelled, shaken and drained three times with 5mL of DMF, methylene chloride, DMF, 2-propanol, methanol and finally with diethyl ether.

Standard protocol for solid phase synthesis of example 19–25:

Deprotection:

Rink amide resin (Novabiochem 01-64-0013, 1 g, 0,46 mmol) is deprotected using the method described above followed by the standard washing procedure.

Attachment of building block 1:

Building block 1 (0.9 mmol), HOBt (138 mg, 0.9 mmol) and EDAC (173 mg, 0.9 mmol) is mixed in DMF (2 mL) for 15 min, and then transferred to the drained resin, followed by addition of DMF (3 mL). DIEA (1.6 mg, 0.9 mmol) is added after 30 min, and the reaction mixture is shaken for 20 h.

The resin is drained and the washed using the standard procedure described above. The resin is deprotected using the method described above followed by the standard washing procedure.

Attachment of building block 2:

Building block 1 (0.9 mmol), HOBt (138 mg, 0.9 mmol) and EDAC (173 mg, 0.9 mmol) is mixed in DMF (2 mL) for 15 min, and then transferred to the drained resin, followed by addition of DMF (3 mL). DIEA (116 mg, 0.9 mmol) is added after 30 min, and the reaction mixture is shaken for 20 h.

The resin is drained and the washed using the standard procedure described above. The resin is deprotected using the method described above followed by the standard washing procedure.

Attachment of building block 3:

Building block 2 (0.9 mmol), HOAt (177 mg, 0.9 mmol) and EDAC (173 mg, 0.9 mmol) is mixed in DMF (2 mL) for 15 min, and then transferred to the drained resin followed by addition of DMF (3 mL). DIEA (116 mg, 0.9 mmol) is added after 30 min, and the reaction mixture is shaken for 20 h.

The resin is drained and the washed using the standard procedure described above. The resin is deprotected using the method described above followed by the standard washing procedure.

Attachment of building block 4:

Building block 1 (0.9 mmol), HOBt (138 mg, 0.9 mmol) and EDAC (173 mg, 0.9 mmol) is mixed in DMF (2 mL) for 15 min, and then transferred to the drained resin, followed by addition of DMF (3 mL). DIPEA (116 mg, 0.9 mmol) is added after 30 min, and the reaction mixture is shaken for 20 h.

The resin is drained and the washed using the standard procedure described above. The resin is deprotected using the method described above followed by the standard washing procedure.

Detachment of compound from the resin:

The resin which has been treated as described above is swelled and shaken in a mixture of 5% water in trifluoro acetic acid (10 mL) for 1 h. The resin is then drained and repeatedly washed with triflouro acetic acid (2×5 mL) and DCM (4×5 mL). All drained solutions are combined and concentrated under nitrogen to a 4 mL volume. Et$_2$O (50 mL) is the heterogeneous mixture is centrifuged. The centrifuge pellet is washed with Et$_2$O (50 mL) and centrifuged. This treatment is repeated, and the final compound is dried in exicator for 18 h.

Using this procedure and building blocks 1–4 the following compounds (19–25 were synthesised:

Example 19

(2E)-5-Amino-5-methylhex-2-enoic acid N-((1R)-1-{N-[(1R)-1-(((1S)-5-amino-1-carbamoylpentyl)carbamoyl)-2-phenylethyl]-N-methylcarbamoyl}-2-(2-naphthyl)ethyl) amide:

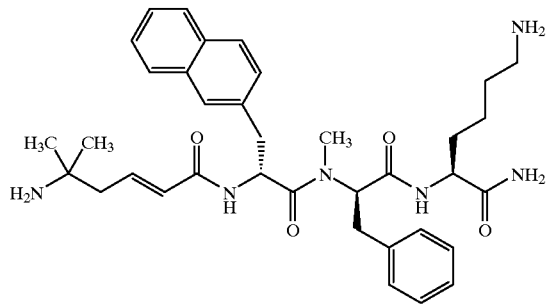

Starting material used:

Buildingblock 1: Fmoc-Lys-OH
Buildingblock 2: Fmoc-NMe-D-Phe-OH
Buildingblock 3: Fmoc-D-2Nal-OH
Buildingblock 4: Boc-AEH-OH
HPLC: Rt=17.1 min (method A)
  Rt=27.8 min (method A1)
ESMS: M+1=629.2

Example 20

(2E)-5-Amino-5-methylhex-2-enoic acid N-((1R)-1-{N-[(1R)-1-(((1S)-5-amino-1-carbamoylpentyl)carbamoyl)-2-phenylethyl]-N-methylcarbamoyl}-2)biphenyl-4-yl)ethyl}amide:

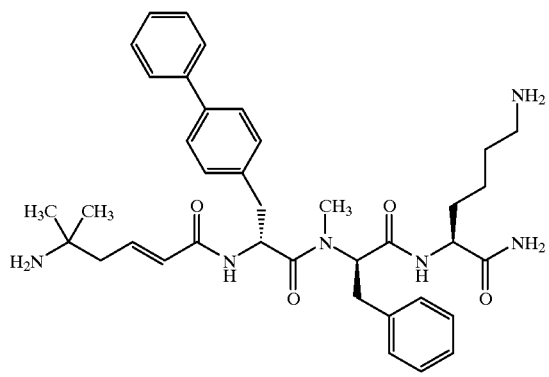

Starting material used:

Buildingblock 1: Fmoc-Lys-OH
Buildingblock 2: Fmoc-NMe-D-Phe-OH
Buildingblock 3: Fmoc-D-(4-biphenyl)-Ala-OH
Buildingblock 4: Boc-AEH-OH
HPLC: Rt=18.4 min (method A)
  Rt=30.3 min (method A1)
ESMS: M+1=655.2

Example 21

N-((1R)-1-{N-[(1R)-1-(((1S)-5-Amino-1-carbamoylpentyl)carbamoyl)-2-phenylethyl]-N-methylcarbamoyl}-2-(biphenyl-4-yl)ethyl)-3-aminomethylbenzamide:

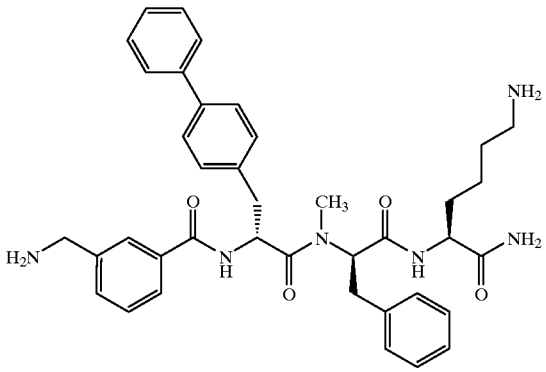

Starting material used:

Buildingblock 1: Fmoc-Lys-OH
Buildingblock 2: Fmoc-NMe-D-Phe-OH
Buildingblock 3: Fmoc-D-(4-biphenyl)-Ala-OH
Buildingblock 4: Boc-3-AMH-OH
HPLC: Rt=18.9 min (method A)
  Rt=30.4 min (method A1)
ESMS: M+1=663.4

Example 22

(2E)-5-Amino-5-methylhex-2-enoic acid N-((1R)-1-{N-[(1R)-1-(((1S)-5-amino-1-carbamoylpentyl)carbamoyl)-2-(2-thienyl)ethyl]-N-methylcarbamoyl)-2-(2-naphthyl)ethyl}amide:

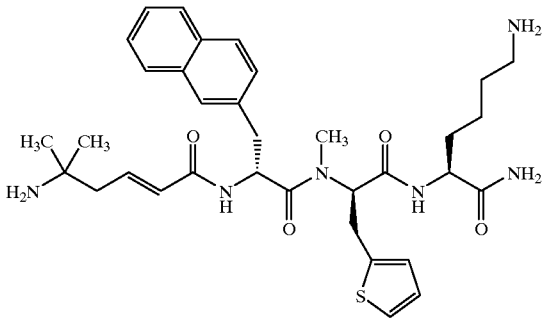

Starting material used:

Buildingblock 1: Fmoc-Lys-OH
Buildingblock 2: Fmoc-NMe-D-(2-thienyl)-Ala-OH
Buildingblock 3: Fmoc-D-2Nal-OH
Buildingblock 4: Boc-AEH-OH
HPLC: Rt=16.7 min (method A)
  Rt=26.7 min (method A1)
ESMS: M+1=635.4

Example 23

3-Aminomethyl-N-((1R)-1-(N-((1R)-2-(2-thienyl)-1-(((1S)-1-carbamoyl-5-aminopentylcarbamoyl)ethyl)-N-methylcarbamoyl)-2-(2-naphthyl)ethyl)benzamide:

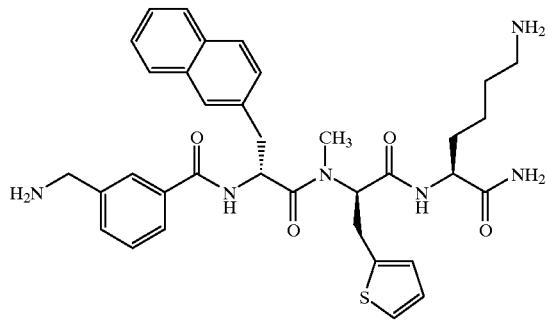

Starting material used:

Buildingblock 1: Fmoc-Lys-OH
Buildingblock 2: Fmoc-NMe-D-(2-thienyl)-Ala-OH
Buildingblock 3: Fmoc-D-2Nal-OH
Buildingblock 4: Boc-3-AMH-OH
HPLC: Rt=17.1 min (method A)
  Rt=26.8 min (method A1)
ESMS: M+1=643.4

Example 24

(2E)-5-Amino-5-methylhex-2-enoic acid N-((1R)-1-{N-[(1R)-1-(((1S)-5-amino-1-carbamoylpentyl)carbamoyl)-2-(2-thienyl)ethyl]-N-methylcarbamoyl}-2-(biphenyl-4-yl)ethyl}amide:

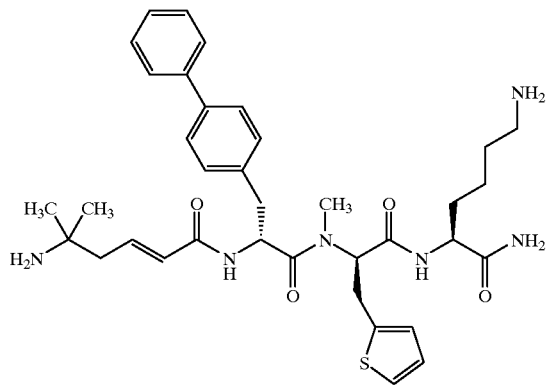

Starting material used:

Buildingblock 1: Fmoc-Lys-OH
Buildingblock 2: Fmoc-NMe-D-(2-thienyl)-Ala-OH
Buildingblock 3: Fmoc-D-(4-biphenyl)-Ala-OH
Buildingblock 4: Boc-AEH-OH
HPLC: Rt=18.7 min (method A)
  Rt=29.6 min (method A1)
ESMS: M+1=661.4

Example 25

N-((1R)-1-{N-[(1R)-1-(((1S)-5-Amino-1-carbamoylpentyl)carbamoyl)-2-(2-thienyl)ethyl]-N-methylcarbamoyl}-2-(biphenyl-4-yl)ethyl)-3-aminomethylbenzamide:

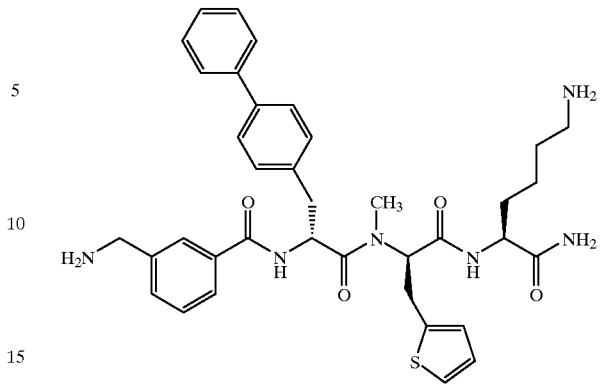

Starting material used:
Buildingblock 1: Fmoc-Lys-OH
Buildingblock 2: Fmoc-NMe-D-(2-thienyl)-Ala-OH
Buildingblock 3: Fmoc-D-(4-biphenyl)-Ala-OH
Buildingblock 4: Boc-3-AMH-OH
HPLC: Rt=18.8 min (method A)
  Rt=29.7 min (method A1)
ESMS: M+1=669.4

Acetylation of the Lysine epsilon amino group of example 26–29 was performed using the methodology described below.

The compound to be acetylated at the Lysine epsilon amino group (0.16 mmol) is disolved or suspended in 2% Na$_2$CO$_3$ aqueous solution (40 mL) and acetic acid anhydride (0.8 mmol, 75 mL) is added. This mixture is heavily stirred at 20° C. for 18h. Additional acetic acid anhydride (0.8 mmol, 75 mL) and THF (2.5 mL) are added. After 2 h the reaction mixture is concentrated to 30 mL, and extracted with DCM (2×20 mL). The combined organic phases are concentrated in vacuo, and the crude product is purified on silica (35 g) using 10% ammonia in ethanol and DCM (7:3) as eluent to give the monoactylated compound.

Example 26

(2E)-5-Amino-5-methylhex-2-enoic acid N-((1R)-1-{N-[(1R)-1-(((1S)-5-acetylamino-1-carbamoylpentyl)carbamoyl)-2-phenylethyl]-N-methylcarbamoyl}-2-(2-naphthyl)ethyl)amide.

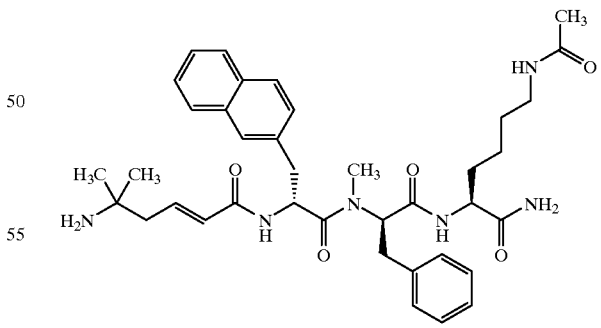

This compound was prepared by acetylation of the epsilon amino group in the lysine fragment using the general method described above and using the compound prepared in example 19 as starting material.
HPLC: Rt=19.4 min (method A)
  Rt=31.5 min (method A1)
ESMS: M+1=671.4

Example 27

(2E)-5-Amino-5-methylhex-2-enoic acid N-((1R)-1-{N-[(1R)-1-(((1S)-5-acetylamino-1-carbamoylpentyl)carbamoyl)-2-(2-thienyl)ethyl]-N-methylcarbamoyl}-2-(biphenyl-4-yl)ethyl)amide:

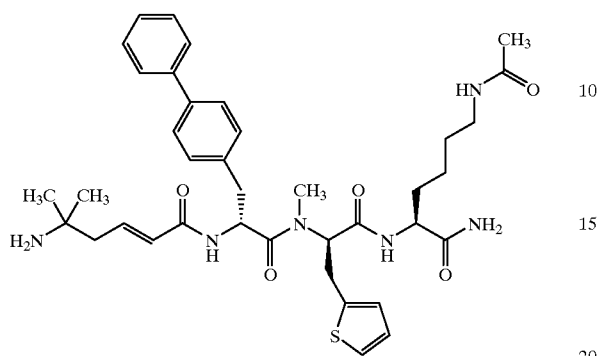

This compound was prepared by acetylation of the epsilon amino group in the lysine fragment using the general method described above and using the compound prepared in example 24 as starting material.
HPLC: Rt=21.0 min (method A)
Rt=33.6 min (method A1)
ESMS: M+1=703.4

Example 28

(2E)-5-Amino-5-methylhex-2-enoic acid N-((1R)-1-{N-[(1R)-1-(((1S)-5-acetylamino-1-carbamoylpentyl)carbamoyl)-2-phenylethyl]-N-methylcarbamoyl)-2-(biphenyl-4-yl)ethyl)amide:

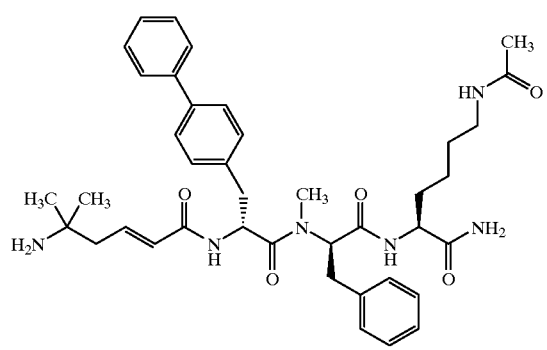

This compound was prepared by acetylation of the epsilon amino group in the lysine fragment using the general method described above and using the compound prepared in example 20 as starting material.

HPLC: Rt=21.2 min (method A)
Rt=33.9 min (method A1)
ESMS: M+1=697.4

Example 29

(2E)-5-Amino-5-methylhex-2-enoic acid N-((1R)-1-{N-[(1R)-1-((1S)-5-acetylamino-1-carbamoylpentylcarbamoyl)-2-(2-thienyl)ethyl]-N-methylcarbamoyl}-2-(2-naphthyl)ethyl}amide:

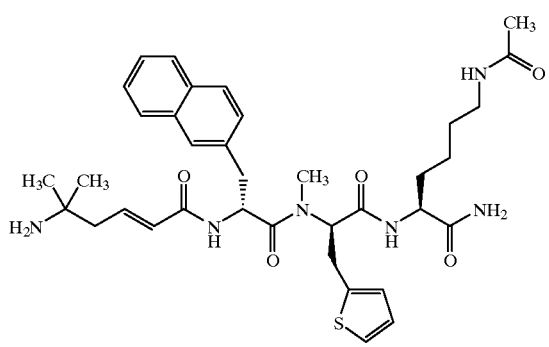

This compound was prepared by acetylation of the epsilon amino group in the lysine fragment using the general method described above and using the compound prepared in example 22 as starting material.

HPLC: Rt=19.5 min (method A)
Rt=30.4 min (method A1)
ESMS: M+1=677.2

The following examples (30–33) were prepared on solid support using the general procedure described below:

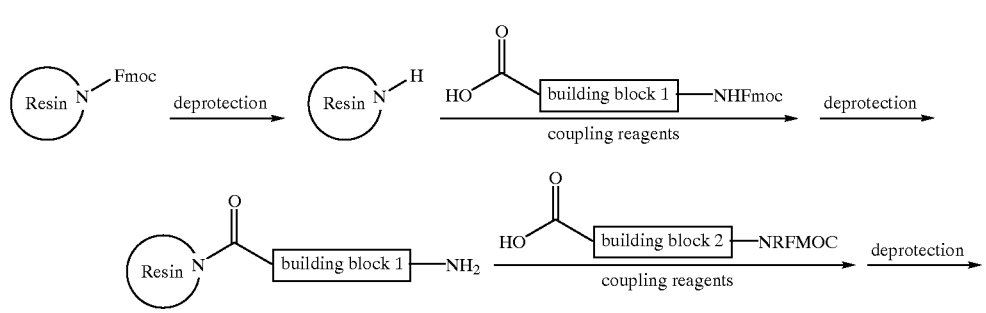

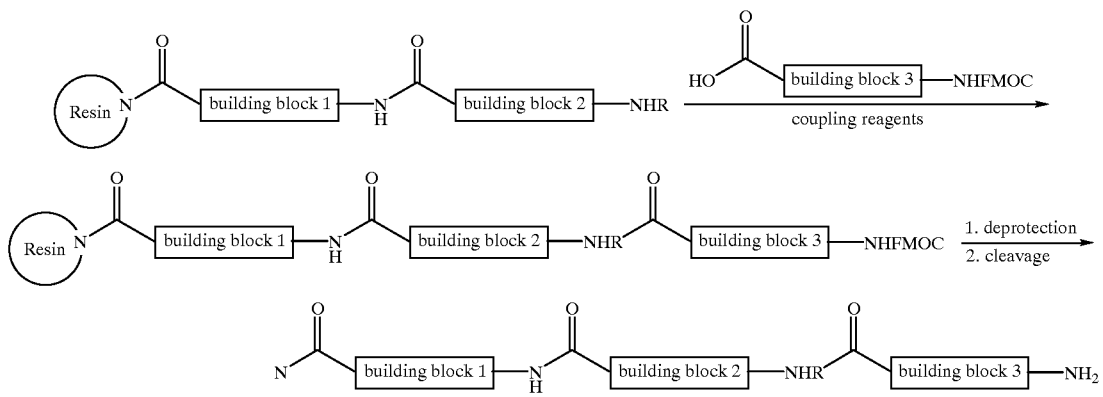

Fmoc deprotection procedure:

The resin is swelled and shaken in 20% piperidine in DMF (5 ml) for 3 min. The resin is drained and the deprotection process is repeated, with 15 min reaction time.

Standard washing procedure:

The drained resin is washed using the following standard washing procedure: The resin is repeatedly swelled, shaken and drained three times with 5 mL of DMF, methylene chloride, DMF, 2-propanol, methanol and finally with diethyl ether Standard protocol for solid phase synthesis of example 30–33.

Deprotection:

Commercial diaminoalkyltrityl resins (Novabiochem 01-64-0082, 01-64-0083, 01-64-0081 and 01-34-0132) were employed using the method described above and below.

Attachment of building block 1 (FMOC-N-Me-D-Phe-OH):

Building block 1 (0.9 mmol), HOBt (138 mg, 0.9 mmol) and EDAC (173 mg, 0.9 mmol) is mixed in DMF (2 mL) for 15 min, and then transferred to the drained resin, followed by addition of DMF (3 mL). DIPEA (116 mg, 0.9 mmol) is added after 30 min, and the reaction mixture is shaken for 20 h.

The resin is drained and the washed using the standard procedure described above. The resin is deprotected using the method described above followed by the standard washing procedure.

Attachment of building block 2 (Fmoc-N-Me-D-Bip-OH):

Building block 2 (0.9 mmol), HOAt (137 mg, 0.9 mmol) and EDAC (173 mg, 0.9 mmol) is mixed in DMF (2 mL) for 15 min, and then transferred to the drained resin followed by addition of DMF (3 mL). DIPEA (116 mg, 0.9 mmol) is added after 30 min, and the reaction mixture is shaken for 20 h.

The resin is drained and the washed using the standard procedure described above. The resin is deprotected using the method described above followed by the standard washing procedure.

Attachment of buildingblock 3 (FMOC-AEH-OH)

Building block 3 (0.9 mmol), HOAt (138 mg, 0.9 mmol) and EDAC (173 mg, 0.9 mmol) is mixed in DMF (2 mL) for 15 min, and then transferred to the drained resin, followed by addition of DMF (3 mL). DIEA (1.16 mg, 0.9 mmol) is added after 30 min, and the reaction mixture is shaken for 20 h.

The resin is drained and washed using the standard procedure described above. The resin is deprotected using the method described above followed by the standard washing procedure.

Detachment of compound from the resin:

The resin which has been treated as described above is swelled and shaken in a mixture of 5% triflouroacetic acid in DCM for 30 min. The resin is then drained and the procedure is repeated. All drained solutions are combined and concentrated in vacuo. Using this procedure and FMOC-N-Me-D-Phe-OH and FMOC-N-Me-D-Bip-OH and FMOC-AMH as building blocks, the following four compounds were synthesised:

Example 30

(2)-5-Amino-5-methylhex-2-enoic acid N-((1R)-1-{N-[(1R)-1-(6-aminohexylcarbamoyl)-2-phenylethyl]-N-methylcarbamoyl}-2-(biphenyl-4-yl)ethyl)-N-methylamide

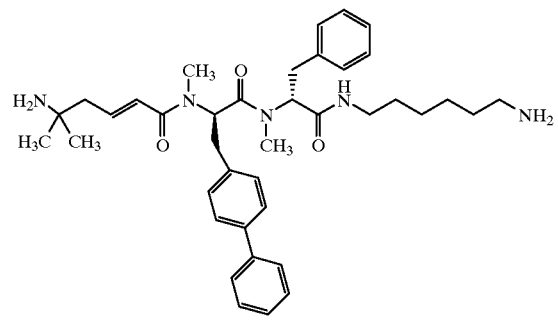

Diaminohexyl trityl resin was employed.

MS(ES): m/z 640.2 (M+H)$^+$.

Example 31

(2E)-5-Amino-5-methylhex-2-enoic acid N-((1R)-1-{N-[(1R)-1-(4-aminobutylcarbamoyl)-2-phenylethyl]-N-methylcarbamoyl)-2-(biphenyl-4-yl)ethyl)-N-methylamide

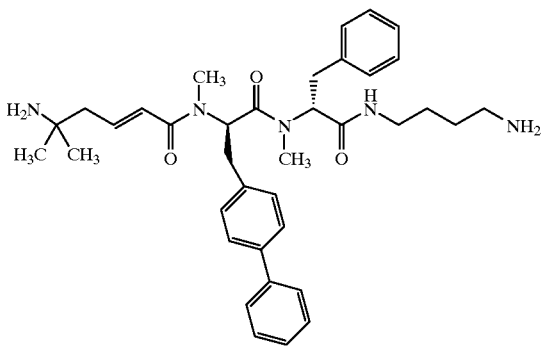

Diaminobutyl trityl resin was employed.
MS(ES): m/z 612.2 (M+H)+.

Example 32

(2E)-5-Amino-5-methylhex-2-enoic acid N-((1R)-1-{N-[(1R)-1-(3-aminopropylcarbamoyl)-2-phenylethyl]-N-methylcarbamoyl}-2-(biphenyl-4-yl)ethyl)-N-methylamide

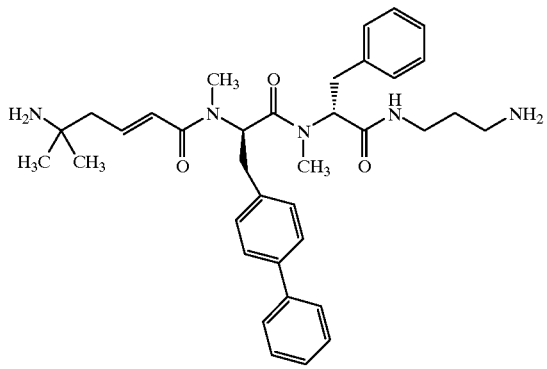

Diaminopropyl trityl resin was employed.
MS(ES): m/z 598.2 (M+H)+.

Example 33

(2E)-5-Amino-5-methylhex-2-enoic acid N-((1R)-1-{N-[(1R)-1-(2-aminoethylcarbamoyl)-2-phenylethyl]-N-methylcarbamoyl}-2-(biphenyl-4-yl)ethyl)-N-methylamide

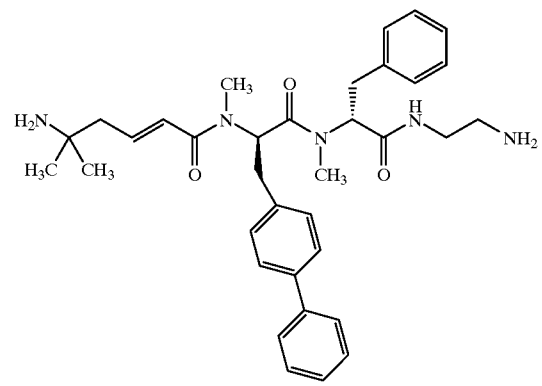

Diaminoethyl trityl resin was employed.
MS(ES): m/z 584.2 (M+H)+.

Example 34

3-(1-Aminoethyl)-N-((1R)-1-(N-((1R)-1-(N-(3-dimethylaminopropyl)-N-methylcarbamoyl)-2-phenylethyl)-N-methylcarbamoyl)-2-(2-naphthyl)ethyl)-N-methylbenzamide

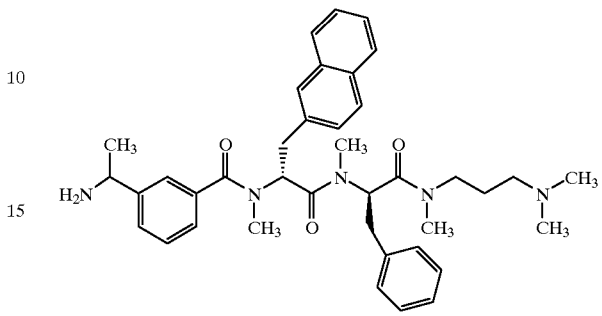

The title compound was prepared as in example 1, omitting acidic washes and using N-methyl-N'-dimethyldiaminopropane as the starting material. Buildingblock 7 and Boc-N-Me-D-2-Nal-OH was employed. The two stereoisomers could not be separated by HPLC. However buildingblock 7 was readily separated into two enantiomers by chiral HPLC and by repeating the procedure above the two stereoisomers were obtained.

| EA: (+1H$_2$O) Calc. for C39H51N5O4: | C: 71.55%; H: 7.80%; N: 10.70% |
|---|---|
| Found: | C: 71.32%; H: 7.86%; N: 10.70% |

$^1$H-NMR: ((CDCl$_3$; selected peaks for major rotamer): d 1.31 (d, 3H); 2.15 (s, 6H); 2.30 (s, 3H); 2.32 (s, 3H); 3.00 (s, 3H)

HPLC: (method A1): R$_t$=29.16 min.
MS(ES): m/z (M+H)+.

Example 35

3-(1-Aminoethyl)-N-((1R)-1-(N-((1R)-1-(N-((dimethylcarbamoyl)methyl)-N-methylcarbamoyl)-2-phenylethyl)-N-methylcarbamoyl)-2-(2-naphthyl)ethyl)-N-methylbenzamide.

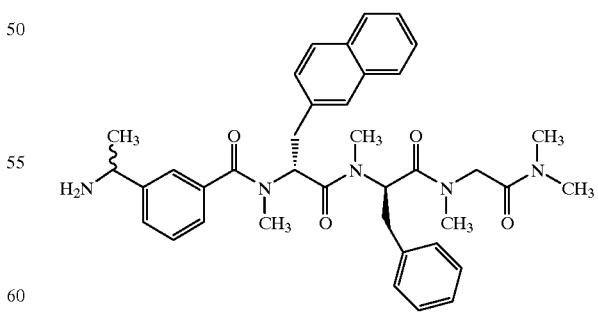

The title compound was prepared as in example 1 using sarcosine dimethyl amide instead of ((5S)-5-Amino-5-carbamoylpentyl)carbamic acid 2,2,2-trichloroethyl ester hydrochloride. Boc-N-Me-D-Phe-OH, Boc-N-Me-D-2-Nal-OH and buildingblock 7 were used as starting materials.

¹H-NMR: ((CDCl₃; selected peaks for major rotamer): d 1.40 (d, 3H); 2.90 (1, 6H); 3.07 (s, 3H); 5.71 (dd, 1H); 5.89 (dd, 1H); 5.95 (dd, 2H)

HPLC: (method A1): R_t=31.98 min.

MS(ES): m/z (M+H)⁺.

Example 36

(2S)-6-Acetylamino-2-((2R)-2-{(2R)-2-[(2S)-2-(2-amino-2-methylpropionylamino)-3-(imidazol-4-yl)propionylamino]-3-(2-naphthyl)propionylamino}-3-phenylpropionylamino)hexanoic acid amide

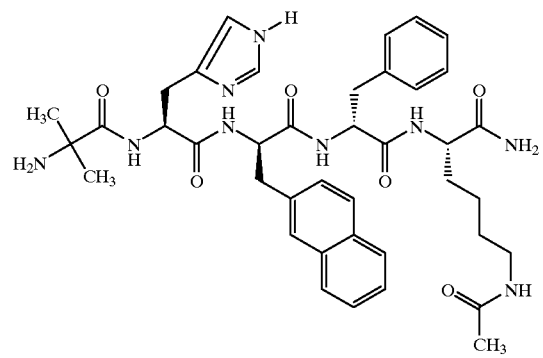

(2S)-6-Amino-2-((2R)-2-(2R)-2-[(2S)-2-(2-amino-2-methylpropionylamino)-3-(3H-imidazol-4-yl)propionylamino]-3-(2-naphthyl)propionylamino}-3-phenylpropionylamino)hexanoic acid amide (200 mg, 0.28 mmol) (prepared as in WO9517423) was suspended in DMF (10 ml) and DIEA (0.24 ml 1.4 mmole) and acetic anhydride (0.032 ml; 0.33 mmole) was added. The mixture was stirred for 20 h and was diluted with TFA in water (0.2%, 290 ml) and purified by preparative HPLC in three consecutive runs on a 25×250 mm 10 u RP-18 column at 40° C. with a gradient of 20–40% 0.1% TFA./acetonitrile in 0.1% aqueous TFA. The peptide containing fractions were pooled and lyophilised to afford 114 mg of the title compound.

HPLC (method A1) Rt=22.13 min (method B1) Rt=24.60 min

ESMS: m/z 754.2 (M+H)⁺

Example 37

(2S)-5-Ureido-2-((2R)-2-{(2R)-2-[(2S)-2-(2-amino-2-methylpropionylamino)-3-(3H-imidazol-4-yl)propionylamino]-3-(2-naphthyl)propionylamino}-3-phenylpropionylamino)pentanoic acid amide

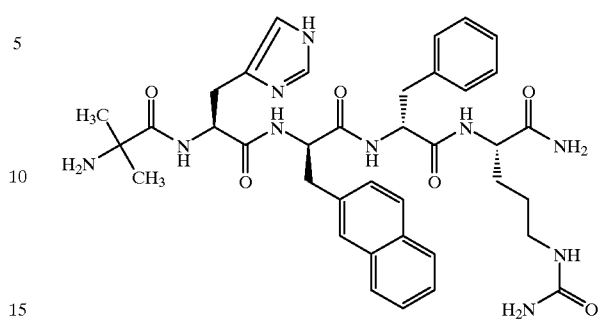

The title compound was prepared as in WO9517423 starting from FMOC-citruline-OH (Bachem B2090).

HPLC (method A1) Rt=20.83 min (method B1) Rt=22.97 min

ESMS: m/z 742.0 (M+H)⁺

Example 38

(2S)-6-tert Butyloxycarbonylamino-2-((2R)-2-{(2R)-2-[(2S)-2-(2-amino-2-methylpropionylamino}-3-(imidazol-4-yl)propionylamino]-3-(2-naphthyl)propionylamino)-3-phenylpropionylamino)hexanoic acid amide

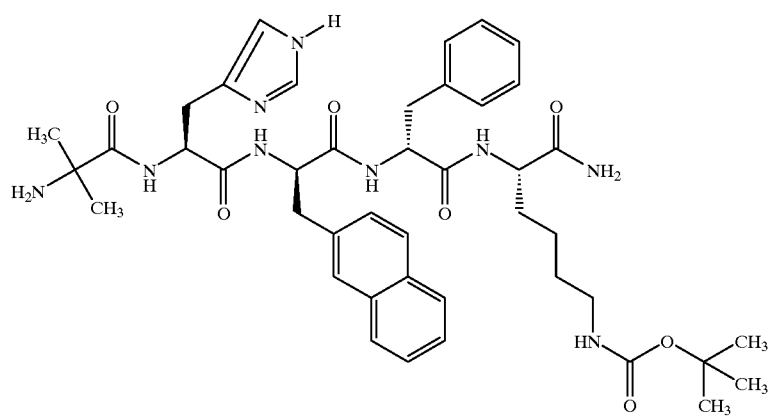

(2S)-6-Amino-2-((2R)-2-{(2R)-2-[(2S)-2-(2-amino-2-methylpropionylamino)-3-(3H-imidazol-4-yl)propionylamino]-3-(2-naphthyl)propionylamino}-3-phenylpropionylamino)hexanoic acid amide (712 mg, 1.0 mmol) (prepared as in WO9517423) was suspended in water (10 ml) and di-tert-butyldicarbonate (240 mg, 1.0 mmol) was added. The mixture was stirred for 20 h and was diluted with TFA in water (0.2%, 185 ml) and purified on a Sep-Pac (Waters #36925) RP-18 column washed with 28% acetonitrile in 0.1% aqueous TFA and eluted with 35% acetonitrile in 0.1% aqueous TFA. The peptide containing fractions were pooled, diluted and lyophilised to afford 408 mg of the title compound.

HPLC (method A1) Rt=30.53 min (method B1) Rt=32.75 min

ES-MS: m/z 812.8 (M+H)⁺

Example 39

(2S)-6-Acetylamino-2-((2R)-2-{N-((2R)-2-[(2S)-2-(2-amino-2-methylpropionylamino)-3-(imidazol-4-yl)propionylamino]-3-(2-naphthyl)propionyl)-N-methylamino}-3-phenylpropionylamino)hexanoic acid amide

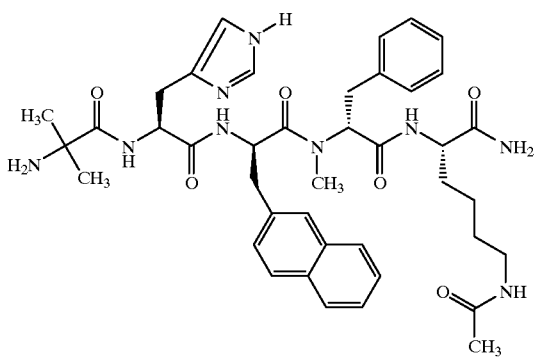

The title compound was prepared as in example 36.
HPLC (method A1) Rt=26.38 min
(method B1) Rt=28.70 min
ESMS: m/z 769.1 (M+H)$^+$

Example 40

(2S)-6-(3a,7a,12a-trihydroxy-5b-cholanoylamino)-2-((2R)-2-{(2R)-2-[(2S)-2-(2-amino-2-methylpropionylamino)-3-(3H-imidazol-4-yl)propionylamino]-3-(2-naphthyl)propionylamino}-3-phenylpropionylamino)hexanoic acid amide

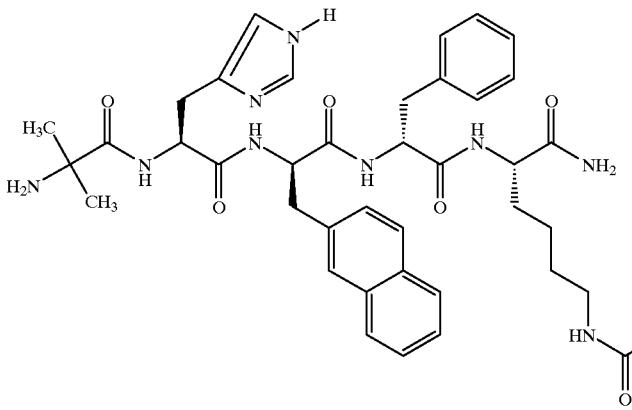

3a,7a,12a-trihydroxy-5b-cholanic acid (409 mg; 1 mmole) and HOBt (153 mg; 1 mmole were dissolved in DMF (7 ml) and EDAC (192 mg, 1 mmole) were added and the mixture was stirred for 15 min. (2S)-6-Amino-2-((2R)-2-{(2R)-2-[(2S)-2-(2-amino-2-methylpropionylamino)-3-(3H-imidazol-4-yl)propionylamino]-3-(2-naphthyl)propionylamino}-3-phenylpropionylamino)hexanoic acid amide (712 mg, 1.0 mmol) (prepared as described in WO9517423) was added and the mixture was stirred for 20 h and was diluted with TFA in water (0.2%, 100 ml) and purified on a Sep-Pac (Waters #43345) RP-18 column washed with 35% acetonitrile in 0.1% aqueous TFA and eluted with 55% acetonitrile in 0.1% aqueous TFA. The peptide containing fractions were pooled, diluted and lyophilised to afford 803 mg of the title compound.
HPLC (method A1) Rt=35.43 min
(method B1) Rt=37.97 min
ES-MS: m/z 1103.0 (M+H)$^+$

Example 41

(2E)-5-Amino-5-methylhex-2-enoic acid ((1R)-1-{N-[(1R)-1-(5-aminopentylcarbamoyl)-2-phenylethyl]-N-methylcarbamoyl}-2-(2-naphthyl)ethyl)amide

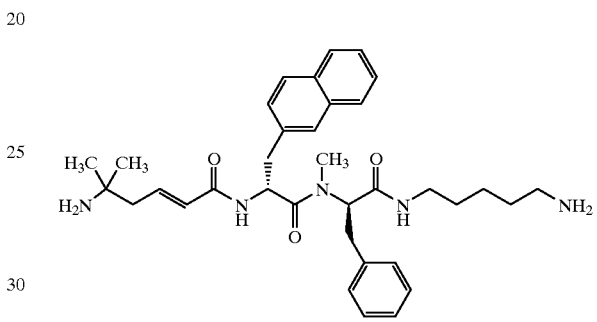

The title compound was prepared as in example 1 using the appropriate amine and the buildingblocks listed previously.
HPLC: (method A1): R$_t$=28.08 min.
(method B1): R$_t$=29.05 min.

Example 42

(2E)-5-Amino-5-methylhex-2-enoic acid N-((1R)-1-{N-[(1R)-1-(5-aminopentylcarbamoyl)-2-phenylethyl]-N-methylcarbamoyl}-2-(2-naphthyl)ethyl)-N-methylamide

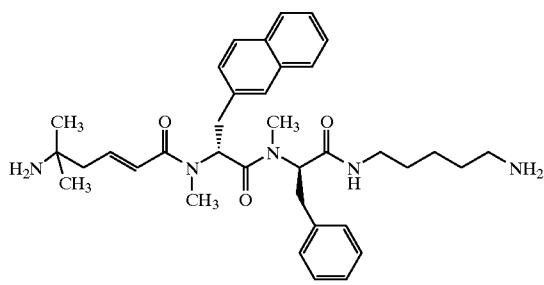

The title compound was prepared as in example 1 using the appropriate amine and the buildingblocks listed previously.
HPLC: (method A1): $R_t$=27.30 min.
MS(ES): m/z 600.2 (M+H)$^+$.

Example 43

N-((1R)-1-{N-[(1R)-1-(4-Aminobutylcarbamoyl)-2-phenylethyl]-N-methylcarbamoyl}-2-(biphenyl-4-yl)ethyl)-3-aminomethyl-N-methylbenzamide

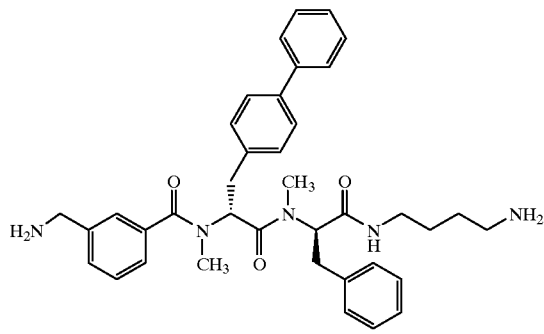

The title compound was prepared as in example 1 using the appropriate amine and the buildingblocks listed previously.
HPLC: (method A1): $R_t$=30.40 min.
MS(ES): m./z 620.4 (M+H)$^+$.

Example 44

3-Aminomethyl-N-(1R)-1-{N-[(1R)-1-(5-aminopentylcarbamoyl)-2-phenylethyl]-N-methylcarbamoyl}-2-(2-naphthyl)ethyl)benzamide

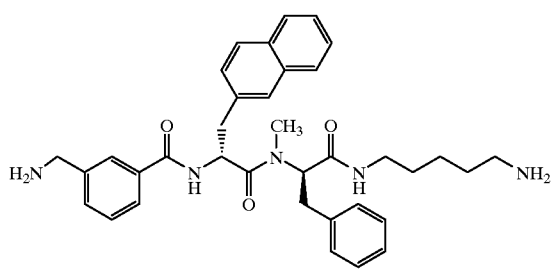

The title compound was prepared as in example 1 using the appropriate amine and the buildingblocks listed previously.

HPLC: (method A1): $R_t$=28.47 min.
(method B1): $R_t$=29.95 min.
MS(ES): m/z 594.4 (M+H)$^+$.

Example 45

3-Aminomethyl-N-((1R)-1-{N-[(1R)-1-(5-aminopentylcarbamoyl)-2-phenylethyl]-N-methylcarbamoyl)-2-(2-naphthyl)ethyl)-N-methylbenzamide

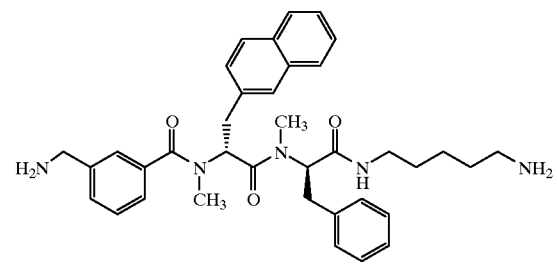

The title compound was prepared as in example 1 using the appropriate amine and the buildingblocks listed previously.
HPLC: (method A1): $R_t$=27.53 min.
MS(ES): m/z 608.4 (M+H)$^+$.

Example 46

(2E)-5-Amino-5-methylhex-2-enoic acid N-((1R)-1-{N-[(1R)-1-((4-dimethylaminobutyl)carbamoyl)-2-phenylethyl]-N-methylcarbamoyl}-2-(2-naphthyl)ethyl)-N-methylamide

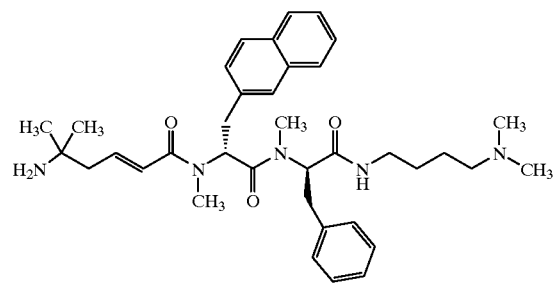

The title compound was prepared as in example 1 using the appropriate amine and the buildingblocks listed previously.
HPLC: (method A1): $R_t$=28.02 min.
MS(ES): m/z 614.7 (M+H)$^+$.

Example 47

(2E)-5-Amino-5-methylhex-2-enoic acid N-((1R)-1-{N-[(1R)-1-(5-guanidinopentylcarbamoyl)-2-phenylethyl]-N-methylcarbamoyl}-2-(2-naphthyl)ethyl)-N-methylamide

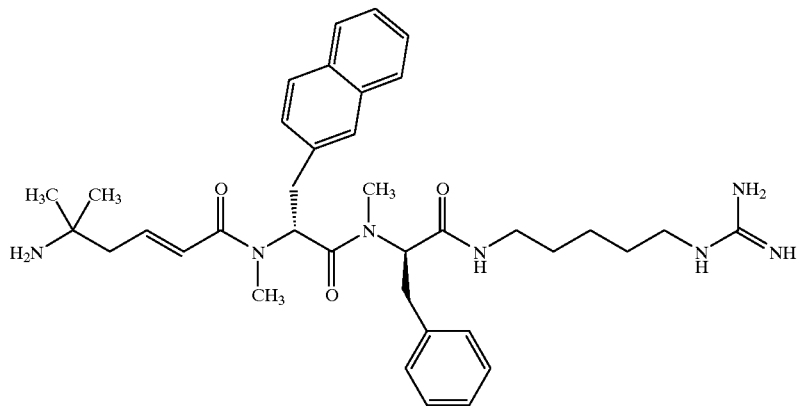

The title compound was prepared as in example 1 using the appropriate amine and the buildingblocks listed previously.

HPLC: (method A1): $R_t$=25.27 min.
MS(ES): m/z 642.6 (M+H)$^+$.

Example 48

(2E)-5-Amino-5-methylhex-2-enoic acid N-[(1R)-1-(N-{(1R)-1-[5-(3-ethylureido)pentylcarbamoyl]-2-phenylethyl}-N-methylcarbamoyl)-2-(2-naphthyl)ethyl]-N-methylamide

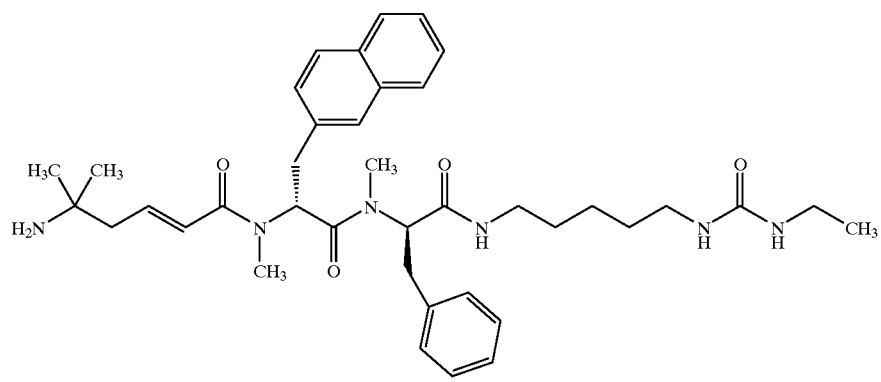

The title compound was prepared as in example 1 using the appropriate amine and the buildingblocks listed previously.

HPLC: (method A1): $R_t$=29.62 min.
(method B1): $R_t$=31.65 min.
MS(ES): m/z 672.4 (M+H)$^+$.

Example 49

3-Aminomethyl-N-[(1R)-1-(N-{(1R)-1-[N-(2-(dimethylamino)ethyl)-N-methylcarbamoyl]-2-phenylethyl}-N-methylcarbamoyl)-2-(2-naphthyl)ethyl]-N-methylbenzamide

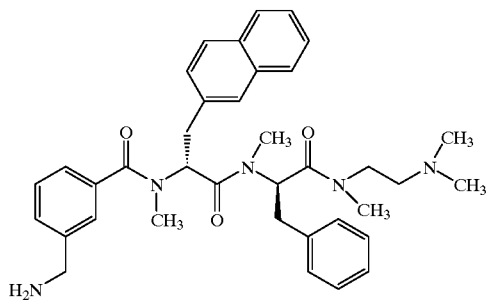

The title compound was prepared as in example 1 using the appropriate amine and the buildingblocks listed previously.

HPLC: (method A1): $R_t$=26.33 min.
(method B1): $R_t$=29.08 min.
MS(ES): m/z 608.4 (M+H)$^+$.

Example 50

N-[(1R)-1-(N-{(1R)-1-[N-(2-(Dimethylamino)ethyl)-N-methylcarbamoyl]-2-phenylethyl}-N-methylcarbamoyl)-2-(2-naphthyl)ethyl]-N-methyl-3-(methylaminomethyl)benzamide

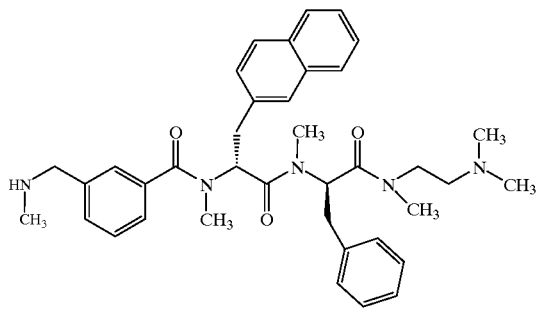

The title compound was prepared as in example 1 using the appropriate amine and the buildingblocks listed previously.

HPLC: (method A1): $R_t$=26.68 min.

(method B1): $R_t$=29.25 min.
MS(ES): m/z 622.4 (M+H)$^+$.

Example 51

3-((1R/S)-1-Aminoethyl)-N-[(1R)-1-(N-{(1R)-1-[N-(2-(dimethylamino)ethyl)-N-methylcarbamoyl]-2-phenylethyl}-N-methylcarbamoyl)-2-(2-naphthyl)ethyl]-N-methylbenzamide

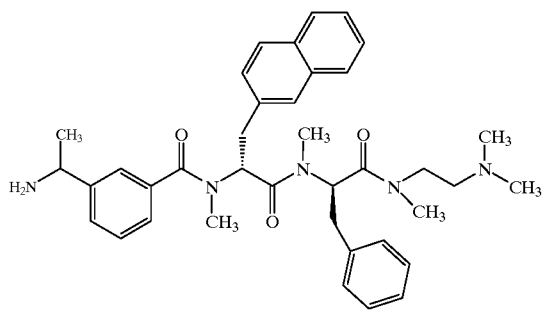

The title compound was prepared as in example 1 using the appropriate amine and the buildingblocks listed previously.

HPLC: (method A1): $R_t$=27.30 min.

(method B1): $R_t$=29.87 min.
MS(ES): m/z 622.0 (M+H)$^+$.

Example 52

(2E)-5-Amino-5-methylhex-2-enoic acid N-((1R)-2-(biphenyl-4-yl)-1-{N-[(1R)-1-(4-(dimethylamino)butylcarbamoyl)-2-phenylethyl]-N-methylcarbamoyl}ethyl)-N-methylamide

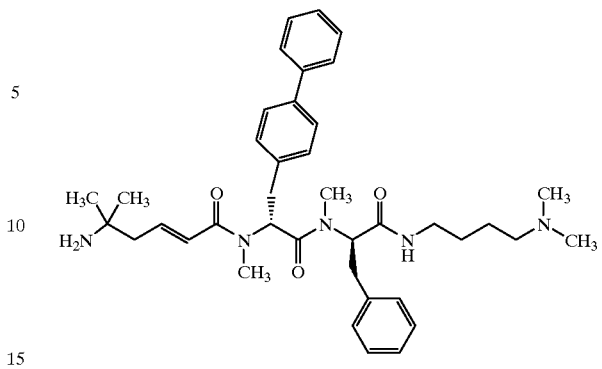

The title compound was prepared as in example 1 using the appropriate amine and the buildingblocks listed previously.

HPLC: (method A1): $R_t$=30.92 min.
MS(ES): m/z 640.6 (M+H)$^+$.

Example 53

(2E)-5-Amino-5-methylhex-2-enoic acid N-[(1R)-1-(N-{(1R)-1-[N-(2-dimethylaminoethyl)-N-methylcarbamoyl]-2-phenylethyl}-N-methylcarbamoyl)-2-(2-naphthyl)ethyl]-N-methylamide

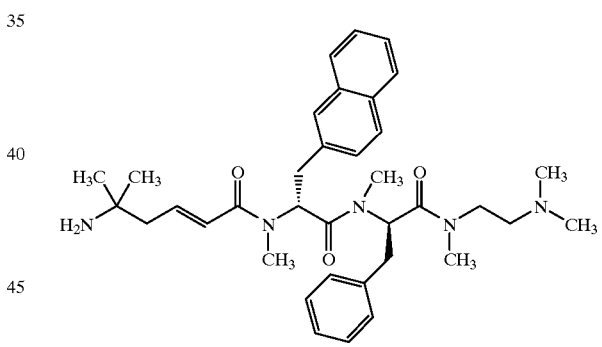

The title compound was prepared as in example 1 using the appropriate amine and the buildingblocks listed previously.

HPLC: (method A1): $R_t$=26.43 min.

(method B1): $R_t$=29.02 min.
MS(ES): m/z 600.2 (M+H)$^+$.

Example 54

(2E)-5-Amino-5-methylhex-2-enoic acid N-((1R)-1-{N-[(1R)-1-((4-dimethylaminobutyl)carbamoyl)-2-(2-thienyl)ethyl]-N-methylcarbamoyl}-2-(2-naphthyl)ethyl)-N-methylamide

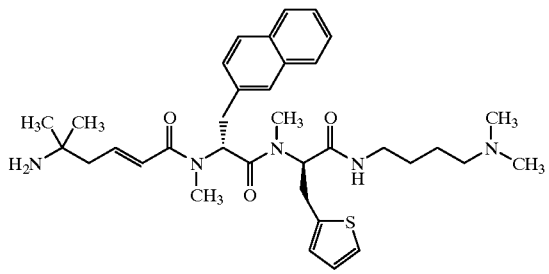

The title compound was prepared as in example 1 using the appropriate amine and the buildingblocks listed previously.

HPLC: (method A1): $R_t$=27.30 min.

(method B1): $R_t$=29.39 min.

MS(ES): m/z 620.4 (M+H)$^+$.

Example 55

(2 E)-5-Amino-5-methylhex-2-enoic acid N-((1R)-2-(4-biphenyl-4-yl)-1-{N-[(1R)-1-((4-dimethylaminobutyl)carbamoyl)-2-(2-thienyl)ethyl]-N-methylcarbamoyl}ethyl)-N-methylamide

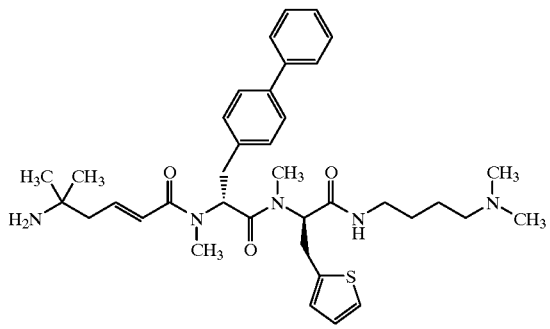

The title compound was prepared as in example 1 using the appropriate amine and the buildingblocks listed previously.

HPLC: (method A1): $R_t$=30.23 min.

(method B1): $R_t$=32.27 min.

MS(ES): m/z 646.4 (M+H)$^+$.

Example 56

(2E)-5-Amino-5-methylhex-2-enoic acid N-((1R)-1-{N-[(1R)-1-((1S)-5-(acetylamino)-1-(dimethylcarbamoyl)pentylcarbamoyl)-2-phenylethyl]-N-methylcarbamoyl}2-(2- naphthyl)ethyl)-N-methylamide

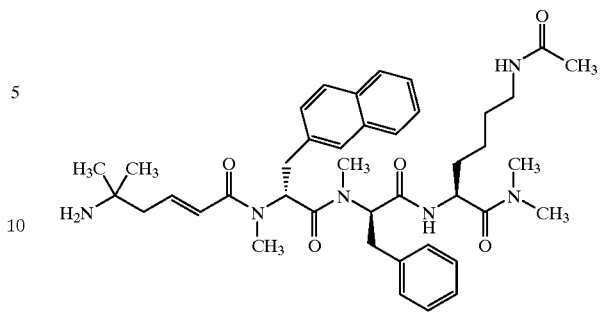

((1S)-5-Acetylamino-1-(dimethylcarbamoyl)pentyl)carbamic acid tert-butyl ester

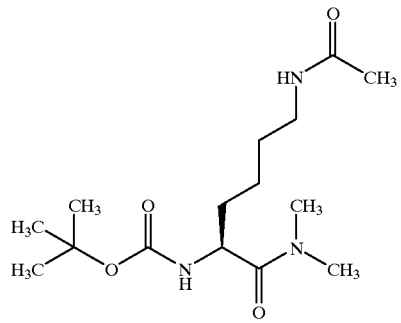

(2S)-6-Acetylamino-2-(tert-butoxycarbonylamino) hexanoic acid (Purchased at Bachem, 5.0 g, 17.3 mmol) was dissolved in dichloromethane (100 ml) and N,N-dimethylformamide (50 ml). 1-Hydroxybenzotriazole hydrate (2.65 g, 17.3 mmol) was added. The solution was cooled to 0° C. N-(3-Dimethylaminopropyl)-N'-ethylcarbodiimide hydrochloride (3.32 g, 17.3 mmol) was added. The reaction mixture was stirred for 20 min at 0° C. A 33% solution or dimethylamine in methanol (16.4 ml, 121 mmol) was added. The reaction mixture was stirred for 16 h, while it was warming up to room temperature. It was diluted with ethyl acetate (250 ml) and washed with a 10% aqueous solution of sodium hydrogensulfate (200 ml). The aqueous phase was extracted with ethyl acetate (2×100 ml). The combined organic layers were washed with a saturated aqueous solution of sodium hydrogen carbonate (200 ml) and dried over magnesium sulfate. The solvent was removed. The crude product was purified by flash chromatography on silica (120 g), using dichloromethane/methanol (10:1) as eluent to give 3.00 g of ((1S)-5-acetylamino-1-(dimethylcarbamoyl)pentyl)carbamic acid tert-butyl ester.

$^1$H-NMR (CDCl$_3$): d 1.49 (s, 9H); 1.34–1.75 (m, 6H); 1.97 (m, 3H); 2.96 (s, 3H); 3.07 (s, 3 H); 3.23 (m, 2H); 4.60 (m, 1H); 4.99 (br d, 1H); 5.83 (br, 1H).

(2S)-6-Acetylamino-2-aminohexanoic acid dimethylamide

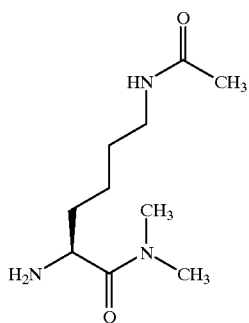

((1S)-5-Acetylamino-1-(dimethylcarbamoyl)pentyl) carbamic acid tert-butyl ester was dissolved in a solution of 3.1 M hydrogen chloride in ethyl acetate (15 ml, 46 mmol). The mixture was stirred for 1 h at room temperature. The solid was isolated by filtration and dried in vacuo to give 1.86 g of the hydrochloride salt of (2S)-6-acetylamino-2-aminohexanoic acid dimethylamide as crude product, which was used without further purification.

$^1$H-NMR (DMSO-d$_6$, selected values): d 1.39 (m, 4H); 2.92 (s, 3H); 3.04 (s, 3H).

N-[(1R)-1-((1S)-5-(Acetylamino)-1-(dimethylcarbamoyl)pentylcarbamoyl)-2-phenylethyl]-N-methylcarbamic acid tert-butyl ester

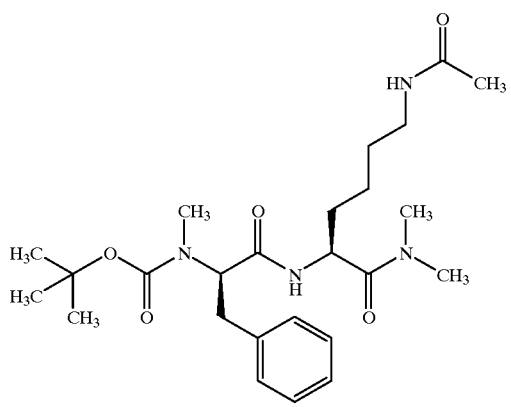

N-(3-Dimethylaminopropyl)-N'-ethylcarbodiimide hydrochloride (824 mg, 4.30 mmol) was added at 0° C. to a solution of (2R)-2-(N-(tert-butoxycarbonyl)-N-methylamino)-3-phenylpropionic acid (1.20 g, 4.30 mmol) and 1-hydroxybenzotriazole hydrate (659 mg, 4.30 mmol) in dichloromethane (15 ml) and N,N-dimethylformamide (15 ml). The reaction mixture was stirred for 20 min at 0° C. A solution of the hydrochloride salt of (2S)-6-acetylamino-2-aminohexanoic acid dimethylamide (1.86 g, 6.44 mmol) in N,N-dimethylformamide (10 ml) was added. Ethyidiisopropylamine (2.98 ml, 17.2 mmol) was added. The reaction mixture was stirred for 16 h, while it was warming up to room temperature. The reaction mixture was diluted with ethyl acetate (150 ml) and washed with a 10% aqueous solution of sodium hydrogen sulfate (200 ml). The aqueous solution was extracted with ethyl acetate (2×100 ml). The combined organic layers were washed with a saturated aqueous solution of sodium hydrogen carbonate (200 ml) and dried over magnesium sulfate. The solvent was removed. The crude product was purified by flash chromatography on silica (60 g), using dichloromethane/methanol (10:1) as eluent to give 1.81 g of N-[(1R)-1-((1S)-5-(acetylamino)-1-(dimethylcarbamoyl)pentylcarbamoyl)-2-phenylethyl]-N-methylcarbamic acid tert-butyl ester.

$^1$H-NMR (CDCl$_3$, selected values): d 1.31 (br, 9H); 1.55 (m, 4H); 1.81 and 1.97 (both s, together 3H); 4.76, 4.91, and 6.02 (all m, together 2H).

(2S)-6-Acetylamino-2-(((2R)-2-(methylamino)-3-phenylpropionyl)amino)hexanoic acid dimethylamide

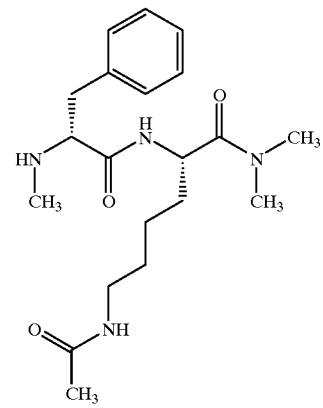

N-[(1R)-1-((1S)-5-(Acetylamino)-1-(dimethylcarbamoyl)pentylcarbamoyl)-2-phenylethyl]-N-methylcarbamic acid tert-butyl ester (1.44 g, 3.02 mmol) were dissolved in ethyl acetate (5 ml). A 3.1 M solution of hydrogen chloride in ethyl acetate (40 ml, 124 mmol) was added. The reaction mixture was stirred for 1.5 h. The liquid was removed by decantation. The solid was washed with ethyl acetate (50 ml) and dried in vacuo to give 1.34 g of the hydrochloride salt of crude (2S)-6-acetylamino-2-(((2R)-2-(methylamino)-3-phenylpropionyl)amino)-hexanoic acid dimethylamide, which was used for the next step without purification.

$^1$H-NMR (DMSO-d$_6$, selected values): d 0.90 (m, 2H); 1.21 (m, 4H); 1.80 (s, 3H); 3.27 (dd, 1H); 4.10 (m, 1H); 4.48 (m, 1H).

N-((1R)-1 N-[(1R)-1-((1S)-5-(Acetylamino)-1-(dimethylcarbamoyl)pentylcarbamoyl)-2-phenylethyl]-N-methylcarbamoyl}-2-(2-naphthyl)ethyl)-N-methylcarbamic acid tert-butyl ester

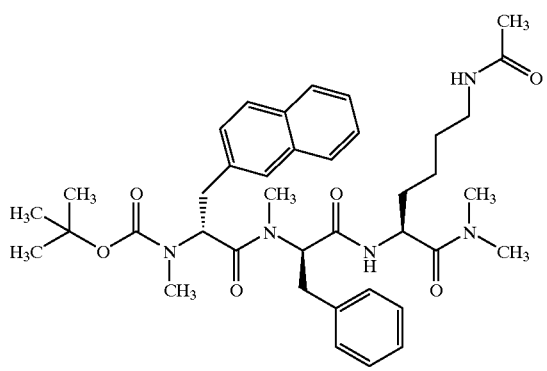

N-(3-Dimethylaminopropyl)-N'-ethylcarbodiimide hydrochloride (594 mg, 3.1 mmol) was added at 0° C. to a solution of (2R)-2-(N-(tert-butoxycarbonyl)-N-methylamino)-3-(2-naphthyl)propionic acid (1.02 g, 3.1 mmol) and 1-hydroxy-7-azabenzotriazole (422 mg, 3.1 mmol) in dichloromethane (10 ml) and N,N-dimethylformamide (5 ml). The reaction mixture was stirred for 20 min at 0° C. A solution of the hydrochloride salt of crude (2S)-6-acetylamino-2-(((2R)-2-(methylamino)-3-phenylpropionyl)amino)hexanoic acid dimethylamide (1.28 g, 3.1 mmol) in dichloromethane (20 ml)and N,N-dimethylformamide (10 ml) and ethyidiisopropylamine (1.59 ml, 9.3 mmol) were added subsequently. The reaction mixture was stirred for 16 h, while it was warming up to room temperature. It was diluted with ethyl acetate (200 ml) and washed with a 10% aqueous sodium hydrogen sulfate solution (150 ml). The aqueous solution was extracted wtih ethyl acetate (3×100 ml). The combined organic layers were washed with a saturated aqueous solution of sodium hydrogen carbonate (200 ml) and dried over magnesium sulfate. The solvent was removed in vacuo. The crude product was purified by flash chromatography on silica (120 g), usin dichloromethane/methanol (10:1) as eluent, to give 1.57 g of N-((1R)-1-{N-[(1R)-1-((1S)-5-(acetylamino)-1-(dimethylcarbamoyl)pentylcarbamoyl)-2-phenylethyl]-N-methylcarbamoyl}-2-(2-naphthyl)ethyl)-N-methylcarbamic acid tert-butyl ester.

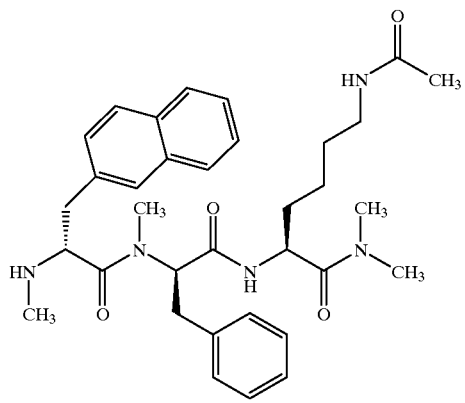

N-((1R)-1-{N-[(1R)-1-((1S)-5-(Acetylamino)-1-(dimethylcarbamoyl)pentylcarbamoyl)-2-phenylethyl]-N-methylcarbamoyl}-2-(2-naphthyl)ethyl)-N-methylcarbamic acid tert-butyl ester (1.56 g, 2.27 mmol) was dissolved in ethyl acetate (10 ml). A 3.1 M solution of hydrogen chloride (30 ml, 93 mmol) was added. The reaction mixture was stirred for 45 min. The solvent was removed by decanatation. The residue was washed with ethyl acetate (50 ml) and dried in vacuo to give 1.08 g of the crude hydrochloride salt of (2S)-6-acetylamino-2-{(2R)-2-[N-methyl-N-(2-(methylamino)-3-(2-naphthyl)propionyl)amino]-3-phenylpropionylamino}hexanoic acid N,N-dimethylamide, which was used for the next step without purification.

¹H-NMR (CDCl₃, selected values): d 0.86, 0.95, 1.20, 1.24, and 1.36 (all s, together 9H); 1.91, 1.99, 2.21, and 2.25 (all s, together 3H).

¹H-NMR (DMSO-d₆, selected values): d 1.93 and 2.00 (both s, together 3H); 5.55 (dd, 1H).

(2S)-6-Acetylamino-2-{(2R)-2-[N-m ethyl-N-(2-(methylamino)-3-(2-naphthyl)propionyl)amino]-3-phenylpropionylamino)hexanoic acid N,N-dimethylamide {(3E)4-[N-((1R)-1-{N-[(1R)-1-((1S)-5-Acetylamino-1-(dimethylcarbamoyl)pentylcarbamoyl)-2-phenylethyl]-N-methylcarbamoyl}-2-(2-naphthyl)ethyl)-N-methylcarbamoyl]-1,1-dimethylbut-3-enyl}carbamic acid tert-butyl ester

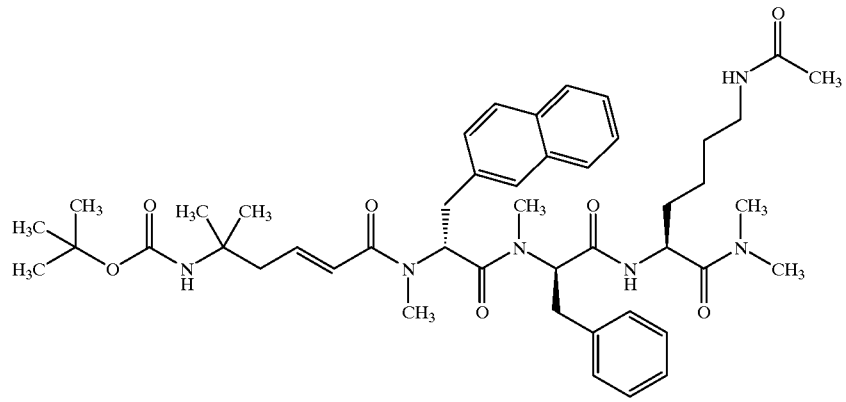

N-(3-Dimethylaminopropyl)-N'-ethylcarbodiimide hydrochloride (279 mg, 1.46 mmol) was added at 0° C. to a solution of (2E)-5-(tert-butyoxycarbonylamino)-5-methylhex-2-enoic acid (355 mg, 1.46 mmol) and 1-hydroxy-7-azabenzotriazole (199 mg, 1.46 mmol). The reaction mixture was stirred for 20 min at 0° C. A solution of the crude hydrochloride salt of (2S)-6-acetylamino-2-{(2R)-2-[N-methyl-N-(2-(methylamino)-3-(2-naphthyl)propionyl)amino]-3-phenylpropionylamino}hexanoic acid N,N-dimethylamide (857 mg, 1.46 mmol) in N,N-dimethylformamide (10 ml) and dichloromethane (20 ml) and ethyidiisopropylamine (0.75 ml, 4.38 mmol) were added subsequently. The reaction mixture was stirred for 16 h, while it was warming up to room temperature. It was diluted with ethyl acetate (200 ml) and washed wtih a 10% aqueous solution of sodium hydrogen sulfate (200 ml). The aqueous phase was extracted with ethyl acetate (2×100 ml). The combined organic layers were wshed with a saturated aqueous solution of sodium hydrogen carbonate (200 ml) and dried over magnesium sulfate. The solvent was removed in vacuo. The crude product was purified by flash chromatography on silica (120 g), using dichloromethane/methanol (10:1) as eluent, to give 719 mg of {(3E)4-[N-((1R)-1-{N-[(1R)-1-((1S)-5-acetylamino-1-(dimethylcarbamoyl) pentylcarbamoyl)-2-phenylethyl]-N-methylcarbamoyl}2-(2-naphthyl)ethyl)-N-methylcarbamoyl]-1,1-dimethylbut-3-enyl}carbamic acid tert-butyl ester.

¹H-NMR (CDCl₃, selected values): d 1.32 and 1.39 (both s, together 9H); 5.38 (m, 1H); 5.48 (m, 1H); 6.02 (d, 1H).

{(3E)-4-[N-((1R)-1-{N-[(1R)-1-((1S)-5-Acetylamino-1-(dimethylcarbamoyl)pentylcarbamoyl)-2-phenylethyl]-N-methylcarbamoyl}-2-(2-naphthyl)ethyl)-N-methylcarbamoyl]-1,1-dimethylbut-3-enyl}carbamic acid tert-butyl ester (897 mg, 1.10 mmol) was dissolved in dichloromethane (4 ml). The solution was cooled to 0° C. Trifluoroacetic acid (4 ml) was added. The reaction mixture was stirred for 35 min at 0° C. A saturated aqueous solution of sodium hydrogen carbonate (10 ml) was added. Solid sodium hydrogen carbonate was added until pH 7. Water (50 ml) and dichloromethane (30 ml) were added. The phases were separated. The aqueous phase was extracted with dichloromethane (5×40 ml). The combined organic layers were dried over magnesium sulfate. The solvent was removed in vacuo. The crude product was purified by flash chromatography on silica (120 g), using dichloromethane/methanol/25% aqueous ammonia (first: 100:10: 1, then 50:10:1), as eluent to give 408 mg of the title compound.

¹H-NMR (CDCl₃, selected values): d 1.08 and 1.09 (both s, together 6H); 2.90, 2.92, 3.04, and 3.07 (all s, together 12H); 6.06 (d, 1H).

HPLC: 32.07 min (A1).

34.0 min (B1).

LC-MS: 713.4 [M+1]⁺ at 9.54 min.

For biological testing, the title compound was transferred into its acetate salt by lyophilization with 0.5 M acetic acid (40 ml).

Example 57

(2E)-5-Amino-5-methylhex-2-enoic acid N-((1R)-1-{N-[(1R)-1-((1S)-5-acetylamino-1-(methylcarbamoyl) pentylcarbamoyl)-2-phenylethyl]-N-methylcarbamoyl}-2-(2-naphthyl)ethyl)-N-methylamide

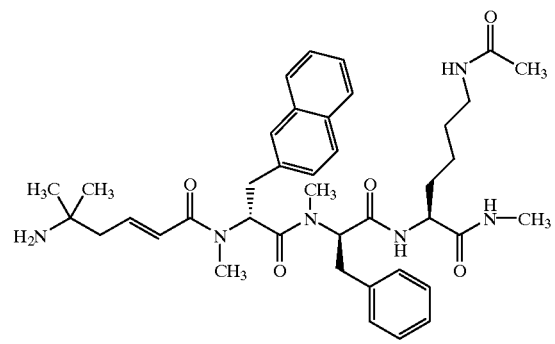

((1S)-5-(Acetylamino)-1-(methylcarbamoyl)pentyl) carbamic acid tert-butyl ester

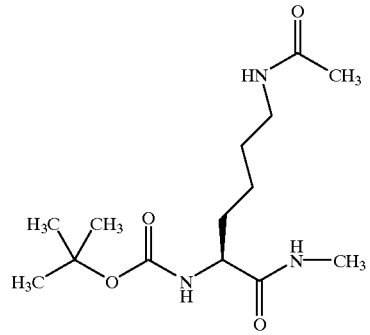

(2S)-5-(Acetylamino)-2-(tert-butoxycarbonylamino) hexanoic acid (purchased at Bachem, 5.0 g, 17.34 mmol) and 1-hydroxybenzotriazole hydrate (2.65 g, 17.34 mmol) were subsequently dissolved in dichloromethane (40 ml) and N,N-dimethylformamide (20 ml). The solution was cooled to 0° C. N-(3-Dimethylaminopropyl)-N'-ethylcarbodiimide hydrochloride (3.32 g, 17.34 mmol) was added. The reaction mixture was stirred at 0° C. for 20 min. A 8.0 M solution of methylamine in ethanol (13 ml, 104 mmol) was added. The reaction mixture was stirred for 16 h, while it was warming up to room temperature. It was diluted with ethyl acetate (300 ml) and washed with a 10% aqueous solution of sodium hydrogensulfate (300 ml). The aquoeus phase was extracted with ethyl acetate (2×150 ml). The combined organic layers were washed with a saturated aqueous solution of sodium hydrogen carbonate (300 ml) and dried over magnesium sulfate. The solvent was removed in vacuo. The crude product was purified by flash chromatography on silica (65 g), using dichloromethane/methanol (10:1) as eluent to give 792 mg of ((1S)-5-(acetylamino)-1-(methylcarbamoyl) pentyl)carbamic acid tert-butyl ester.

¹H-NMR (CDCl₃): d 1.30–1.90 (m, 6H); 1.44 (s, 9H); 1.99 (s, 3H); 2.82 (d, 3H); 3.25 (q, 2 H); 4.07 (m, 1H); 5.24 (br, d, 1H); 5.90 (br, 1H); 6.48 (br, 1H).

(2S)-6-Acetylamino-2-aminohexanoic acid methylamide

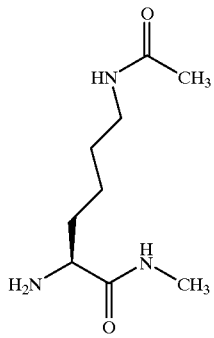

((1S)-5-(Acetylamino)-1-(methylcarbamoyl)pentyl) carbamic acid tert-butyl ester (792 mg, 2.63 mmol) were dissolved in ethyl acetate (50 ml). A 3 M solution of hydrogen chloride in ethyl acetate (50 ml, 150 mmol) was added. The reaction mixture was stirred for 20 min at room temperature. The solvent was removed by decantation. The residue was washed with ethyl acetate (2×20 ml) and dried in vacuo to give 566 mg of the crude hydrochloride salt of (2S)-6-acetylamino-2-aminohexanoic acid methylamide, which was used for the next step without purification.

$^1$H-NMR (DMSO-d$_6$): d 1.30 (m, 2H); 1.40 (m, 2H); 1.71 (m, 2H); 1.81 (s, 3H); 2.64 (d, 3H); 3.01 (m, 2H); 3.72 (m, 1H); 8.06 (br, 1H); 8.47 (br, 3H); 3.65 (q, 1H).

N-[(1R)-1-((1S)-5-(Acetylamino)-1-(methylcarbamoyl) pentylcarbamoyl)-2-phenylethyl]-N-methylcarbamic acid tert-butyl ester

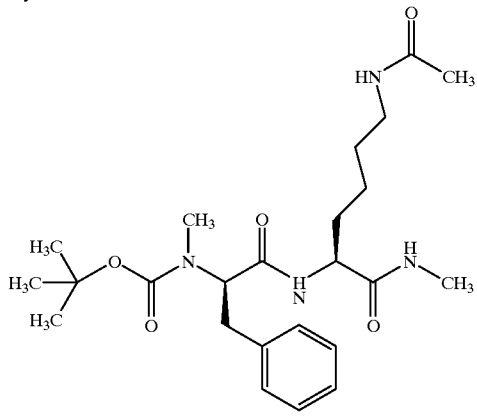

N-(3-Dimethylaminopropyl)-N'-ethylcarbodiimide hydrochloride (411 mg, 2.30 mmol) was added at 0° C. to a solution of (2R)-2-(N-(tert-butoxycarbonyl)-N-methylamino)-3-phenylpropionic acid (643 mg, 2.30 mmol) and 1-hydroxybenzotriazole hydrate (311 mg, 2.30 mmol) in dichloromethane (10 ml) and N,N-dimethylformamide (5 ml). The reaction mixture was stirred for 20 min at 0° C. A solution of the crude hydrochloride salt of (2S)-6-acetylamino-2-aminohexanoic acid methylamide (547 mg, 2.30 mmol) in N,N-dimethylformamide (5 ml) and ethyidiisopropylamine (1.18 ml, 6.90 mmol) were added subsequently. The reaction mixture was stirred for 3 days, while it was warming up to room temperature. It was diluted with ethyl acetate (70 ml) and washed with a 10% aqueous solution of sodium hydrogen sulfate (70 ml). The aqueous phase was extracted with ethyl acetate (2×40 ml).

The combined organic layers were washed with a saturated aqueous solution of sodium hydrogen carbonate (70 ml) and dried over magnesium sulfate. The solvent was removed in vacuo. The crude product was purified by flash chromatography on silica (80 g), using dichloromethane/methanol (20:1) as eluent to give 1.04 g of N-[(1R)-1-((.1S)-5-(acetylamino)-1-(methylcarbamoyl)pentylcarbamoyl)-2-phenylethyl]-N-methylcarbamic acid tert-butyl ester.

$^1$H-NMR (CDCl$_3$, selected values): d 1.41 (br, 9H); 1.99 (s, 3H); 3.20 (q, 2H); 3.37 (dd, 1 H); 4.39 (m, 1H); 4.52 (m, 2H).

(2S)-6-Acetylamino-2-((2R)-2-(methylamino)-3-phenylpropionylamino)hexanoic acid methylamide

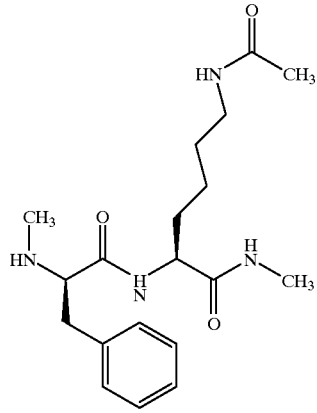

N-[(1R)-1-((1S)-5-(acetylamino)-1-(methylcarbamoyl) pentylcarbamoyl)-2-phenylethyl]-N-methylcarbamic acid tert-butyl ester (1.04 g, 2.25 mmol) was dissolved in ethyl acetate (20 ml). A 3 M solution of hydrogen chloride in ethyl acetate (60 ml, 180 mmol) was added. The reaction mixture was stirred at room temperature for 45 min. Ethyl acetate (50 ml) was added. The solvent was removed by decantation. The residue was washed with ethyl acetate (2×20 ml) and dried in vacuo to give 741 mg of the crude hydrochloride salt of (2S)-6-acetylamino-2-((2R)-2-(methylamino)-3-phenylpropionylamino)hexanoic acid methylamide, which was used for the next step without purification.

$^1$H-NMR (DMSO-d$_6$, selected values): d 0.81 (m, 2H); 1.10–1.55 (m, 4H); 1.79 (s, 3H); 3.23 (m, 1H); 4.03 (m, 2H).

N-((1R)-1-{N-[(1R)-1-((1S)-5-(Acetylamino)-1-(methylcarbamoyl)pentylcarbamoyl)-2-phenylethyl]-N-methylcarbamoyl}-2-(2-naphthyl)ethyl)-N-methylcarbamic acid tert-butyl ester

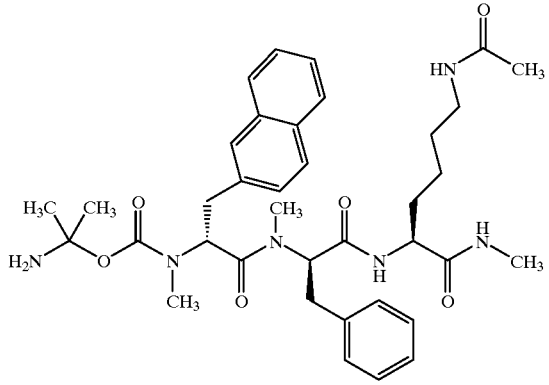

N-(3-Dimethylaminopropyl)-N'-ethylcarbodiimide hydrochloride (313 mg, 1.63 mmol) was added at 0° C. to a solution of (2R)-2-(N-(tert-butoxycarbonyl)-N-methylamino)-3-(2-naphthyl)propionic acid (537 mg, 1.63 mmol) and 1-hydroxy-7-azabenzotriazole (222 mg, 1.63 mmol) in dichloromethane (20 ml) and N,N- dimethylformamide (10 ml). The reaction mixture was stirred for 20 min at 0° C. A solution of the crude hydrochloride salt of (2S)-6-acetylamino-2-((2R)-2-(methylamino)-3-phenylpropionylamino)hexanoic acid methylamide (710 mg, 1.63 mmol) and ethyldiisopropylamine (0.84 ml, 4.89 mmol) were added subsequently, The reaction mixture was stirred for 16 h, while it was warming up to room temperature. It was diluted with ethyl acetate (70 ml) and washed with a 1 0% aqueous solution of sodium hydrogen sulfate (70 ml). The aqueous solution was extracted with ethyl acetate (2×60 ml). The combined organic layers were washed with a saturated aqueous solution of sodium hydrogen carbonate (70 ml) and dried over magnesium sulfate. The solvent was removed in vacuo. The crude product was purified by flash chromatography on silica (80 g), using dichloromethane./methanol (1 0: 1) as eluent to give 748 mg of N-((1R)-1-{N-[(1R)-1-(( 1S)-5-(acetylamino)-1-(methylcarbamoyl)pentylcarbamoyl)-2-phenylethyl]-N-methylcarbamoyl}-2-(2-naphthyl)ethyl)-N-methylcarbamic acid tert-butyl ester.

$^1$H-NMR (CDCl$_3$, selected values): d 1.92 and 1.99 (both s, together 3H); 4.32, 4.66, 4.82, 5.05, and 5.25 (all m, together 3H).

inethyl acetate (10 ml). A 3 M solution on hydrogen chloride in ethyl acetate (40 ml) was added. The reaction mixture was stirred for 30 min at room temperature. The solvent was removed by decantation. The residue was washed with ehyl acetate (2×40 ml). The residue was dried in vacuo to give 451 mg of the crude hydrochloride salt of (2S)-6-acetylamino-2-{(2R)-2-[N-methyl-N-((2R)-2-(methylamino)-3-(2-naphthyl)propionyl)amino]-3-phenylpropionylamino}hexanoic acid methylamide, which was used without further purification.

$^1$H-NMR (DMSO-d$_6$, selected values): d 0.70–1.70 (m, 6H); 4.38 (m); 5.50 (dd). (3E)-3-(N-((1R)-1-(N-((1R)-1-((1S)-5-(Acetylamino)-1-(methylcarbamoyl)pentylcarbamoyl)-2-phenylethyl)-N-methylcarbamoyl)-2-(2-naphthyl)ethyl)-N-methylcarbamoyl)-1,1-dimethylbut-3-enylcarbamic acid tert-butyl ester

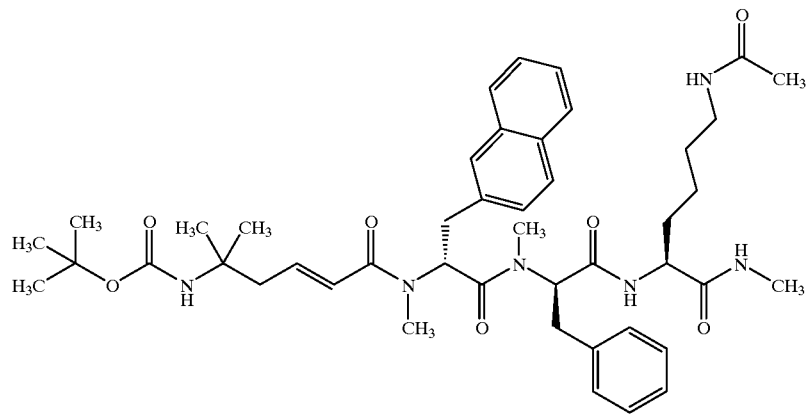

(2S)-6-Acetylamino-2-{(2R)-2-[N-methyl-N-((2R)-2-(methylamino)-3-(2-naphthyl)propionyl)amino]-3-phenylpropionylamino}hexanoic acid methylamide

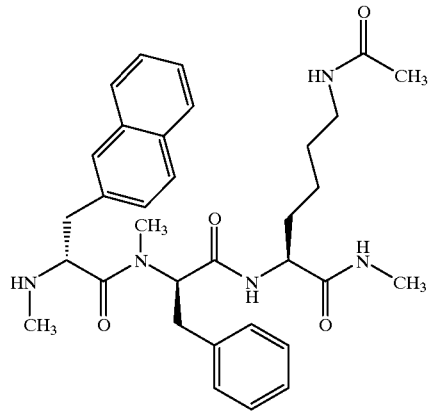

N-((1R)-1-{N-[(1R)-1-((1S)-5-(acetylamino)-1-(methylcarbamoyl)pentylcarbamoyl)-2-phenylethyl]-N-methylcarbamoyl}-2-(2-naphthyl)ethyl)-N-methylcarbamic acid tert-butyl ester (748 mg, 1.11 mmol) was dissolved N-(3-Dimethylaminopropyl)-N'-ethylcarbodiimide hydrochloride (142 mg, 0.74 mmol) was at 0° C. added to a solution of (2E)-5-(tert-butoxycarbonylamino)-5-methylhex-2-enoic acid (180 mg, 0.74 mmol) and 1-hydroxy-7-azabenzotriazole (100 mg, 0.74 mmol) in dichloromethane (10 ml) and N,N-dimethylformamide (5 ml). The reaction mixture was stirred at 0° C. for 20 min. A solution of the crude hydrochloride salt of (2S)-6-acetylamino-2-{(2R)-2-[N-methyl-N-((2R)-2-(methylamino)-3-(2-naphthyl)propionyl)amino]-3-phenylpropionylamino}hexanoic acid methylamide (451 mg, 0.74 mmol) in dichloromethane (10 ml) and N,N-dimethylformamide (5 ml) and ethyidiisopropylamine (0.38 ml, 2.22 mmol) were added subsequently. The reaction mixture was stirred for 16 h, while it was warming up to room temperature. It was diluted with ethyl acetate and washed with a 10% aqueous solution of sodium hydrogen sulfate (60 ml). The aqueous phase was extracted with ethyl acetate (2×50 ml). The combined organic layers were washed with a saturated aqueosu solution of sodium hydrogen carbonate (60 ml) and dried over magnesium sulfate. The solvent was removed in vacuo. The crude product was purified by flash chromatography on silica (40g), using dichloromethane/methanol (10:1) as eluent, to give 405 mg of (3E)-3-(N-((1R)-1-(N-((1R)-1-((1S)-5-(acetylamino)-1-(methylcarbamoyl)pentylcarbamoyl)-2-phenylethyl)-N-methylcarbamoyl)-2-(2-naphthyl)ethyl)-N-methylcarbamoyl)-2-(2-naphthyl)ethyl)-N- methylcarbamoyl)-1,1-dimethylbut-3-enylcarbamic acid tert-butyl ester.

$^1$H-NMR (CDCl$_3$, selected values): d 1.10–2.05 (m, 21H); 1.89, 1.90, 1,96, and 1.97 (all s, together 3H); 6.05 and 6.10 (both d, toegether 1H); 6.75 (m, 1H).

(3E)-3-(N-((1R)-1-(N-((1R)-1-((1S)-5-(Acetylamino)-1-(methylcarbamoyl)pentylcarbamoyl)-2-phenylethyl)-N-methylcarbamoyl)-2-(2-naphthyl)ethyl)-N-methylcarbamoyl)-1,1-dimethylbut-3-enylcarbamic acid tert-butyl ester (391 mg, 0.49 mmol) was dissolved in dichloromethane (8 ml). The solution was cooled to 0° C. Trifluoroacetic acid (8 ml) was added. The reaction mixture was stirred for 60 min at 0° C. It was diluted with dichloromethane (30 ml). A saturated aqueous solution of sodium hydrogen carbonate (30 ml) was added carefully. Solid sodium hydrogen carbonate was added until pH 7. The phases were separated. The aqueous phase was extracted with dichloromethane (3×25 ml). The combined organic layers were dried over magnesium sulfate. The solvent was removed in vacuo. The crude product was purified by flash chromatography on silica (40 g), using dichloromethane/methanol/25% aqueous ammonia (first: 100:10: 1, then 50:10:1) as eluent to give 124 mg of the title compound.

$^1$H-NMR (CDCl$_3$, selected values): d 1.04, 1.10 and 1.11 (all s, together 6H); 1.90 and 1.96 (both s, together 3H); 2.69 and 2.73 (both d, together 3H); 2.78, 2.87, 2.92, and 3.05 (all s, together 6H); 6.06 and 6.11 (both d, together 1H); 6.85 (m, 1H).

MS: 699.6 [M+1]$^+$

HPLC 31.57 min (A1).

33.47 min (B1).

For biological testing, the title compound was transferred into its acetate salt, by lyophilization with 0.5 m acetic acid (40 ml).

What is claimed is:

1. A compound of general formula I

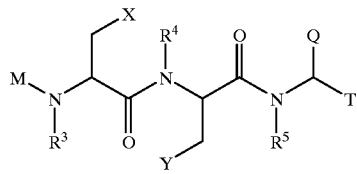

(I)

wherein

R$^3$, R$^4$ and R$^5$ independently of each other are hydrogen or C$_{1-6}$ alkyl optionally substituted with C$_{1-6}$ alkyl, X is aryl optionally substituted with halogen, C$_{1-6}$ alkyl or phenyl, Y is aryl or hetaryl optionally substituted with halogen, C$_{1-6}$ alkyl, C$_{1-6}$ alkoxy or phenyl, M is M$^1$, M$^2$, M$^3$, M$^4$ or M$^5$, wherein M$^1$ is —C(=O)—CH=CH—(CH$_2$)m—C(R$^{16}$R$^{17}$)—N(R$^1$R$^2$), M$^2$ is —C(=O)—CH((CH$_2$)$_m$-hetaryl)—NH—C(=O)—C(R$^{16}$R$^{17}$)—N(R$^1$R$^2$), wherein m is 1, 2 or 3, and R$^{16}$ and R$^{17}$ independently of each other are C$_{1-6}$ alkyl, optionally substituted with halogen, amino, hydroxyl, C$_{1-6}$ alkyl, C$_{1-6}$ alkoxy or phenyl;

M$^3$ is —C(=O)—D$^1$—CH$_2$—N(R$^1$R$^2$),

M$^4$ is —C(=O)—D$^1$—C(R$^6$R$^7$)—N(R$^1$R$^2$), and

M$^5$ is —C(=O)—(CH$_2$)$_s$—O—(CH$_2$)$_p$—C(R$^6$R$^7$)$_q$—A, wherein R$^6$ and R$^7$ independently of each other are hydrogen or C$_{1-6}$ alkyl, D$^1$ is arylene, p and s independently of each other are 1, 2 or 3, q is 0 or 1, and A is —N(R$^1$R$^2$) or a saturated heterocyclic ring containing 5 or 6 ring members, one ring member being a nitrogen atom, wherein R$^1$ and R$^2$ independently of each other are hydrogen, —C(=O)—C$_{1-6}$ alkyl, C$_{1-6}$ alkyl optionally substituted with halogen, amino, hydroxyl, C$_1$ alkyl, C$_{1-6}$ alkoxy or phenyl; or benzyl, optionally substituted with halogen, amino, hydroxyl, C$_{1-6}$ alkyl, C$_{1-6}$ alkoxy or phenyl, T is hydrogen, T$^1$, T$^2$ or T$^3$, wherein T$^1$ is —(CH$_2$)$_n$—NH$_2$, wherein n is 1, 2, 3, 4, 5, 6, 7, 8, 9 or 10, T$^2$ is —(CH$_2$)$_n$—N(R$^8$R$^9$), wherein n is 1, 2, 3, 4, 5, 6, 7, 8, 9 or 10, and R$^8$ and R$^9$ independently of each other are C$_{1-6}$ alkyl optionally substituted with halogen, amino, hydroxyl, C$_{1-6}$ alkyl, C$_{1-6}$ alkoxy or phenyl, or R$^8$ and R$^9$ may be joined to form a saturated heterocyclic ring containing 5 or 6 ring members, one of the ring members being a nitrogen and the other four or five being carbon atoms; and T$^3$ is —(CH$_2$)$_n$—NHZ, wherein n is 1, 2, 3, 4, 5, 6, 7, 8, 9 or 10, and Z is —C(=O)—R$^{10}$, —C(=O)—O—R$^{10}$, —SO$_2$R$^{10}$ or —C(=O)—NR$^{11}$R$^{12}$, wherein R$^{10}$ is hydrogen, C$_{1-6}$ alkyl optionally substituted with halogen, amino, hydroxyl, C$_{1-6}$ alkyl, C$_{1-6}$ alkoxy or phenyl; benzyl, optionally substituted with halogen, amino, hydroxyl, C$_{1-6}$ alkyl, C$_{1-6}$ alkoxy or phenyl; or 3a,7a,12a-trihydroxy-5b-cholanyl, and R$^{11}$ and R$^{12}$ independently of each other are hydrogen, C$_{1-6}$ alkyl optionally substituted with halogen, amino, hydroxyl, C$_{1-6}$ alkyl, C$_{1-6}$ alkoxy or phenyl; or benzyl, optionally substituted with halogen, amino, hydroxyl, C$_{1-6}$ alkyl, C$_{1-6}$ alkoxy or phenyl, Q is hydrogen, Q$^1$, Q$^2$ or Q$^3$, wherein Q$^1$ is —C(=O)—NHR$^{13}$, Q$^2$ is —C(=O)—NH$_2$, and Q$^3$ is —C(=O)—NR$^{14}$R$^{15}$, wherein R$^{13}$, R$^{14}$ and R$^{15}$ independently of each other are C$_{1-6}$ alkyl optionally substituted with halogen, amino, hydroxyl, C$_{1-6}$ alkyl, C$_{1-6}$ alkoxy or phenyl;

or a pharmaceutically acceptable salt thereof;

with the proviso(s) that if M is M$^2$ then T cannot be hydrogen, T$^1$ or T$^2$, if T is hydrogen then Q cannot be hydrogen, if M is M$^1$ or M$^3$ then R$^4$ cannot be hydrogen, if M is M$^3$ and X is 2-naphthyl or phenyl and Y is phenyl and T is T$^1$ then Q cannot be Q$^2$, if T is T$^2$ and n is 2 then R$^5$ cannot be hydrogen, if Q is Q$_3$ and Y is phenyl and X is 2-naphthyl and R$^3$, R$^4$ and R$^5$ are methyl, then M cannot be M$^1$, if T is T$^2$ and n is 3 and Y is phenyl and X is 2-naphthyl and R$^3$, R$^4$ and R$^5$ are methyl, then M cannot be M$^1$, if T is H and X is napthyl and Y is phenyl and R$_5$ is H then M cannot be M$^1$, or if n is 2 and Q is H and T is T$_2$ and X is napthyl and Y is phenyl then M cannot be M$^1$.

2. The compound according to claim 1, wherein R$^1$ is hydrogen or C$_{1-6}$ alkyl.

3. The compound according to claim 1, wherein R$^2$ is hydrogen, C(=O)-C$_{1-6}$ alkyl or C$_{1-6}$ alkyl.

4. The compound according to claim 1, wherein M is hydrogen, —C(=O)—CH=CH—(CH$_2$)—C(R$^{16}$R$^{17}$)—N(R$^1$R$^2$), —C(=O)—CH(CH$_2$-hetaryl)—NH—C(=O)—C ($R^{16}R^{17}$)—N($R^1R^2$), —C(=O)—$D^1$—C($R^6R^7$)—N($R^1R^2$), —C(=O)—$CH_2$—O—$CH_2$—C($R^6R^7$)—N($R^1R^2$) or —C(=O)—$CH_2$—O—$CH_2$—A, wherein $R^{16}$ and $R^{17}$ independently of each other are $C_{1-6}$ alkyl, optionally substituted with halogen, amino, hydroxyl, $C_{1-6}$ alkyl, $C_{1-6}$ alkoxy or phenyl, $R^6$ and $R^7$ independently of each other are hydrogen or $C_{1-6}$ alkyl, $R^1$ and $R^2$ independently of each other are hydrogen, —C(=O)—$C_{1-6}$ alkyl, $C_{1-6}$ alkyl optionally substituted with halogen, amino, hydroxy, $C_{1-6}$ alkyl, $C_{1-6}$ alkoxy or phenyl; or benzyl, optionally substituted with halogen, amino, hydroxyl, $C_{1-6}$ alkyl, $C_{1-6}$ alkoxy or phenyl, $D^1$ is arylene and A is a saturated heterocyclic ring containing 5 or 6 ring members, one ring member being a nitrogen.

5. The compound according to claim 1, wherein $R^3$, $R^4$ and $R^5$ independently of each other are hydrogen or $C_{1-6}$ alkyl.

6. The compound according to claim 1, wherein X is aryl optionally substituted with $C_{1-6}$ alkyl or phenyl.

7. The compound according to claim 1, wherein Y is hetaryl or phenyl optionally substituted with halogen.

8. The compound according to claim 1, wherein Q is hydrogen, —C(=O)—$NHR^{13}$, —C(=O)—$NH_2$ or —C(=O)—$NR^{14}R^{15}$, wherein $R^{13}$, $R^{14}$ and $R^{15}$ independently of each other are $C_{1-6}$ alkyl.

9. The compound according to claim 1, wherein T is hydrogen, —$(CH_2)_n$—$NH_2$, —$(CH_2)_n$—N($R^8R^9$) or —$(CH_2)_n$—NHZ, wherein n is 1, 2, 3, 4, 5 or 6, $R^8$ and $R^9$ independently of each other are $C_{1-6}$ alkyl, or $R^8$ and $R^9$ may be joined to form a saturated heterocyclic ring containing 5 ring members, and Z is —C(=O)—$R^{10}$, —C(=O)—O—$R^{10}$, $SO_2R^{10}$ or —C(=O)—$NR^{11}R^{12}$, wherein $R^{10}$ is hydrogen, $C_{1-6}$ alkyl, benzyl or 3a,7a,12a-trihydroxy-5b-cholanyl, and $R^{11}$ and $R^{12}$ independently of each other are hydrogen, $C_{1-6}$ alkyl or benzyl.

10. The compound according to claim 1 selected from the group consisting of

3-Aminomethyl-N-((1R)-1-(((1R)-2-(2-thienyl)-1-((1S)-1-carbamoyl-5-aminopentylcarbamoyl)ethyl)-N-methylcarbamoyl)-2-(2-napthyl)ethyl)benzamide, 3-((1R/S)-1-Aminoethyl)-N-((1R)-1-{N-[(1R)-1-(N-(carbamoylmethyl)-N-methylcarbamoyl)-2-phenylethyl]-N-methylcarbamoyl}-2-(2-naphthyl)ethyl)-N-methylbenzamide, 2-Amino-N-(((1S)-1-(((1R)-1-(((1R)-1-(((1S)-1-carbamoyl-5-(methylsulfonylamino)pentyl)carbamoyl)-2-phenylethyl)carbamoyl)-2-(2-naphthyl)ethyl)carbamoyl)-2-(4-imidazolyl)ethyl)carbamoyl)-2-methylpropanamide,

[(5S)-5-((2R)-2-{N-[(2R)-2-(3-(Aminomethyl)benzoylamino)-3-(2-naphthyl)propionyl]-N-methylamino}-3-(2-thienyl)propionylamino)-5-carbamoylpentyl]carbamic acid benzyl ester, N-((1R)-1-{N-[(1R)-1-(((1S)-5-Amino-1-carbamoylpentyl)carbamoyl)-2-(4-fluorophenyl)ethyl]-N-methylcarbamoyl}-2-(biphenyl-4-yl)ethyl)-3-aminomethylbenzamide, (2E)-5-Amino-5-methylhex-2-enoic acid N-((1R)-1-N-[(1R)-1-(5-aminopentylcarbamoyl)-2-phenylethyl]-N-methylcarbamoyl}-2-(2-naphthyl)ethyl)-N-methylamide, 3-((1R/S)-1-Aminoethyl)-N-[(1R)-2-(biphenyl-4-yl)-1-(N-{(1R)-1-[N-(3-dimethylaminopropyl)-N-methylcarbamoyl]-2-phenylethyl}-N-methylcarbamoyl)ethyl]-N-methylbenzamide, (2E)-5-Amino-5-methylhex-2-enoic acid N-[(1R)-2-(biphenyl-4-yl)-1-(N-{(1R)-1-[N-(3-dimethylaminopropyl)-N-methylcarbamoyl]-2-phenylethyl}-N-methylcarbamoyl)ethyl]-N-methylamide, (2E)-5-Amino-5-methylhex-2-enoic acid N-((1R)-1-{N-[(1R)-1-((1S)-5-amino-1-carbamoylpentylcarbamoyl)-2-phenylethyl]-N-methylcarbamoyl}-2-(2-naphthyl)ethyl)-N-methylamide, N-((1R)-1-{N-[(1R)-1-((1S)-5-Amino-1-carbamoylpentylcarbamoyl)-2-phenylethyl]-N-methylcarbamoyl}-2-(2-naphthyl)ethyl)-3-((1R/S)-1-aminoethyl)-N-methylbenzamide, (2E)-5-Amino-5-methylhex-2-enoic acid ((1R)-1-{N-[(1R)-1-(((1S)-5-amino-1-(dimethylcarbamoyl)pentyl)carbamoyl)-2-phenylethyl]-N-methylcarbamoyl}-2-(2-naphthyl)ethyl)amide, N-((1R)-1-{N-[(1R)-1-(((1S)-5-Amino-1-(dimethylcarbamoyl)pentyl)carbamoyl)-2-phenylethyl]-N-methylcarbamoyl}-2-(biphenyl.-4-yl)ethyl)-3-aminomethyl-N-methylbenzamide, (2E)-5-Amino-5-methyl-hex-2-enoic acid N-((1R)-1-{N-[(1R)-1-((1S)-5-amino-1-(dimethylcarbamoyl)pentylcarbamoyl)-2-phenylethyl]-N-methy.lcarbamoyl}-2-(biphenyl-4-yl)ethyl)-N-methylamide, N-((1R)-1-{[(1R)-1-(((1S)-5-Amino-1-carbamoylpentyl)carbamoyl)-2-(4-fluorophenyl)ethyl]-N-methylcarbamoyl}-2-(2-naphthyl)ethyl)-3-aminomethylbenzamide, (2E)-5-Amino-5-methylhex-2-enoic acid ((1R)-1-{N-[(1R)-1-(((5S)-5-amino-1-carbamoylpentyl)carbamoyl)-2-(4-fluorophenyl)ethyl]-N-methylcarbamoyl}-2-(2-naphthyl)ethyl)amide, N-((1R)-1-{N-[(1R)-1-(((1S)-5-Amino-1-carbamoylpentyl)carbamoyl)-2-(4-fluorophenyl)ethyl]-N-methylcarbamoyl}-2-(2-naphtyl)ethyl)-3-aminomethyl-N-methylbenzamide, (2S)-6-Amino-2-[(2R)-3-(4-fluorophenyl)-2-(N-methyl-N-{(2R)-3-(2-naphthyl)-2-[2-(((2S)-pyrrolidin-2-yl)methoxy)acetylamino]-propionyl}amino)propionylamino]hexanoic acid amide, (2S)-6-Amino-2-[(2R)-2-(N-{(2R)-2-[2-((2R/S)-2-aminobutoxy)acetylamino]-3-(2-naphthyl)propionyl}-N-methylamino)-3-(4-fluorophenyl)propionylamino]hexanoic acid amide, (2E)-5-Amino-5-methylhex-2-enoic acid N-((1R)-1-{N-[(1R)-1-(((1S)-5-amino-1-carbamoylpentyl)carbamoyl)-2-phenylethyl]-N-methylcarbamoyl}-2-(2-naphthyl)ethyl)amide, (2E)-5-Amino-5-methylhex-2-enoic acid N-((1R)-1-{N-[(1R)-1-(((1S)-5-amino-1-carbamoylpentyl)carbamoyl)-2-phenylethyl]-N-methylcarbamoyl}-2-(biphenyl-4-yl)ethyl}amide, N-((1R)-1-{N-[(1R)-1-(((1S)-5-Amino-1-carbamoylpentyl)carbamoyl)-2-phenylethyl]-N-methylcarbamoyl}-2-(biphenyl-4-yl)ethyl)-3-aminomethylbenzamide, (2E)-5-Amino-5-methylhex-2-enoic acid N-((1R)-1-{N-[(1R)-1-(((1S)-5-amino-1-carbamoylpentyl)carbamoyl)-2-(2-thienyl)ethyl]-N-methylcarbamoyl)-2-(2-naphthyl)ethyl}amide, 3-Aminomethyl-N-((1R)-1-(((1R)-2-(2-thienyl)-1-((1S)-1-carbamoyl-5-aminopentylcarbamoyl)ethyl)-N-methylcarbamoyl)-2-(2-napthyl)ethyl)benzamide, (2E)-5-Amino-5-methylhex-2-enoic acid N-((1R)-1-{N-[(1R)-1-(((1S)-5-amino-1-carbamoylpentyl)

carbamoyl)-2-(2-thienyl)ethyl]-N-methylcarbamoyl}-2-(biphenyl-4-yl)ethyl}amide,

N-((1R)-1-{N-[(1R)-1-(((1S)-5-Amino-1-carbamoylpentyl)carbamoyl)-2-(2-thienyl)ethyl]-N-methylcarbamoyl}-2-(biphenyl-4-yl)ethyl)-3-aminomethylbenzamide, (2E)-5-Amino-5-methylhex-2-enoic acid N-((1R)-1-{N-[(1R)-1-(((1S)-5-acetylamino-1-carbamoylpentyl)carbamoyl)-2-phenylethyl]-N-methylcarbamoyl}-2-(2-naphthyl)ethyl)amide, (2E)-5-Amino-5-methylhex-2-enoic acid N-((1R)-1-{N-[(1R)-1-(((1S)-5-acetylamino-1-carbamoylpentyl)carbamoyl)-2-(2-thienyl)ethyl]-N-methylcarbamoyl}-2-(biphenyl-4-yl)ethyl)amide, (2E)-5-Amino-5-methylhex-2-enoic acid N-((1R)-1-{N-[(1R)-1-(((1S)-5-acetylamino-1-carbamoylpentyl)carbamoyl)-2-phenylethyl]-N-methylcarbamoyl)-2-(biphenyl-4-yl)ethyl)amide, (2E)-5-Amino-5-methylhex-2-enoic acid N-((1R)-1-{N-[(1R)-1-((1S)-5-acetylamino-1-carbamoylpentylcarbamoyl)-2-(2-thienyl)ethyl]-N-methylcarbamoyl}-2-(2-naphthyl)ethyl}amide, (2)-5-Amino-5-methylhex-2-enoic acid N-((1R)-1-{N-[(1R)-1-(6-aminohexylcarbamoyl)-2-phenylethyl]-N-methylcarbamoyl}-2-(biphenyl-4-yl)ethyl)-N-methylamide, (2E)-5-Amino-5-methylhex-2-enoic acid N-((1R)-1-{N-[(1R)-1-(4-aminobutylcarbamoyl)-2-phenylethyl]-N-methylcarbamoyl}-2-(biphenyl-4-yl)ethyl)-N-methylamide, (2E)-5-Amino-5-methylhex-2-enoic acid N-((1R)-1-{N-[(1R)-1-(3-aminopropylcarbamoyl)-2-phenylethyl]-N-methylcarbamoyl}-2-(biphenyl-4-yl)ethyl)-N-methylamide, (2E)-5-Amino-5-methylhex-2-enoic acid N-((1R)-1-{N-[(1R)-1-(2-aminoethylcarbamoyl)-2-phenylethyl]-N-methylcarbamoyl}-2-(biphenyl-4-yl)ethyl)-N-methylamide, 3-(1-Aminoethyl)-N-((1R)-1-(N-((1R)-1-(N-(3-dimethylaminopropyl)-N-methylcarbamoyl)-2-phenylethyl)-N-methylcarbamoyl)-2-(2-naphthyl)ethyl)-N-methylbenzamide, 3-(1-Aminoethyl)-N-((1R)-1-(N-((1R)-1-(N-((dimethylcarbamoyl)methyl)-N-methylcarbamoyl)-2-phenylethyl)-N-methylcarbamoyl)-2-(2-naphthyl)ethyl)-N-methylbenzamide (2S)-6-Acetylamino-2-((2R)-2-{(2R)-2-[(2S)-2-(2-amino-2-methylpropionylamino)-3-(imidazol-4-yl)propionylamino]-3-(2-naphthyl)propionylamino}-3-phenylpropionylamino)hexanoic acid amide, (2S)-5-Ureido-2-((2R)-2-(2R)-2-[(2S)-2-(2-amino-2-methylpropionylamino)-3-(3H-imidazol-4-yl)propionylamino]-3-(2-naphthyl)propionylamino}-3-phenylpropionylamino)pentanoic acid amide, (2S)-6-tert Butyloxycarbonylamino-2-((2R)-2-{(2R)-2-[(2S)-2-(2-amino-2-methylpropionylamino)-3-(imidazol-4-yl)propionylamino]-3-(2-naphthyl)propionylamino}-3-phenylpropionylamino)hexanoic acid amide, (2S)-6-Acetylamino-2-((2R)-2-{N-((2R)-2-[(2S)-2-(2-amino-2-methylpropionylamino)-3-(imidazol-4-yl)propionylamino]-3-(2-naphthyl)propionyl)-N-methylamino}-3-phenylpropionylamino)hexanoic acid amide, (2S)-6-(3a,7a,12a-trihydroxy-5b-cholanoylamino)-2-((2R)-2-{(2R)-2-[(2S)-2-(2-amino-2-methylpropionylamino)-3-(3H-imidazol-4-yl)propionylamino]-3-(2-naphthyl)propionylamino}-3-phenylpropionylamino)hexanoic acid amide, (2E)-5-Amino-5-methylhex-2-enoic acid ((1R)-1-{N-[(1R)-1-(5-aminopentylcarbamoyl)-2-phenylethyl]-N-methylcarbamoyl}-2-(2-naphthyl)ethyl)amide, (2E)-5-Amino-5-methylhex-2-enoic acid N-((1R)-1-{N-[(1R)-1-(5-aminopentylcarbamoyl)-2-phenylethyl]-N-methylcarbamoyl}-2-(2-naphthyl)ethyl)-N-methylamide, N-((1R)-1-{N-[(1R)-1-(4-Aminobutylcarbamoyl)-2-phenylethyl]-N-methylcarbamoyl}-2-(biphenyl-4-yl)ethyl)-3-aminomethyl-N-methylbenzamide, 3-Aminomethyl-N-({1 R}-1-{N-[(1R)-1-(5-aminopentylcarbamoyl)-2-phenylethyl]-N-methylcarbamoyl}-2-(2-naphthyl)ethyl)benzamide, 3-Aminomethyl-N-((1R)-1-{N-[(1R)-1-(5-aminopentylcarbamoyl)-2-phenylethyl]-N-methylcarbamoyl}-2-(2-naphthyl)ethyl)-N-methylbenzamide, (2E)-5-Amino-5-methylhex-2-enoic acid N-((1R)-1-{N-[(1R)-1-((4-dimethylaminobutyl)carbamoyl)-2-phenylethyl]-N-methylcarbamoyl}-2-(2-naphthyl)ethyl)-N-methylamide, (2E)-5-Amino-5-methylhex-2-enoic acid N-((1R)-1-{N-[(1R)-1-(5-guanidinopentylcarbamoyl)-2-phenylethyl]-N-methylcarbamoyl}-2-(2-naphthyl)ethyl)-N-methylamide, (2E)-5-Amino-5-methylhex-2-enoic acid N-[(1R)-1-(N-{(1R)-1-[5-(3-ethylureido)pentylcarbamoyl]-2-phenylethyl}-N-methylcarbamoyl)-2-(2-naphthyl)ethyl]-N-methylamide, 3-Aminomethyl-N-[(1R)-1-(N-{(1R)-1-[N-(2-(dimethylamino)ethyl)-N-methylcarbamoyl]-2-phenylethyl}-N-methylcarbamoyl)-2-(2-naphthyl)ethyl]-N-methylbenzamide, N-[(1R)-1-(N-{(1R)-1-[N-(2-(Dimethylamino)ethyl)-N-methylcarbamoyl]-2-phenylethyl}-N-methylcarbamoyl)-2-(2-naphthyl)ethyl]-N-methyl-3-(methylaminomethyl)benzamide, 3-((1R/S)-1-Aminoethyl)-N-[(1R)-1-(N-{(1R)-1-[N-(2-(dimethylamino)ethyl)-N-methylcarbamoyl]-2-phenylethyl}-N-methylcarbamoyl)-2-(2-naphthyl)ethyl]-N-methylbenzamide, (2E)-5-Amino-5-methylhex-2-enoic acid N-((1R)-2-(biphenyl-4-yl)-1-{N-[(1R)-1-(4-(dimethylamino)butylcarbamoyl)-2-phenylethyl]-N-methylcarbamoyl}ethyl)-N-methylamide, (2E)-5-Amino-5-methylhex-2-enoic acid N-[(1R)-1-(N-{(1R)-1-[N-(2-dimethylaminoethyl)-N-methylcarbamoyl]-2-phenylethyl}-N-methylcarbamoyl)-2-(2-naphthyl)ethyl]-N-methylamide, (2E)-5-Amino-5-methylhex-2-enoic acid N-((1R)-1-{N-[(1R)-1-((4-dimethylaminobutyl)carbamoyl)-2-(2-thienyl)ethyl]-N-methylcarbamoyl}-2-(2-naphthyl)ethyl)-N-methylamide, (2E)-5-Amino-5-methylhex-2-enoic acid N-((1R)-2-(4-biphenyl-4-yl)-1-{N-[(1R)-1-((4-dimethylaminobutyl)carbamoyl)-2-(2-thienyl)ethyl]-N-methylcarbamoyl}ethyl)-N-methylamide, (2E)-5-Amino-5-methylhex-2-enoic acid N-((1R)-1-{N-[(1R)-1-((1S)-5-(acetylamino)-1-(dimethylcarbamoyl)

pentylcarbamoyl)-2-phenylethyl]-N-methylcarbamoyl}-2-(2-naphthyl)ethyl)-N-methylamide, and (2E)-5-Amino-5-methylhex-2-enoic acid N-((1R)-1-{N-[(1R)-1-((1S)-5-acetylamino-1-(methylcarbamoyl)pentylcarbamoyl)-2-phenylethyl]-N-methylcarbamoyl}-2-(2-naphthyl)ethyl)-N-methylamide;

or a pharmaceutically acceptable salt thereof.

11. A pharmaceutical composition comprising a compound according to claim 1 together with a pharmaceutically acceptable carrier or diluent.

12. The composition according to claim 11 in unit dosage form, comprising from about 10 to about 200 mg of the compound according to claim 1.

13. A pharmaceutical composition for stimulating the release of growth hormone from the pituitary, the composition comprising a compound according to claim 1 together with a pharmaceutically acceptable carrier or diluent.

14. A pharmaceutical composition for administration to animals to increase their rate and extent of growth, to increase their milk and wool production, or for the treatment of ailments, the composition comprising a compound according to claim 1 together with a pharmaceutically acceptable carrier or diluent.

15. A pharmaceutical composition according to claim 1, for oral, nasal, transdermal, pulmonal, or parenteral administration.

16. A method of stimulating the release of growth hormone from the pituitary, the method comprising administering to a subject in need thereof an effective amount of a compound according to claim 1 or of a composition according to claim 11.

17. The method according to claim 16, wherein the effective amount of the compound is in the range of from about 0.0001 to about 100 mg/kg body weight per day.

18. A method for increasing the rate and extent of growth of animals to increase their milk and wool production, or for the treatment of ailments, the method comprising administering to a subject in need thereof an effective amount of a compound according to claim 1 or of a composition according to claim 11.

19. The method according to claim 16, wherein said administration is oral, nasal, transdermal, pulmonal or parenteral.

20. The method according to claim 17, wherein the effective amount of the compound is in the range of from about 0.001 to about 50 mg/kg body weight per day.

21. The method according to claim 18, wherein said administration is oral, nasal, transdermal, pulmonal or parenteral.

* * * * *